United States Patent
Borzilleri et al.

(10) Patent No.: US 8,889,712 B2
(45) Date of Patent: Nov. 18, 2014

(54) IAP ANTAGONISTS

(71) Applicant: Bristol-Myers Squibb Company, Princeton, NJ (US)

(72) Inventors: Robert M. Borzilleri, New Hope, PA (US); Heidi L. Perez, Ewing, NJ (US); Erik M. Stang, Lawrenceville, NJ (US); Kyoung S. Kim, North Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/921,467

(22) Filed: Jun. 19, 2013

(65) Prior Publication Data

US 2013/0338081 A1    Dec. 19, 2013

Related U.S. Application Data

(60) Provisional application No. 61/661,460, filed on Jun. 19, 2012, provisional application No. 61/787,808, filed on Mar. 15, 2013.

(51) Int. Cl.
*A61K 31/47* (2006.01)
*C07D 401/12* (2006.01)
*C07D 401/14* (2006.01)
*C07K 7/02* (2006.01)
*A61K 38/08* (2006.01)
*C07D 413/14* (2006.01)
*A61K 45/06* (2006.01)
*C07D 401/04* (2006.01)

(52) U.S. Cl.
CPC .............. *A61K 38/08* (2013.01); *C07D 401/14* (2013.01); *C07K 7/02* (2013.01); *C07D 413/14* (2013.01); *A61K 45/06* (2013.01); *C07D 401/12* (2013.01); *C07D 401/04* (2013.01)
USPC ............................ 514/307; 514/310; 546/146

(58) Field of Classification Search
None
See application file for complete search history.

(56) References Cited

FOREIGN PATENT DOCUMENTS

| WO | WO 2009/136290 | 11/2009 |
| WO | WO 2013/071027 | 5/2013 |
| WO | WO 2013/071035 | 5/2013 |
| WO | WO 2013/071039 | 5/2013 |

*Primary Examiner* — Zinna Northington Davis
(74) *Attorney, Agent, or Firm* — Elliott Korsen

(57) ABSTRACT

There are disclosed compounds that modulate the activity of inhibitors of apoptosis (IAPs), pharmaceutical compositions containing said compounds and methods of treating proliferative disorders and disorders of dysregulated apoptosis, such as cancer, utilizing the compounds of the invention.

13 Claims, No Drawings

IAP ANTAGONISTS

CONTINUING DATA

This application claims benefit of 61/661,460 filed Jun. 19, 2012 and claims benefit of 61/787,808 filed Mar. 15, 2013.

FIELD OF THE INVENTION

The invention relates generally to compounds that modulate the activity of inhibitors of apoptosis (IAPs), pharmaceutical compositions containing said compounds and methods of treating proliferative disorders and disorders of dysregulated apoptosis, such as cancer, utilizing the compounds of the invention.

BACKGROUND OF THE INVENTION

Apoptosis or programmed cell death is a genetically and biochemically regulated mechanism that plays an important role in development and homeostasis in invertebrates as well as vertebrates.

Aberrancies in apoptosis that lead to premature cell death have been linked to a variety of developmental disorders. Deficiencies in apoptosis that result in the lack of cell death have been linked to cancer and chronic viral infections.

Caspases are cysteine-containing aspartate specific proteases that play a key role in effecting apoptosis. Once activated from their inactive zymogen form by proteolytic processing, caspases digest vital cell proteins from within the cell. Since caspases are such strong proteases, tight control of this family of proteins is necessary to prevent premature cell death. In addition to proteolytic processing, caspases are also regulated by a family of molecules known as Inhibitors of Apoptosis Proteins (TAP). IAPs are naturally occurring intracellular proteins that suppress caspase-dependent apoptosis. SMAC, an intracellular protein also known as DIABLO, functions to modulate the activity of IAPs. In normal healthy cells, SMAC and IAPs function together to maintain healthy cells. However, in certain disease states, e.g., cancers and other proliferative disorders, the activities of IAPs are not adequately modulated and therefore, prevent apoptosis and cause or exacerbate abnormal proliferation and survival.

IAP antagonists, also known as SMAC mimetics, are synthetic molecules that mimic the structure and IAP modulating activity of the four N-terminal amino acids of SMAC (AVPI). When administered to a subject suffering proliferative disorders, the compounds antagonize IAP activities causing an increase in apoptosis among abnormally proliferating cells.

IAPs are found in all organisms ranging from *Drosophila* to human and are known to be overexpressed in many human cancers. IAPs comprise one to three Baculovirus IAP repeat (BIR) domains. The BIR domain is a zinc binding domain of about 70 residues comprising 4 alpha-helices and 3 beta strands, with cysteine and histidine residues that coordinate the zinc ion. The BIR 2 and 3 domains contain a conserved inhibitor of apoptosis binding motif (IBM) capable of binding caspases—and inhibiting their proteolytic activity.

As an example, human X-chromosome linked IAP (XIAP) inhibits the executioner caspases-3, and -7 as well as the Apaf-1-cytochrome C mediated activation of the initiator caspase-9. Caspases-3 and -7 are inhibited by the BIR2 domain of XIAP, while the BIR3 domain of XIAP is responsible for the inhibition of caspase-9 activation. XIAP is expressed ubiquitously in most adult and fetal tissues. Overexpression of XIAP in tumor cells has been demonstrated to confer protection of the tumor cells against a variety of pro-apoptotic stimuli and promotes resistance to chemotherapy. Consistent with this, a strong correlation between XIAP protein levels and survival has been demonstrated for patients with acute myelogenous leukemia.

Other BIR2-3 containing IAP family members, while capable of binding caspases, do not directly inhibit their proteolytic activity. Rather they inhibit apoptosis by affecting signaling activities of key proteins in cell survival pathways. Like XIAP, these IAPs possess a carboxyl-terminal RING finger domain capable of conjugating ubiquitin to specific protein substrates. As an example, cellular IAPs 1 and 2 (cIAP1/2), ubiquitinate RIPK, a signaling intermediate of tumor necrosis death receptor (TNF-DR) activation. Ubiquitinated RIPK is unable to activate caspase-8 in the context of DR activation by TNF family DR ligands. On the contrary, the long ubiquitin chains attached to RIPK provide a scaffold by which cell components of the NFκB cell survival signaling cascade can attach and become activated.

In normal cells undergoing apoptosis, the IAP-mediated inhibition is removed by the mitochondrial protein SMAC (second mitochondrial activator of caspases; also known as DIABLO). SMAC is synthesized as a precursor molecule of 239 amino acids; the N-terminal 55 residues serving as the mitochondria targeting sequence that is removed after import. The mature form of SMAC resides in the inter-membrane space of mitochondria. At the time of apoptosis induction, SMAC is released from mitochondria into the cytosol where, together with cytochrome c, it binds to XIAP, and eliminates its' inhibitory effect on caspases. SMAC also binds cIAP 1/2 and inhibits their ability to ubiquinate RIPK. SMAC interacts with essentially all IAPs that have been examined to date and thus appears to be a master regulator of apoptosis in mammals.

Down-regulation of XIAP expression by antisense oligonucleotides has been shown to sensitize tumor cells to death induced by a wide range of pro-apoptotic agents, both in vitro and in vivo. SMAC/DIABLO-derived peptides have also been demonstrated to sensitize a number of different tumor induced select cell lines to undergo apoptosis as single agents, while other cell lines require an additional stimulus such as DR agonists or co-treatment with pro-apoptotic drugs. Because IAP inhibition appears to be a viable mechanism for promoting apoptosis and treating diseases and conditions that are sensitive to apoptosis, there is a continuing need to develop compounds that can inhibit IAP.

SUMMARY OF THE INVENTION

The present invention provides compounds, methods of modulating the activity of IAP, and methods for treating various medical conditions using such compounds.

The present invention also provides processes and intermediates for making the compounds of the present invention or stereoisomers, tautomers or pharmaceutically acceptable salts thereof.

The present invention also provides pharmaceutical compositions comprising a pharmaceutically acceptable carrier and one or more of the compounds of the present invention or stereoisomers, tautomers or pharmaceutically acceptable salts thereof.

The compounds of the invention may be used in the treatment and/or prophylaxis of multiple diseases or disorders associated with IAP inhibition, such as cancer and other maladies.

The compounds of the invention may be used in therapy.

The compounds of the invention may be used for the manufacture of a medicament for the treatment and/or prophylaxis of multiple diseases or disorders associated with IAP inhibition.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the invention provides a compound of Formula (I):

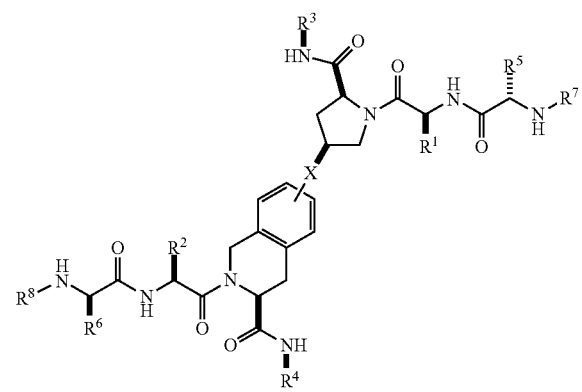

wherein:

X is a direct bond, —NH—, —O—, —NHCO— or —CONH—;

$R^1$ is optionally substituted alkyl, optionally substituted cycloalkyl or optionally substituted aryl;

$R^2$ is optionally substituted alkyl, optionally substituted cycloalkyl, optionally substituted thioalkyl, optionally substituted cycloalkylalkyl, optionally substituted heterocyclyl, optionally substituted arylalkyl or optionally substituted aryl;

$R^3$ and $R^4$ are independently optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;

$R^5$ and $R^6$ are independently hydrogen, optionally substituted alkyl or optionally substituted cycloalkyl;

$R^7$ and $R^8$ are independently hydrogen or optionally substituted alkyl;

or a pharmaceutically acceptable salt, tautomer or stereoisomer thereof.

In a second aspect, the invention provides a compound of Formula (Ia)

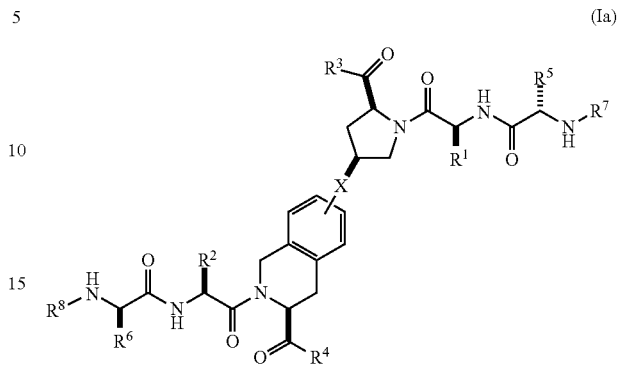

within the scope of the first aspect, wherein:

X is a direct bond, —NHCO— or —CONH—;

$R^1$ is optionally substituted alkyl;

$R^2$ is optionally substituted alkyl, optionally substituted cycloalkyl, optionally substituted cycloalkylalkyl, optionally substituted heterocyclyl or optionally substituted arylalkyl;

$R^3$ and $R^4$ are independently

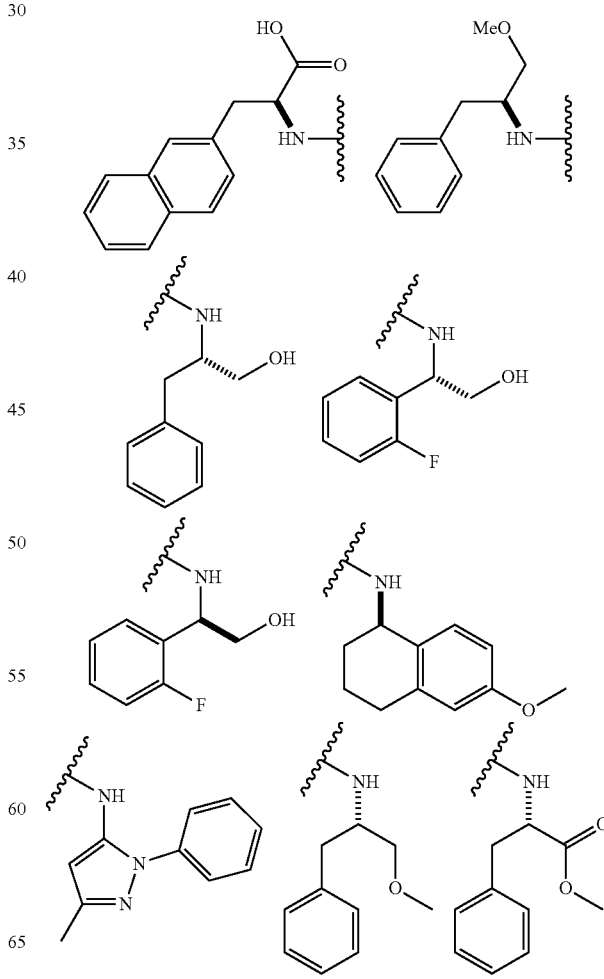

5
-continued
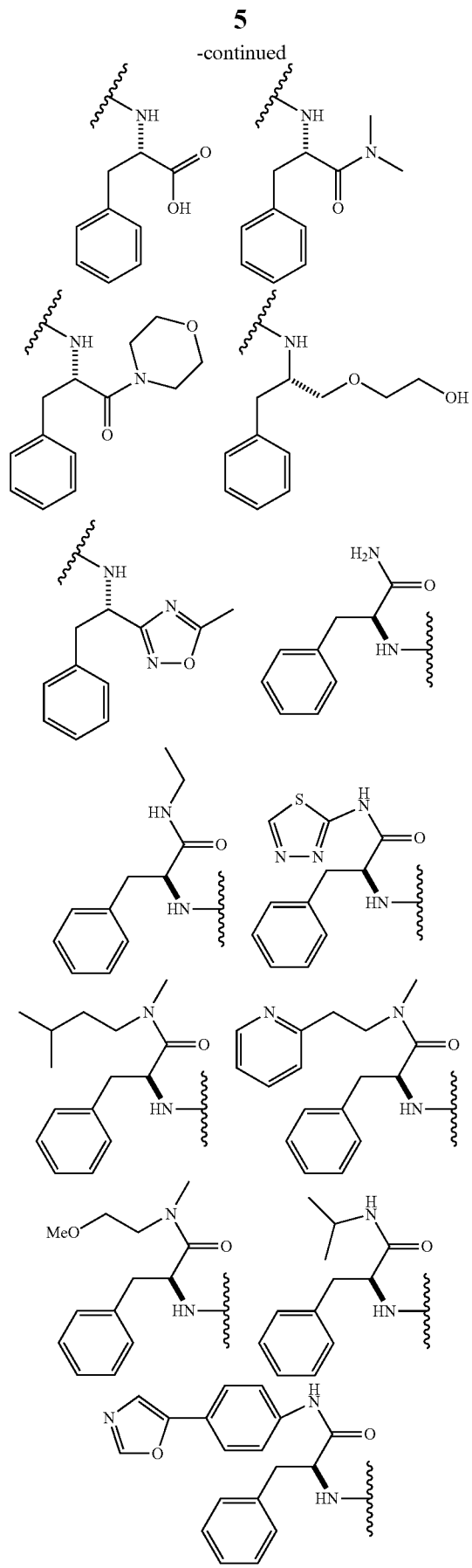
6
-continued
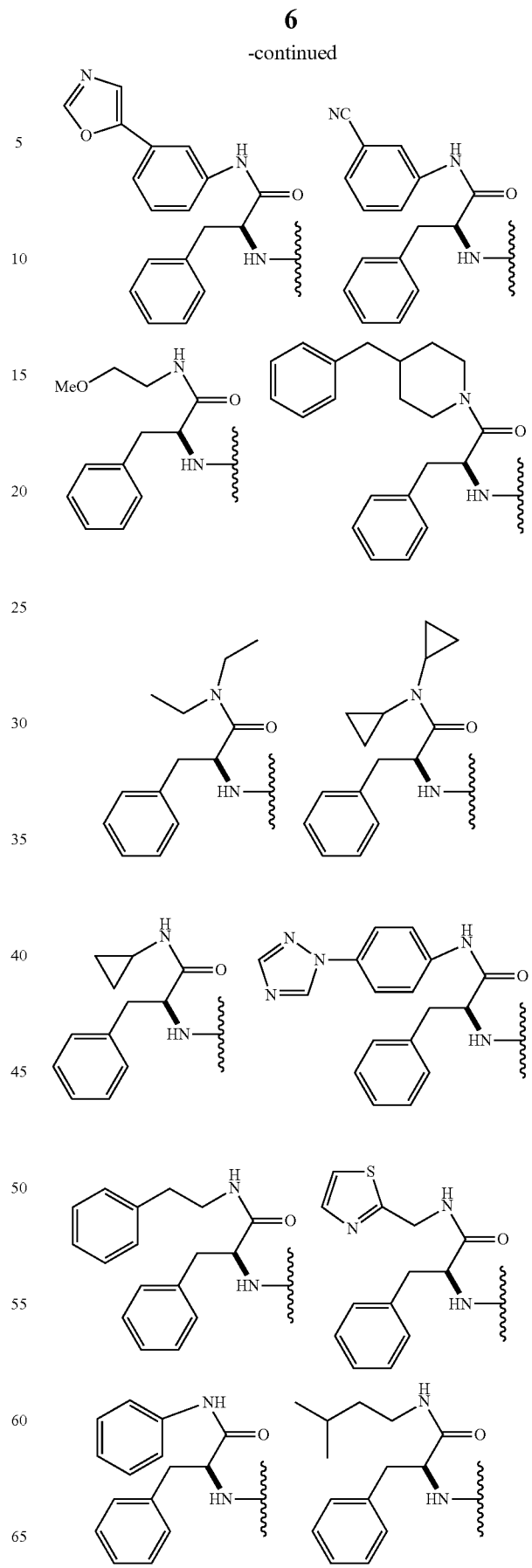

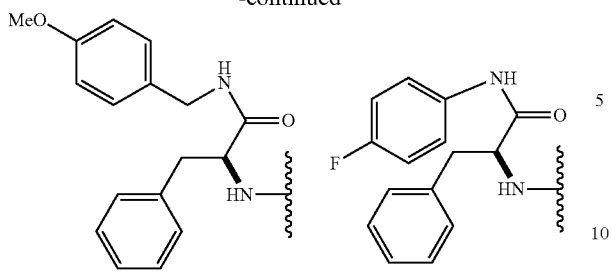
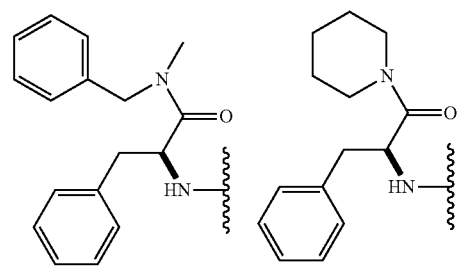
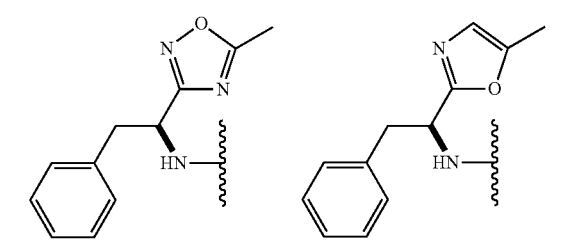
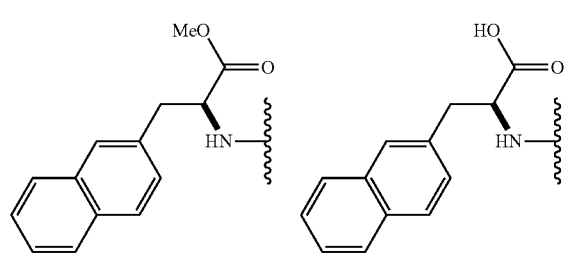

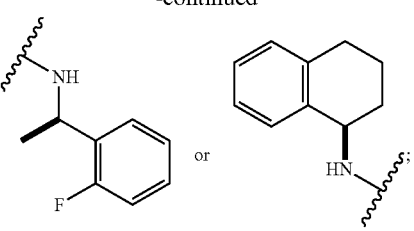

$R^5$ and $R^6$ are independently hydrogen, optionally substituted alkyl or optionally substituted cycloalkyl;

$R^7$ and $R^8$ are independently methyl or ethyl;

or a pharmaceutically acceptable salt, tautomer or stereoisomer thereof.

In a third aspect, the invention provides a compound of Formula (I)

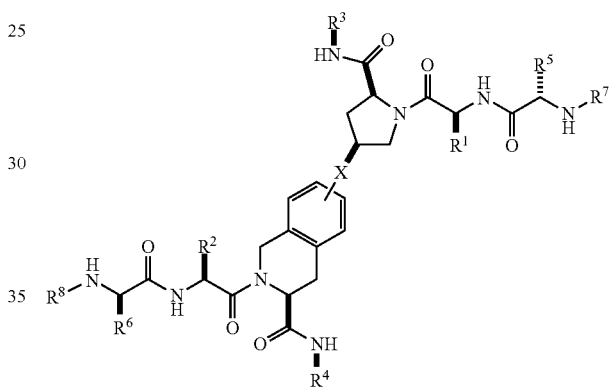

within the scope of the first aspect, wherein:

$R^1$ is alkyl;

$R^2$ is alkyl, cycloalkyl, cycloalkylalkyl, heterocyclyl or phenylalkyl, wherein the phenyl group is substituted with one or more alkyl or halogen groups;

$R^3$ and $R^4$ are independently optionally substituted alkyl, optionally substituted aryl, or optionally substituted arylalkyl;

or a pharmaceutically acceptable salt, tautomer or stereoisomer thereof.

In another aspect, the invention provides a compound of Formula (I) within the scope of the first, second or third aspect, wherein:

$R^1$ is t-butyl;

$R^2$ is alkyl, cycloalkyl, cycloalkylalkyl, tetrahydropyran or phenylalkyl, wherein the phenyl group is substituted with one or more fluoro groups;

$R^3$ is 1,2,3,4-tetrahydronaphthalenyl;

$R^4$ is 1,2,3,4-tetrahydronaphthalenyl or optionally substituted arylalkyl; wherein said aryl group of the arylalkyl is substituted with alkyl or halogen;

or a pharmaceutically acceptable salt, tautomer or stereoisomer thereof.

In another aspect, the invention provides a compound of Formula (II)

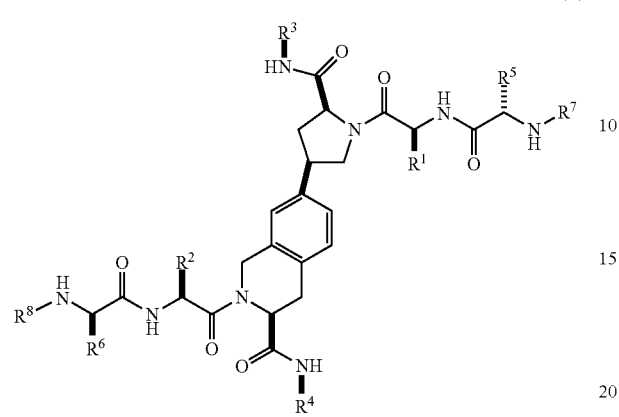

(II)

wherein:

R$^1$ is optionally substituted alkyl;

R$^2$ is optionally substituted alkyl, optionally substituted cycloalkyl, optionally substituted cycloalkylalkyl, optionally substituted heterocyclyl or optionally substituted arylalkyl;

R$^3$ and R$^4$ are independently optionally substituted alkyl, optionally substituted aryl, or optionally substituted arylalkyl;

R$^5$ and R$^6$ are independently hydrogen, optionally substituted alkyl or optionally substituted cycloalkyl;

R$^7$ and R$^8$ are independently methyl or ethyl;

or a pharmaceutically acceptable salt, tautomer or stereoisomer thereof.

In another aspect, the invention provides a compound of Formula (II)

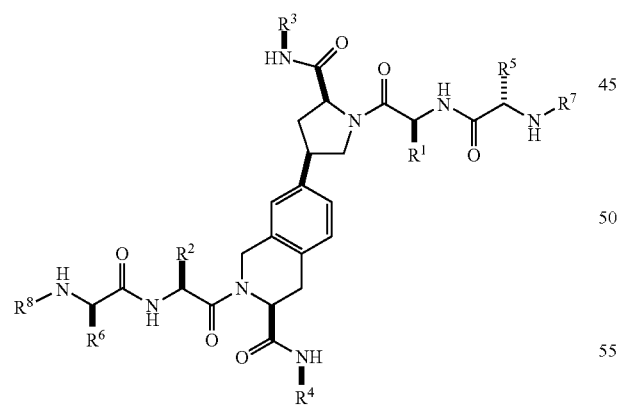

(II)

wherein:

R$^1$ is optionally substituted alkyl;

R$^2$ is optionally substituted alkyl, optionally substituted cycloalkyl, optionally substituted cycloalkylalkyl, optionally substituted heterocyclyl or optionally substituted arylalkyl;

R$^3$ and R$^4$ are independently optionally substituted alkyl, optionally substituted aryl, or optionally substituted arylalkyl;

R$^5$ and R$^6$ are independently hydrogen, optionally substituted alkyl or optionally substituted cycloalkyl;

R$^7$ and R$^8$ are independently methyl or ethyl;

or a pharmaceutically acceptable salt, tautomer or stereoisomer thereof.

In another aspect, the invention provides a compound of Formula (IIa)

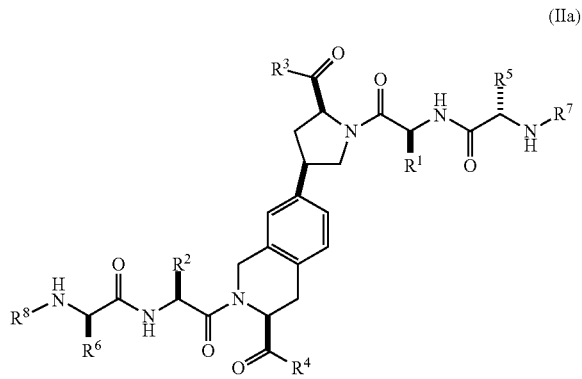

(IIa)

wherein:

R$^1$ is optionally substituted alkyl;

R$^2$ is optionally substituted alkyl, optionally substituted cycloalkyl, optionally substituted thioalkyl, optionally substituted cycloalkylalkyl, optionally substituted heterocyclyl or optionally substituted arylalkyl;

R$^3$ and R$^4$ are independently

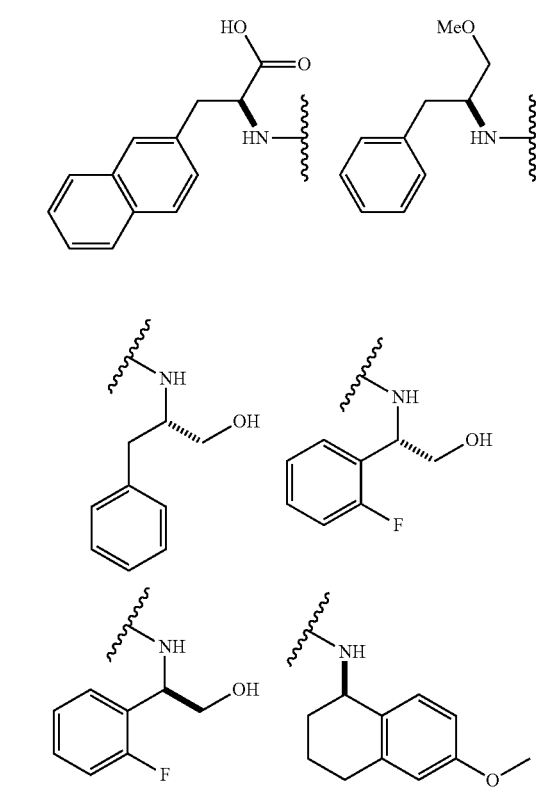

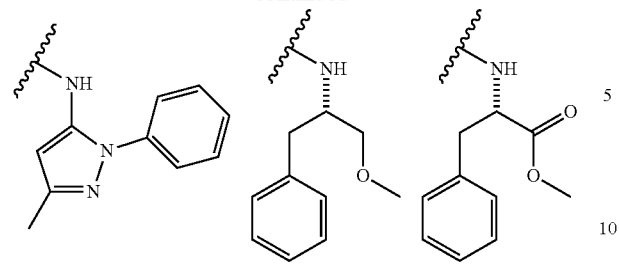
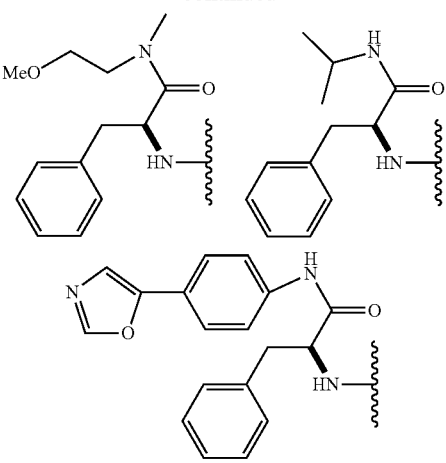
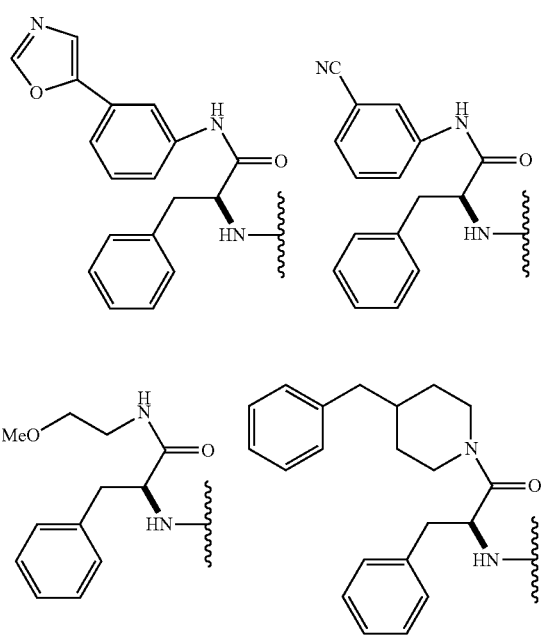

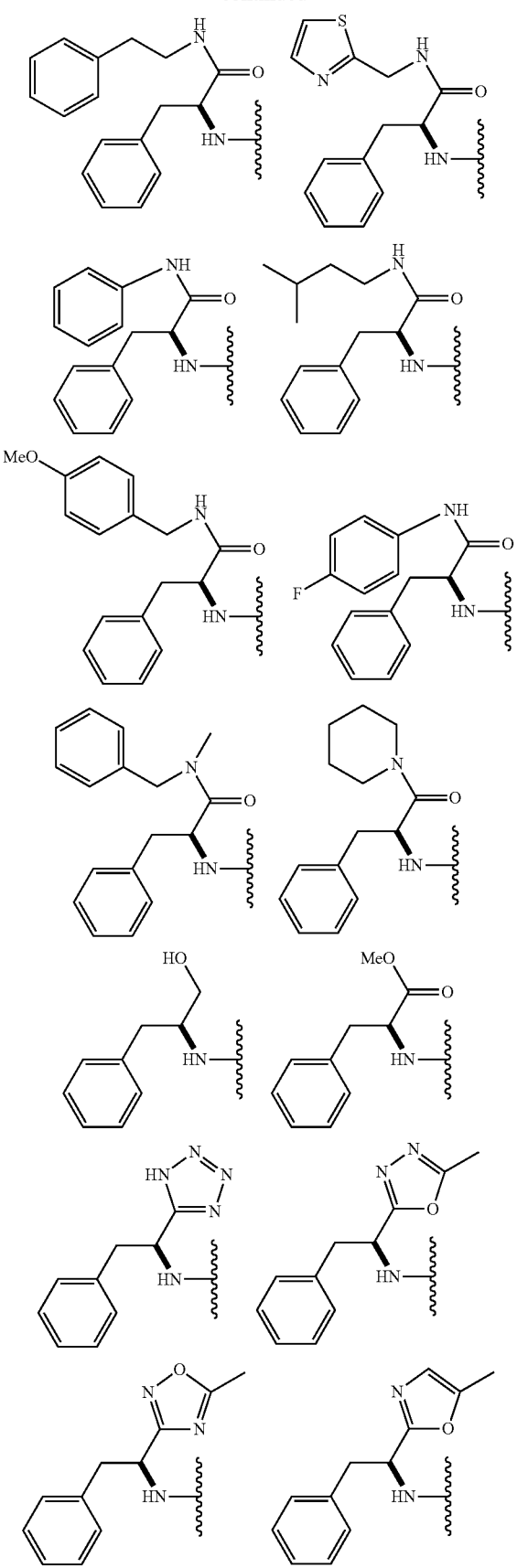

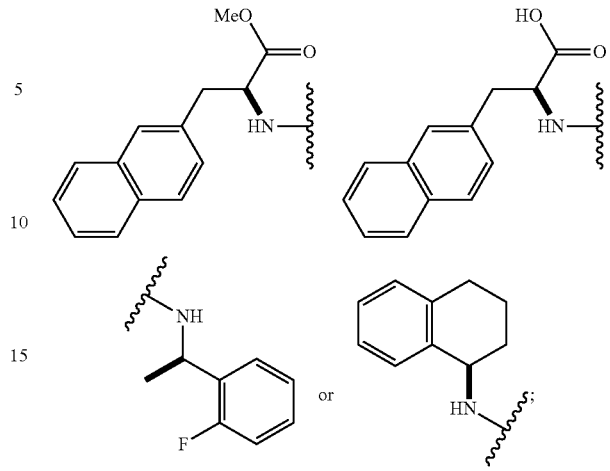

$R^5$ and $R^6$ are independently hydrogen, optionally substituted alkyl or optionally substituted cycloalkyl;

$R^7$ and $R^8$ are independently methyl or ethyl;

or a pharmaceutically acceptable salt, tautomer or stereoisomer thereof.

In another aspect, the invention provides a compound of Formula (IIa)

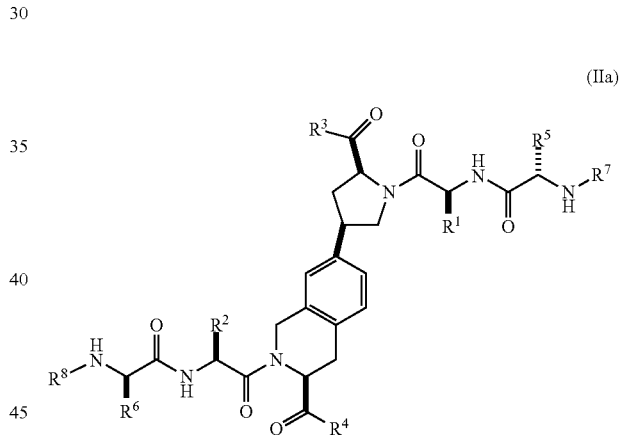

(IIa)

wherein:

$R^1$ and $R^2$ are independently optionally substituted alkyl;

$R^3$ and $R^4$ are independently

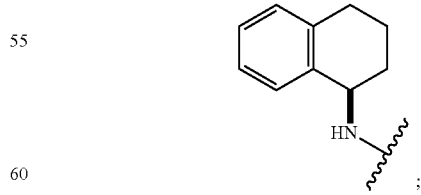

;

$R^5$ and $R^6$ are independently methyl or ethyl;

$R^7$ and $R^8$ are independently methyl or ethyl;

or a pharmaceutically acceptable salt, tautomer or stereoisomer thereof.

In another aspect, the invention provides a compound of Formula (III)

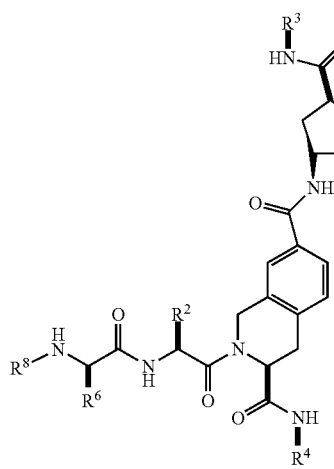

wherein:

R¹ is optionally substituted alkyl;

R² is optionally substituted alkyl, optionally substituted cycloalkyl, optionally substituted cycloalkylalkyl, optionally substituted heterocyclyl or optionally substituted arylalkyl;

R³ and R⁴ are independently optionally substituted alkyl, optionally substituted aryl, or optionally substituted arylalkyl;

R⁵ and R⁶ are independently hydrogen, optionally substituted alkyl or optionally substituted cycloalkyl;

R⁷ and R⁸ are independently optionally substituted alkyl;

or a pharmaceutically acceptable salt, tautomer or stereoisomer thereof.

In another aspect, the invention provides a compound selected from the exemplified examples within the scope of the first aspect, or a pharmaceutically acceptable salt, tautomer or stereoisomer thereof.

In another aspect, the invention provides a compound selected from any subset list of compounds within the scope of any of the above aspects.

In one embodiment, X is a direct bond, —O—, —NH— or —CONH—;

In another embodiment, X is a direct bond or —CONH—;

In another embodiment, X is a direct bond;

In another embodiment, X is —CONH—;

In another embodiment, R¹ is t-butyl.

In another embodiment, R² is alkyl, cycloalkyl, cycloalkylalkyl, heterocyclyl or phenylalkyl, wherein the phenyl group is substituted with one or more alkyl or halogen groups.

In another embodiment, R² is t-butyl.

In another embodiment, R² is tetrahydropyran.

In another embodiment, R³ and R⁴ are independently 1,2,3,4-tetrahydronaphthalenyl.

In another embodiment, R³ and R⁴ are independently

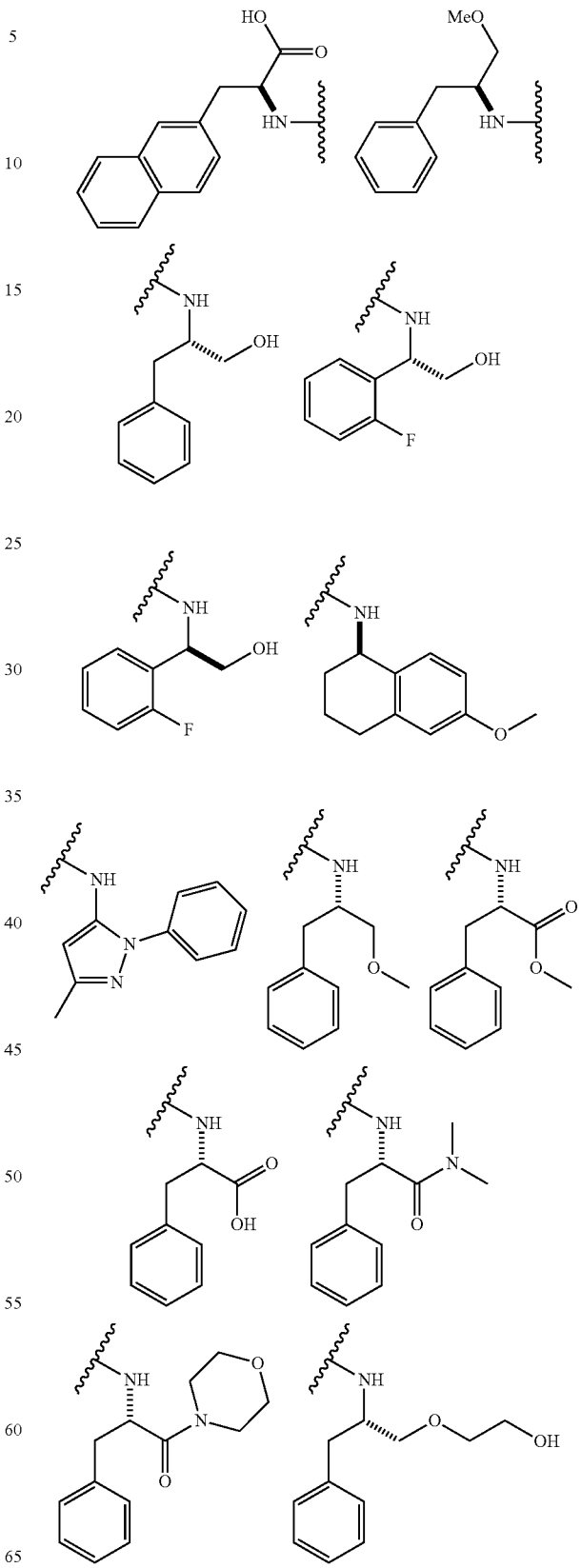

-continued
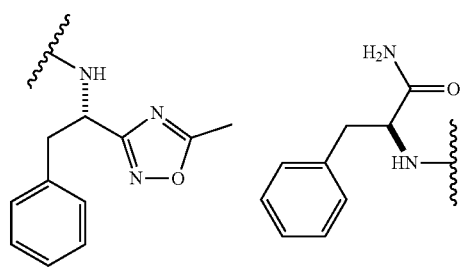
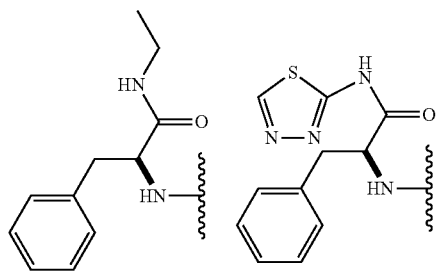
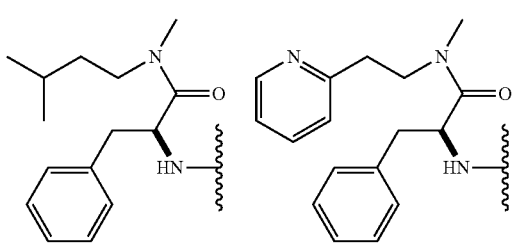
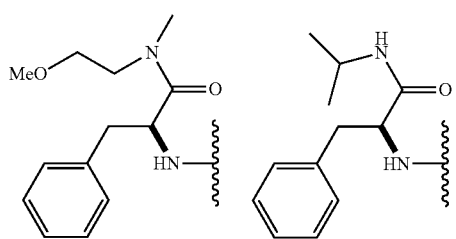
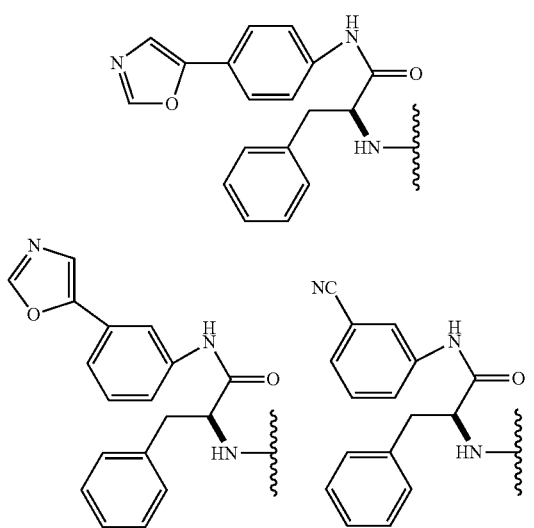
-continued
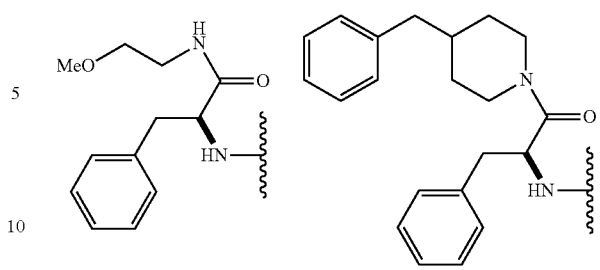
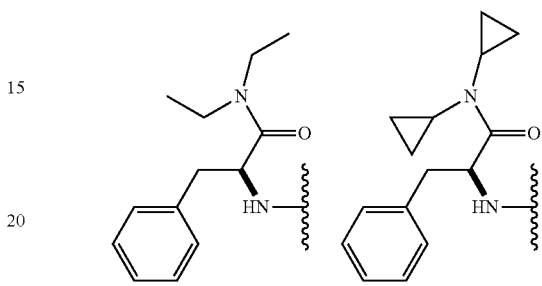
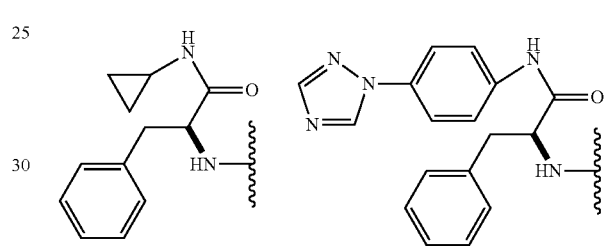
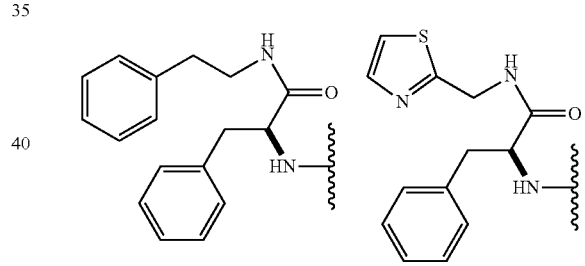
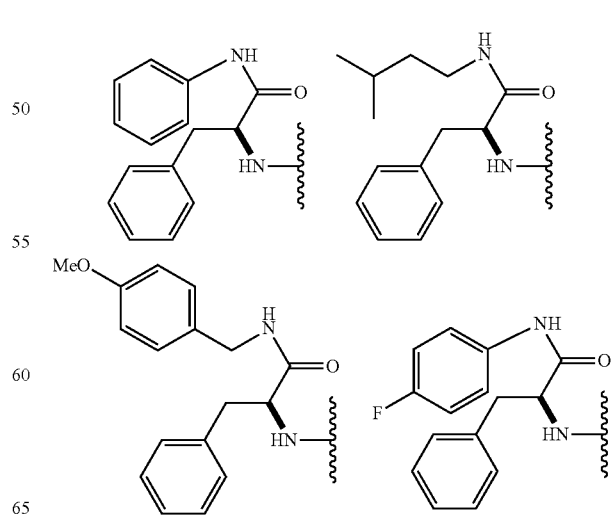

-continued

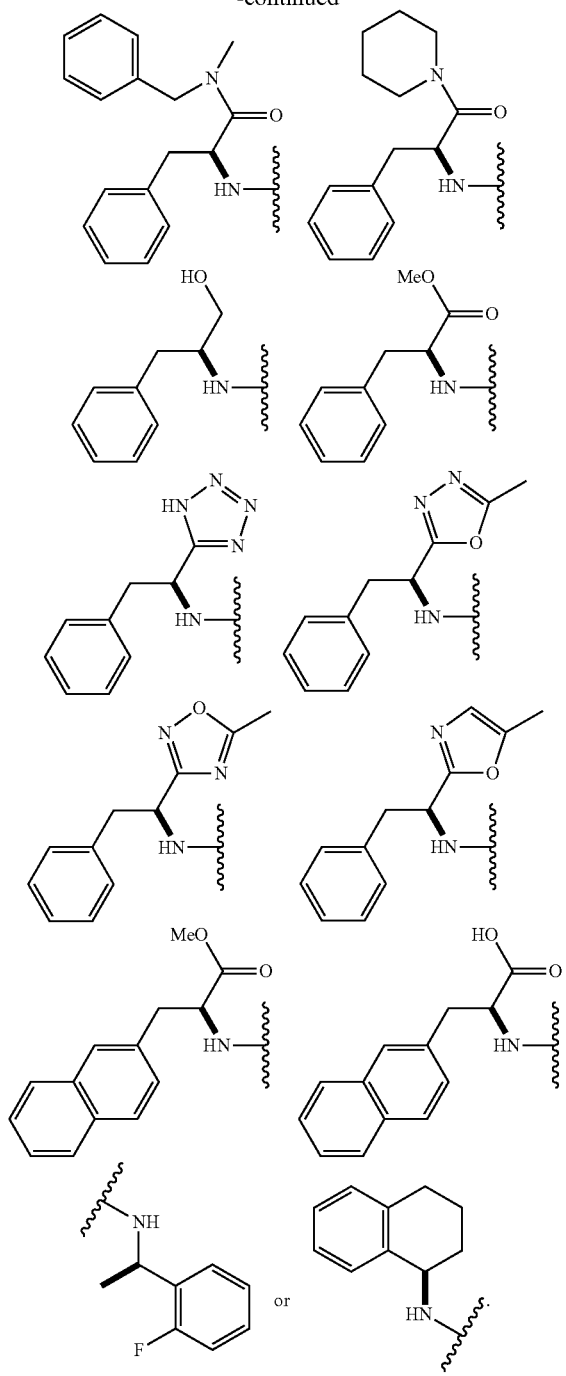

In another embodiment, R⁵ and R⁶ independently hydrogen, methyl, butyl or cyclopropyl.

In another embodiment, $R^7$ and $R^8$ are independently methyl or ethyl.

In another embodiment, the compounds of the invention have BIR3 $IC_{50}$ values ≤0.20.

In another embodiment, the compounds of the invention have BIR3 $IC_{50}$ values ≤0.07.

In another embodiment, the compounds of the invention have BIR3 $IC_{50}$ values ≤0.02.

In another embodiment, the compounds of the invention have BIR3 $IC_{50}$ values ≤0.005.

In another embodiment, the compounds of the invention have BIR2-3 $IC_{50}$ values ≤0.25.

In another embodiment, the compounds of the invention have BIR2-3 $IC_{50}$ values ≤0.05.

In another embodiment, the compounds of the invention have BIR2-3 $IC_{50}$ values ≤0.01.

In another embodiment, the compounds of the invention have BIR2-3 $IC_{50}$ values ≤0.005.

II. Other Embodiments of the Invention

In another embodiment, the present invention provides a composition comprising one or more compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a method for the treatment and/or prophylaxis of various types of cancer, comprising administering to a patient in need of such treatment and/or prophylaxis a therapeutically effective amount of one or more compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with the inhibition of apoptosis.

In another aspect, the invention provides a method of treating a patient suffering from or susceptible to a medical condition that is sensitive to apoptosis. A number of medical conditions can be treated. The method comprises administering to the patient a therapeutically effective amount of a composition comprising a compound described herein. For example, the compounds described herein may be used to treat or prevent infections, proliferative diseases (e.g., cancer), and autoimmune diseases.

In another aspect, the invention provides a method of inhibiting the activity of an IAP in a cell, thus promoting apoptosis. The method comprises exposing the cell to a compound described herein.

III. Therapeutic Applications

The compounds and pharmaceutical compositions of the present invention are useful in treating or preventing any disease or conditions that are sensitive to apoptosis. These include infections (e.g., skin infections, GI infection, urinary tract infections, genito-urinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the animal. In certain embodiments, the compound or pharmaceutical composition is administered orally. In other embodiments, the compound or pharmaceutical composition is administered parenterally.

In one embodiment, the compounds of this invention can be used for the treatment of any cancer type that fails to undergo apoptosis in a patient. This includes, but is not limited to: solid tumors, including but not limited to carcinomas; sarcomas including Kaposi's sarcoma; erythroblastoma; glioblastoma; meningioma; astrocytoma; melanoma; and myoblastoma. Treatment or prevention of non-solid tumor cancers, such as leukemia, is also contemplated by this invention.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

Compounds of the invention are useful for sensitizing cells to apoptotic signals. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

IV. Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

V. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g., —SO$_2$NH$_2$, substituted sulfonamido, nitro, cyano, carboxy, carbamyl, e.g., —CONH$_2$, substituted carbamyl e.g., —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl.

For purposes of clarity and in accordance with standard convention in the art, the symbol

is used in formulas and tables to show the bond that is the point of attachment of the moiety or substituent to the core/nucleus of the structure.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkoxy" or "alkyloxy" refers to an —O-alkyl group. "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and terahydronaphthyl. The fused aryls may be connected to another group either at a suitable position on the cycloalkyl ring or the aromatic ring. For example:

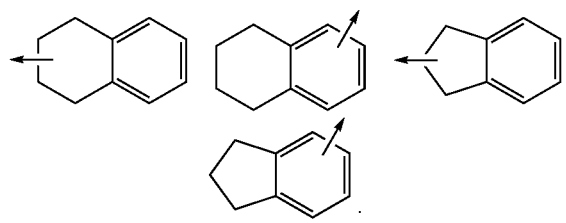

Arrowed lines drawn from the ring system indicate that the bond may be attached to any of the suitable ring atoms.

The term "cycloalkyl" refers to cyclized alkyl groups. C$_{3-10}$ cycloalkyl is intended to include C$_3$, C$_4$, C$_5$, C$_7$, C$_8$, C$_9$ and C$_{10}$ cycloalkyl groups. Example cycloalkyl groups include, but are not limited to, cyclopropyl, cyclobutyl, cyclopentyl, cyclohexyl, norbornyl and adamantyl. Branched cycloalkyl groups such as 1-methylcyclopropyl and 2-methylcyclopropyl are included in the definition of "cycloalkyl".
The term "cycloalkenyl" refers to cyclized alkenyl groups. C$_{4-6}$ cycloalkenyl is intended to include C$_4$, C$_5$, and C$_6$ cycloalkenyl groups. Example cycloalkenyl groups include, but are not limited to, cyclobutenyl, cyclopentenyl, and cyclohexenyl.

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

As used herein, the term "heterocycle", "heterocyclyl", "or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen.

Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWG include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O-heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a di-substituted hydrazine, R4-M and R7-M, a nucleophile, a hydrazine reducing agent, an activator, a strong base, a hindered amine base and a cyclizing agent. Such amine protecting groups fitting these criteria include those listed in Greene et al., *Protective Groups in Organic Synthesis*, John Wiley & Sons, New York (1991) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C═C, C═N, or N═N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (NO) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in

*Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112: 309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);
c) Bundgaard, H., *Adv. Drug Deliv. Rev.,* 8:1-38 (1992);
d) Bundgaard, H. et al., *J. Pharm. Sci.,* 77:285 (1988); and
e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "therapeutically effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Certain compounds of Formula I may generally be prepared according to the following Schemes 1-13. Tautomers and solvates (e.g., hydrates) of the compounds of Formula I are also within the scope of the present invention. Methods of solvation are generally known in the art. Accordingly, the compounds of the instant invention may be in the free or hydrate form, and may be obtained by methods exemplified by the following schemes.

General routes to analogues described in the invention are illustrated in Schemes 1-13. The tetrahydroisoquinoline carboxylic acid coupling partner 10 can be prepared as shown in Scheme 1. Pictet-Spengler cyclization of 3,5-diiodotyrosine 1 with formaldehyde and subsequent catalytic hydrogenation provides derivative 2. Conversion to the amide intermediate 4 can occur through a two-step procedure employing a coupling reagent, such as EDC, after protection of the secondary amine with Boc-anhydride. Aryl triflate formation, followed by palladium-catalyzed methoxycarbonylation then provides intermediate 5. Following deprotection of the t-butyl carbamate under acidic conditions (e.g., TFA), the secondary amine can be treated with various N-protected amino acids 6 in the presence of a coupling reagent, such as EDC, to furnish intermediate 7. Primary amine formation can be achieved using conditions dependent on the nature of PG. For example, removal of Fmoc can occur using basic conditions (e.g., piperidine), while acidic conditions such as TFA cleaves a Boc-protected amine Amide formation in the presence of a coupling reagent, such as EDC, can be followed by hydrolysis to provide the carboxylic acid coupling partners 10.

Scheme 1

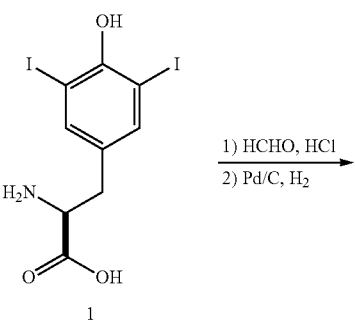

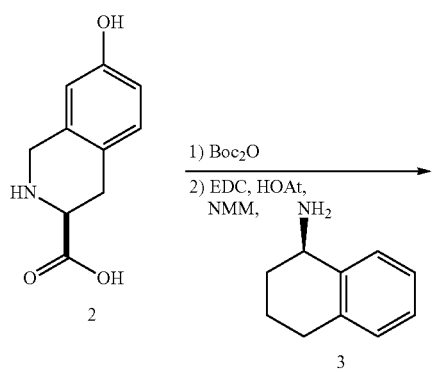

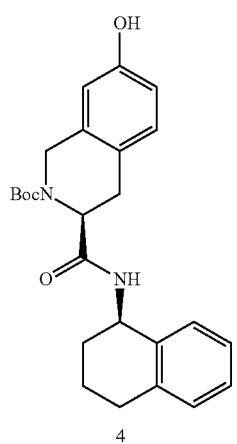

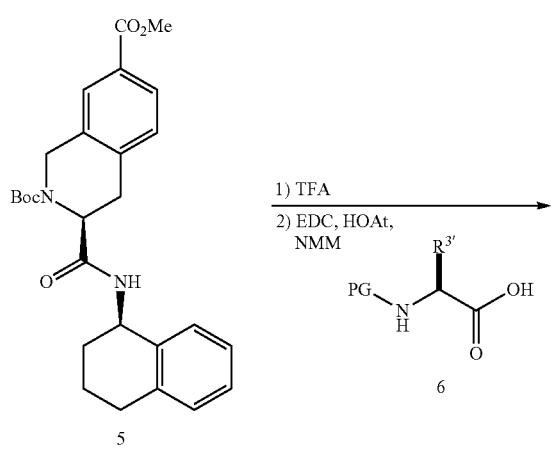

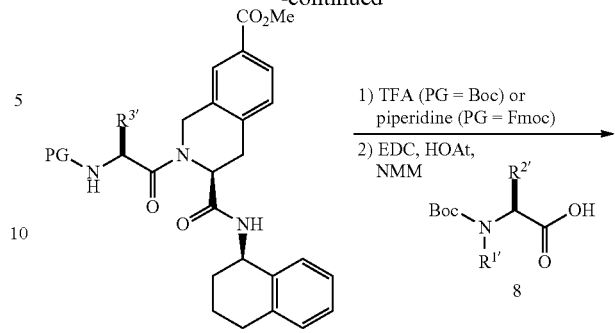

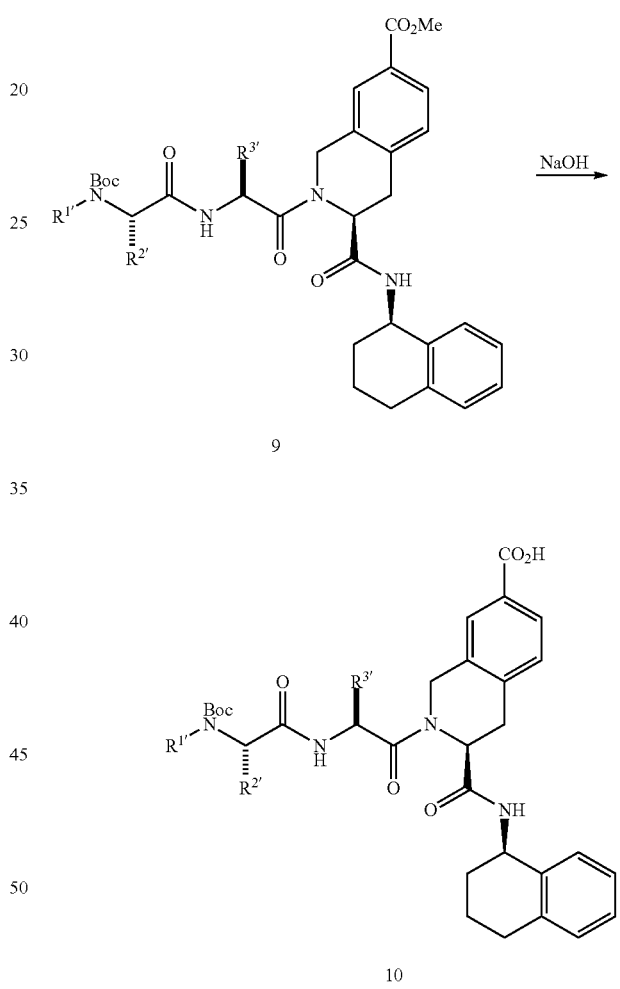

Linear heterodimeric compounds 18 can be prepared through the coupling of carboxylic acids 10 and aminoproline analogues 17 as outlined in Scheme 2. Fmoc-protected aminoproline 11 can be converted into amide intermediate 12 by employing a coupling reagent, such as EDC. Conversion to the elaborated intermediate 17 can be accomplished using chemistry described in Scheme 1, and removal of the Fmoc protecting group under basic conditions (e.g., piperidine). Synthesis of the heterodimeric analogues 18 can occur through a two-step procedure employing carboxylic acids 10 and a coupling reagent, such as EDC, followed by removal of the Boc carbamates under acidic conditions (e.g., TFA).

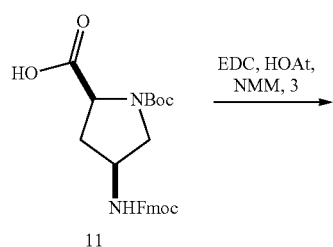

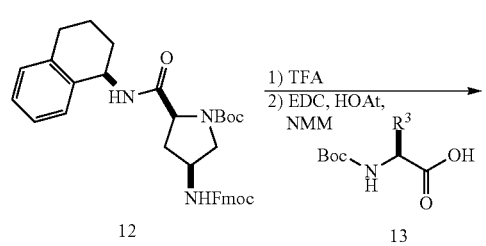

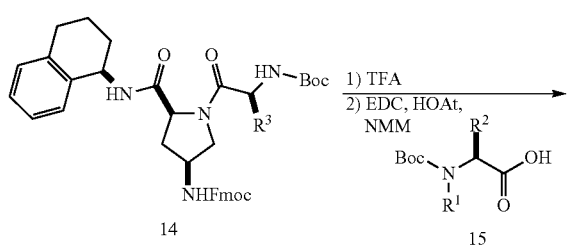

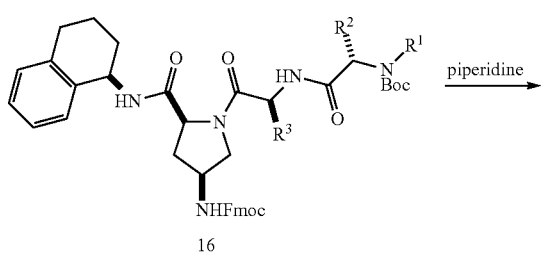

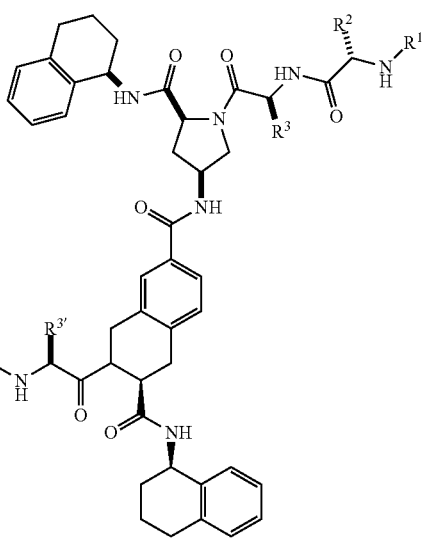

Alternatively, linear heterodimeric compounds 18 can be furnished through the sequence outlined in Scheme 3. Coupling of Cbz-protected aminoproline and carboxylic acids 10 can be accomplished in the presence of a coupling reagent, such as EDC, to provide intermediate 20. Hydrolysis of the methyl ester and conversion to the amide in the presence of a coupling reagent, such as EDC, can be followed by hydrogenolysis with palladium hydroxide on carbon to afford secondary amine 22. Conversion to the linear heterodimeric analogues 18 can be accomplished using chemistry described in Scheme 2.

Scheme 3

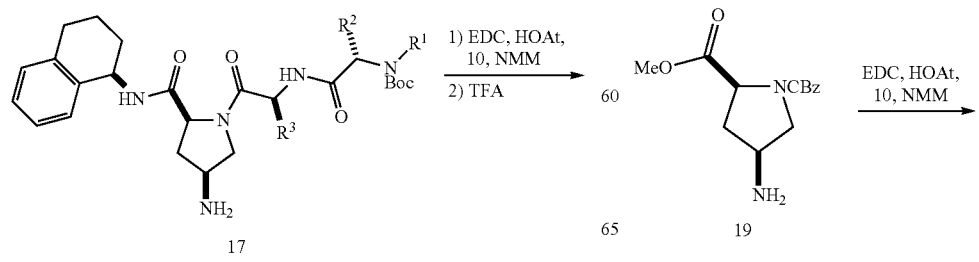

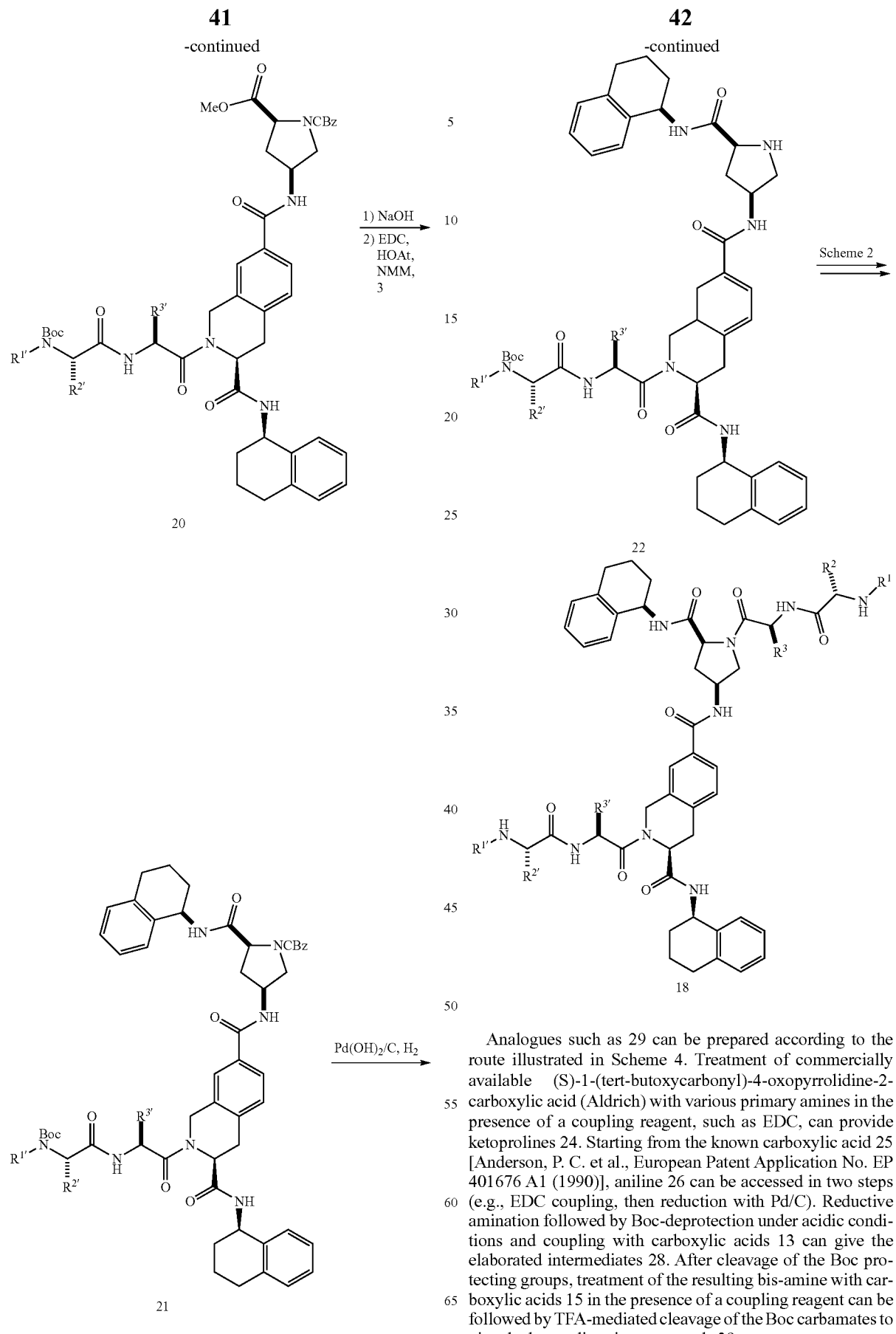

Analogues such as 29 can be prepared according to the route illustrated in Scheme 4. Treatment of commercially available (S)-1-(tert-butoxycarbonyl)-4-oxopyrrolidine-2-carboxylic acid (Aldrich) with various primary amines in the presence of a coupling reagent, such as EDC, can provide ketoprolines 24. Starting from the known carboxylic acid 25 [Anderson, P. C. et al., European Patent Application No. EP 401676 A1 (1990)], aniline 26 can be accessed in two steps (e.g., EDC coupling, then reduction with Pd/C). Reductive amination followed by Boc-deprotection under acidic conditions and coupling with carboxylic acids 13 can give the elaborated intermediates 28. After cleavage of the Boc protecting groups, treatment of the resulting bis-amine with carboxylic acids 15 in the presence of a coupling reagent can be followed by TFA-mediated cleavage of the Boc carbamates to give the heterodimeric compounds 29.

Related compounds 34 can be prepared as depicted in Scheme 5. Commercially available (2S,4R)-1-tert-butyl 2-methyl 4-hydroxypyrrolidine-1,2-dicarboxylate (30, Aldrich) and hydroxy-tetrahydroisoquinoline 31 (prepared according to Scheme 1) can undergo Mitsunobu coupling with ADDP and PPh$_3$ to give 32. Following hydrolysis under basic conditions (e.g., NaOH), treatment with various primary amines in the presence of a coupling reagent, such as EDC, gives the bis-amide intermediate 33. Elaboration to the final compounds 34 can be achieved as previously described in Scheme 4 (i.e., 27→29).

Scheme 6

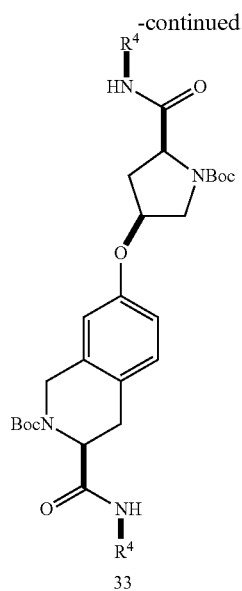

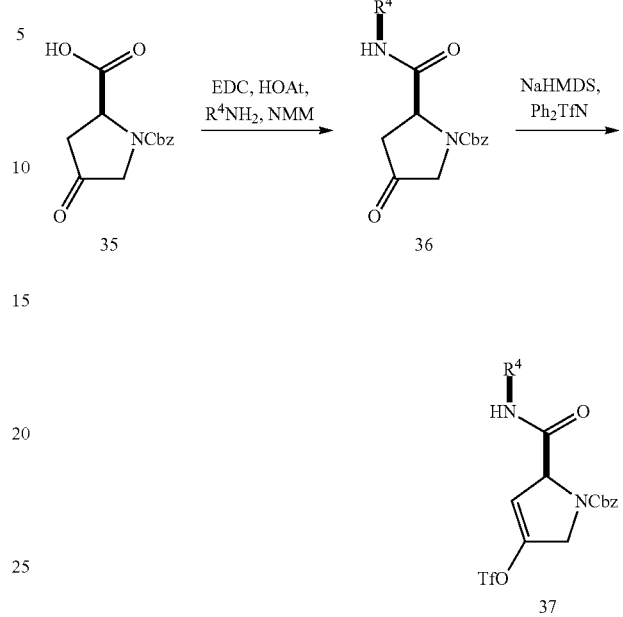

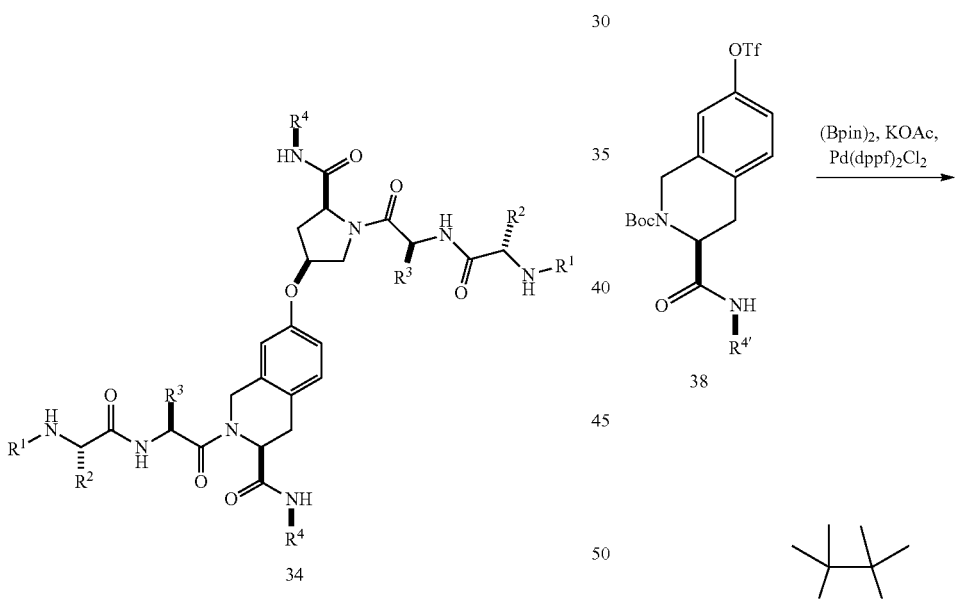

Analogues such as 42 ($R^3$=$R^{3'}$) can be accessed using the route described in Scheme 6. Coupling of commercially available (S)-1-((benzyloxy)carbonyl)-4-oxopyrrolidine-2-carboxylic acid (35, Aldrich) with a primary amine in the presence of, for example, EDC can give keto-prolines 36. Conversion to enol triflate 37 can then be accomplished using NaHMDS and Ph₂TfN. Aryl triflate 38 (prepared according to Scheme 1) can be converted to boronate ester 39, which can undergo Suzuki coupling with 37 to give the unsaturated intermediate 40. Simultaneous reduction of the olefin and cleavage of the Cbz-protecting group can occur using Pd(OH)$_2$ in the presence of H$_2$. Intermediate 41 can then be converted to fully elaborated compounds 42 following the chemistry depicted in Scheme 4.

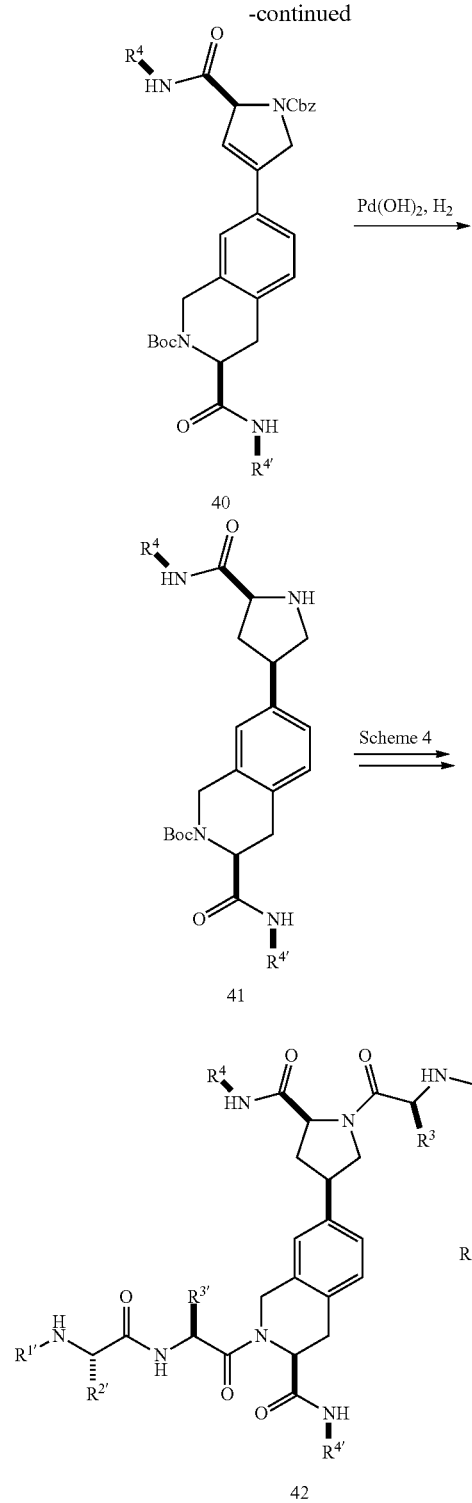
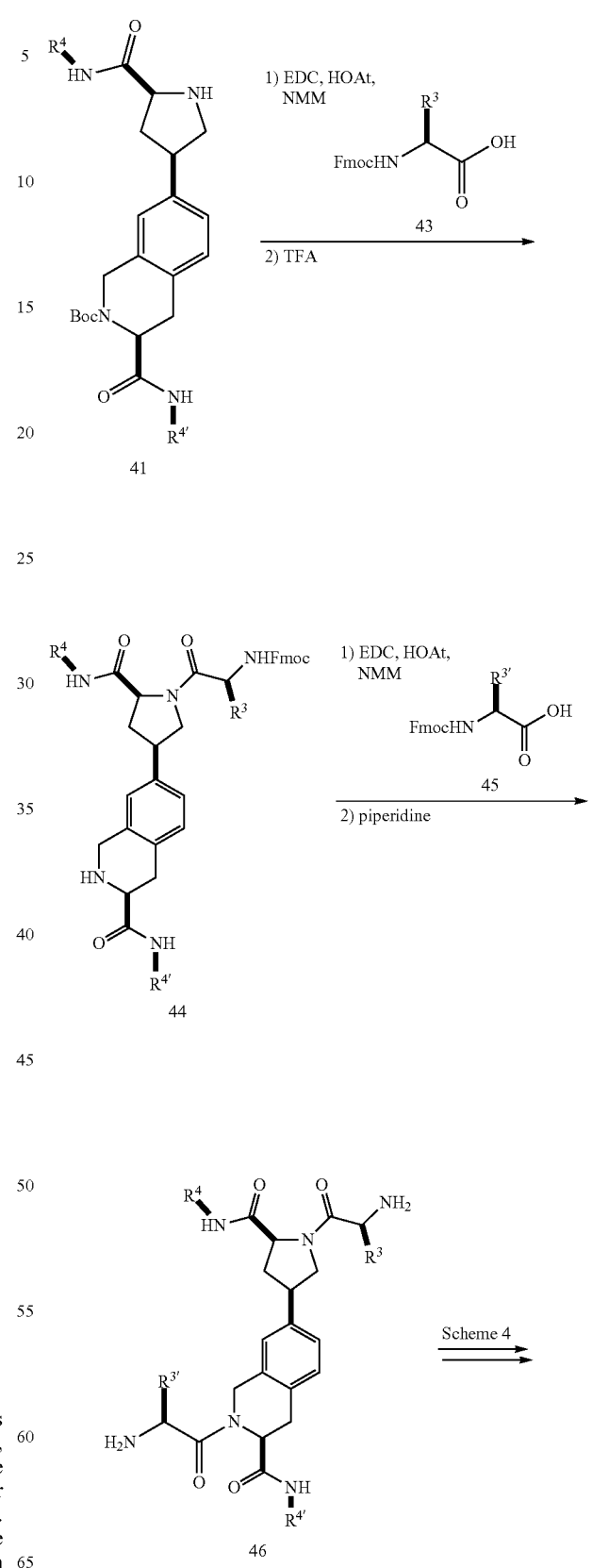

Scheme 7

When R³≠R³', an alternative route to compound 42 is employed (Scheme 7). From intermediate 41 (Scheme 6), coupling with Fmoc-N-protected carboxylic acids 43 can be followed by selective removal of the Boc carbamate under acidic conditions (e.g., TFA) to give the secondary amine 44. Subsequent amide formation followed by cleavage of the Fmoc-protecting groups using, for example, piperidine can give the bis-amine 46, which is converted to the final analogues 42 as previously shown in Scheme 4.

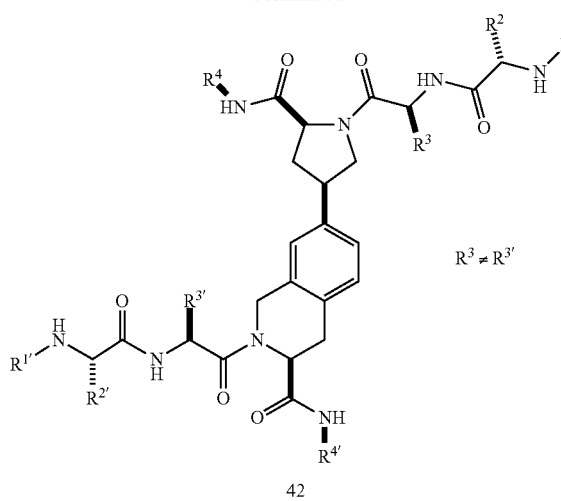

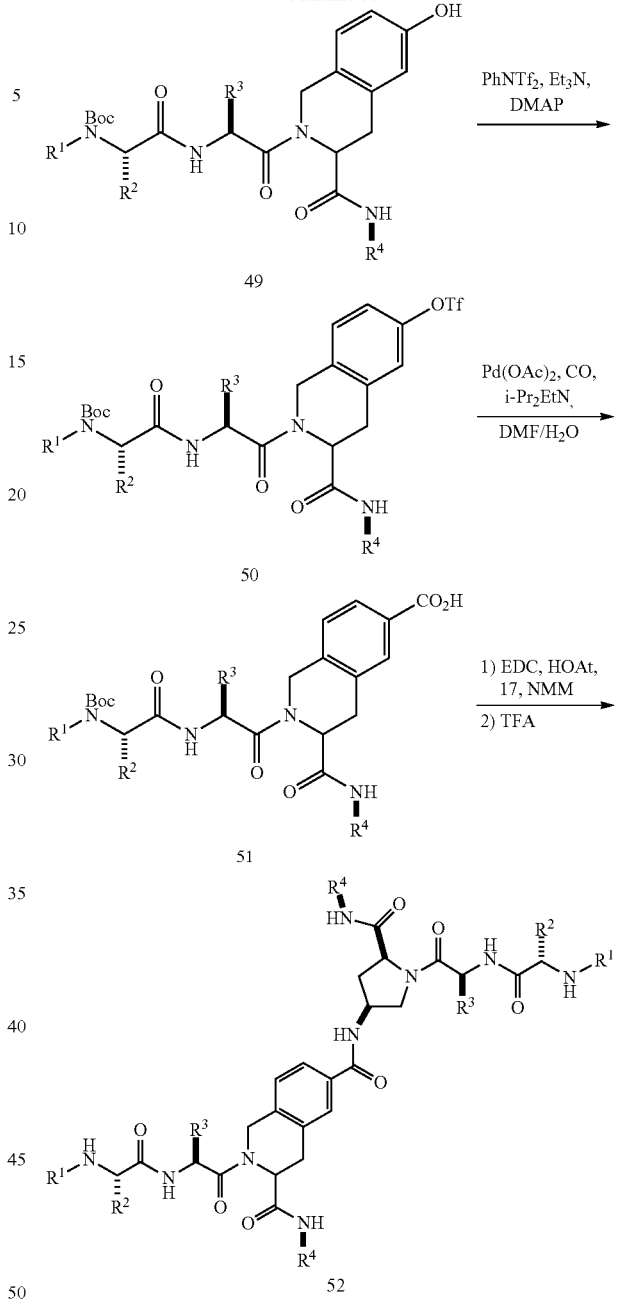

Analogues such as 52 can be accessed according to the route shown in Scheme 8. Commercially available (±)-6-hydroxy-1,2,3,4-tetrahydroisoquinoline-3-carboxylic acid (Aldrich) can undergo Boc-protection, followed by amide formation in the presence of a coupling reagent and then acid-mediated cleavage of the Boc carbamate to give racemic amine 48. Following the sequence outlined in Scheme 1, 48 can be elaborated to phenol 49. After conversion to the aryl triflate, palladium-catalyzed carbonylation can provide the carboxylic acid coupling partner 51. Exposure to aminoproline intermediate 17 and a coupling reagent, such as EDC, can provide compound 52 after global Boc-deprotection.

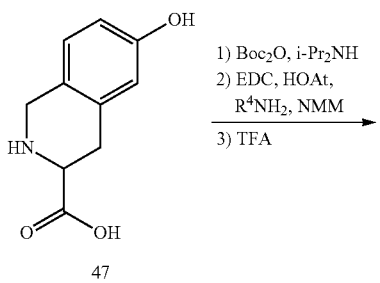

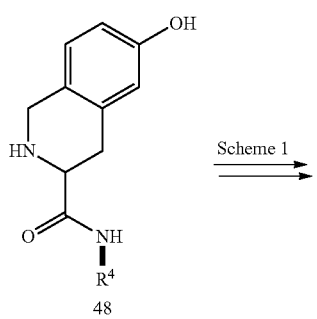

β-Thiovaline derivatives such as 61 and 62 can be accessed using the routes shown below in Scheme 9. Boc-protection of commercially available (R)-2-amino-3-mercapto-3-methylbutanoic acid (53, Aldrich) can be followed by reaction with methyl bromoacetate to give 55. Intermediate 41 (Scheme 6) can undergo coupling with Cbz-protected amino acid 56 followed by selective removal of the Boc-group under acidic conditions. Coupling with carboxylic acid 55 using, for example, HATU can be followed by cleavage of the Cbz-protecting groups with Pd(OH)$_2$ in the presence of H$_2$. Treatment of the resulting bis-amine with amino acid 15 in the presence of a coupling reagent and then hydrolysis of the methyl ester can give 59. TFA-mediated cleavage of the Boc carbamates provides 60. Alternatively, the carboxylic acid of 59 can be reduced using CDI and NaBH$_4$ to give primary alcohol 61 after treatment with TFA. Intermediate 59 can be further elaborated by coupling with various amines to provide, after global Boc-deprotection, amides 62.

Scheme 9
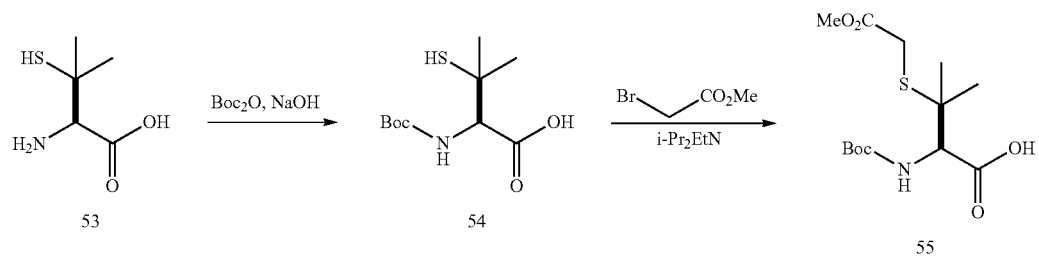
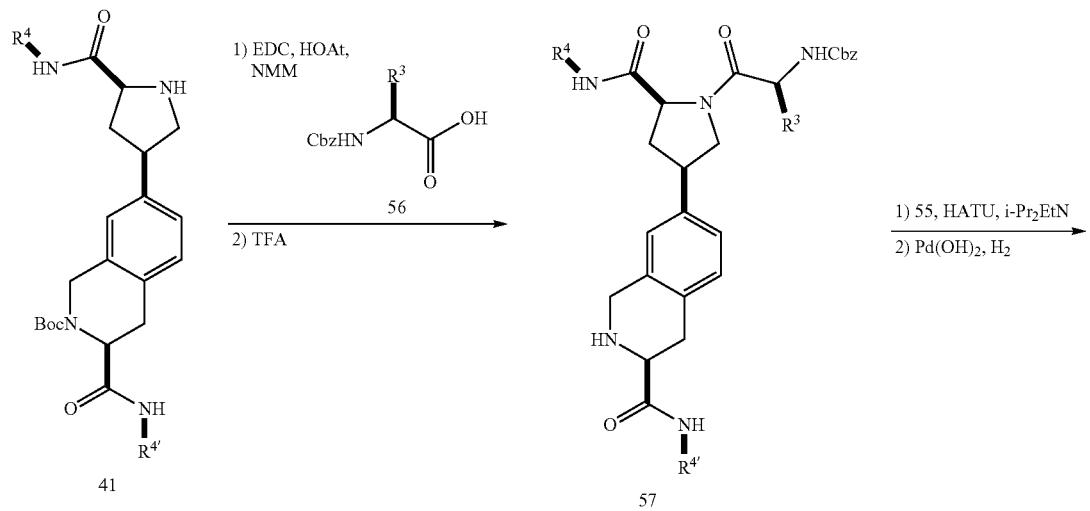

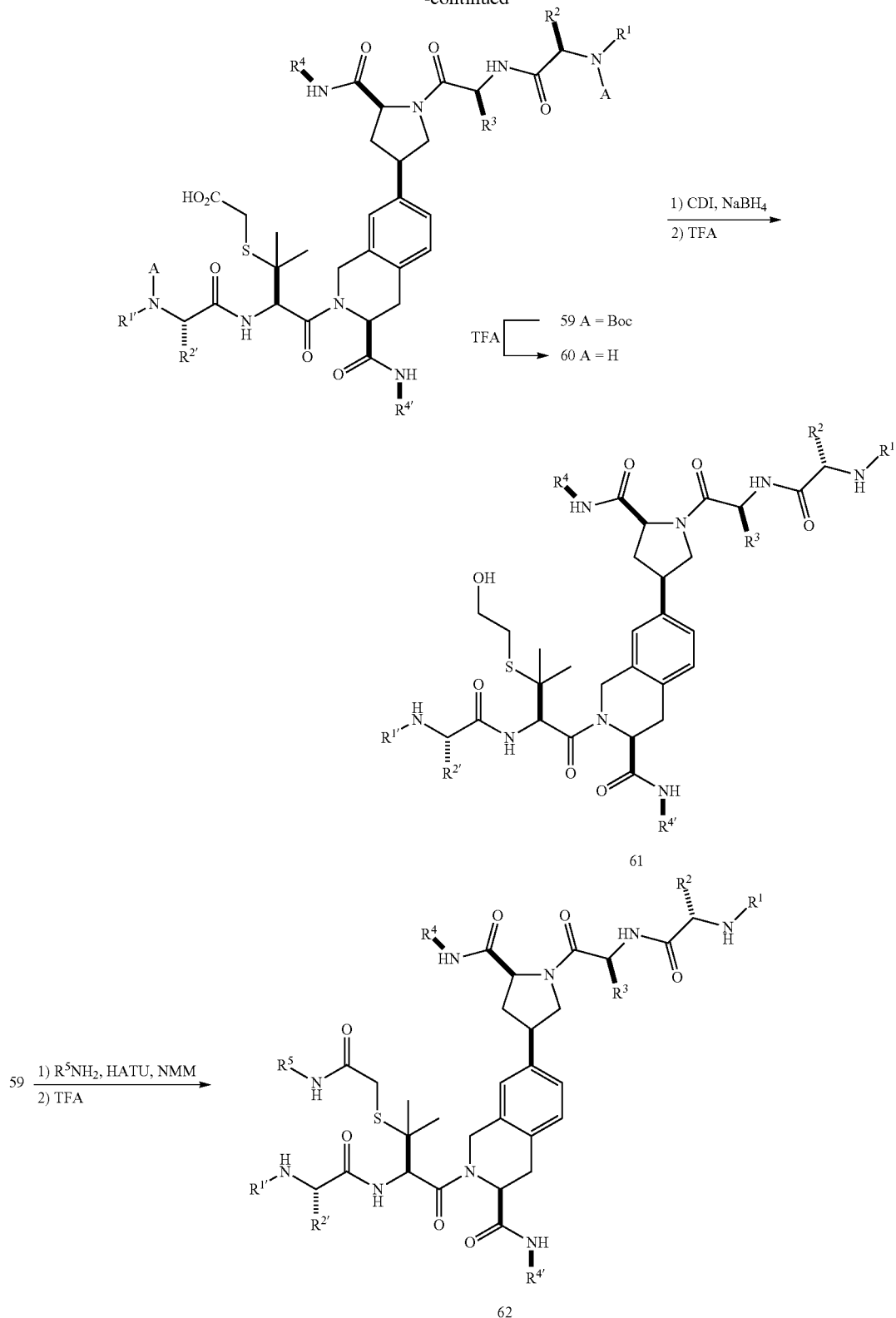

When $R^4 \neq R^{4'}$, the route depicted in Scheme 10 can be employed for the preparation of compounds 42. Enol triflate 63, prepared in two steps from commercially available (S)-1-(tert-butoxycarbonyl)-4-oxopyrrolidine-2-carboxylic acid (Chem-Impex) according to Scheme 6, can undergo Suzuki coupling with boronate ester 64, also prepared according to Scheme 6 starting from (S)-2-tert-butyl 3-methyl 7-(((trifluoromethyl)sulfonyl)oxy)-3,4-dihydroisoquinoline-2,3(1H)- dicarboxylate [Ohta, M. et al., *Chem. Pharm. Bull.*, 58:1066-1076 (2010)]. Following hydrogenation of the olefin, ester hydrolysis can give carboxylic acid 66. Coupling with various primary amines gives intermediate 67 which can be converted to the final analogues 42 as previously shown in Scheme 4.

Scheme 10

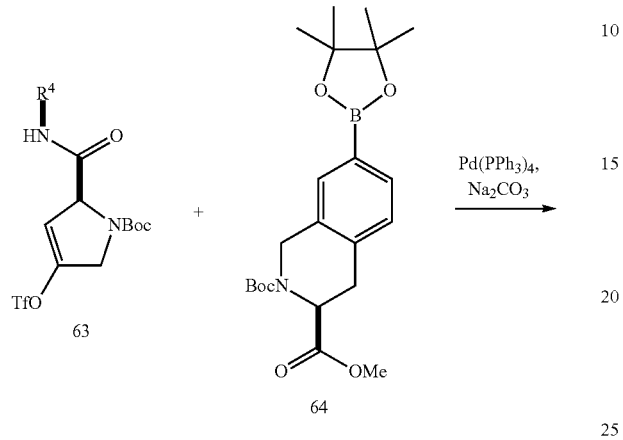

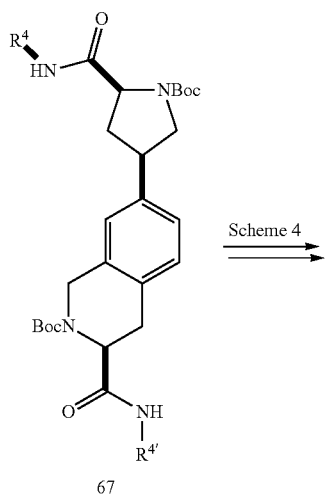

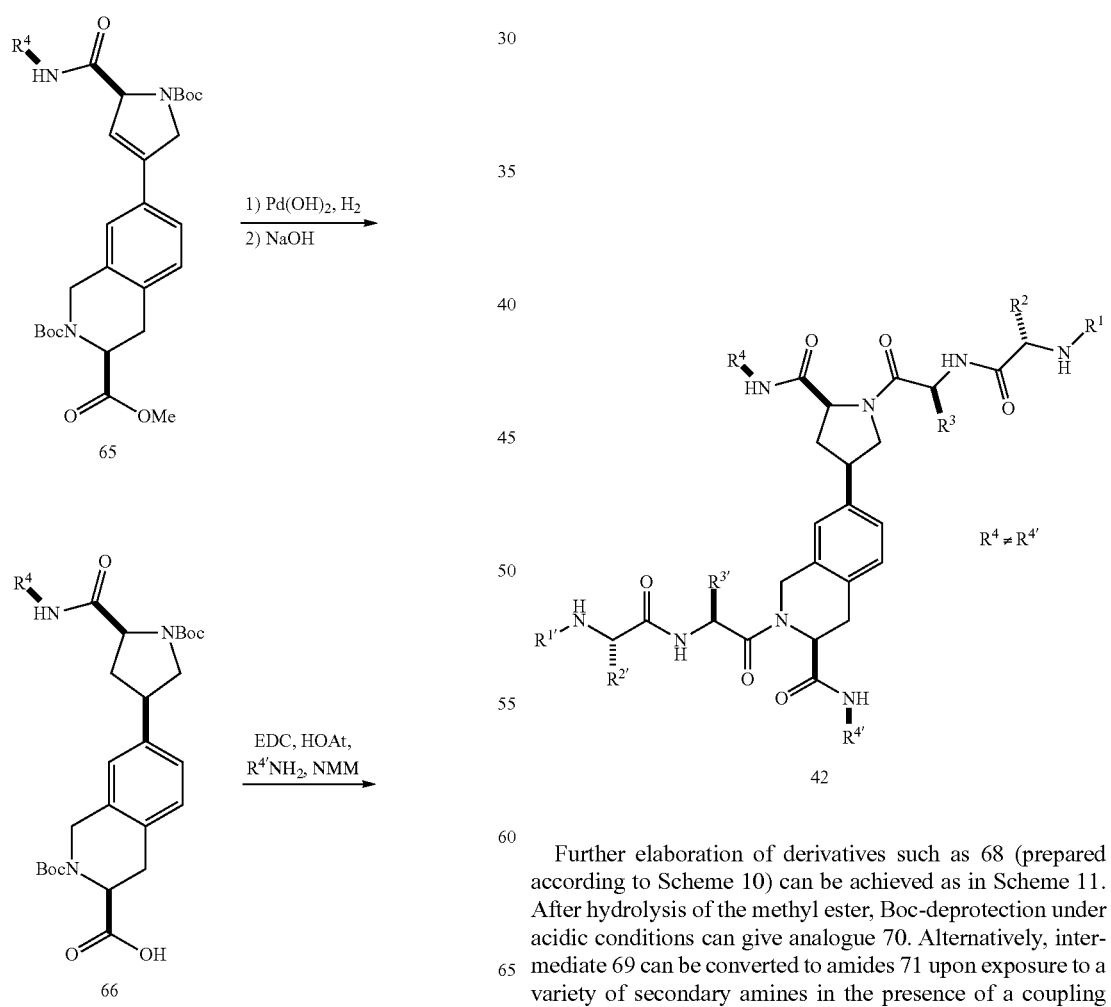

Further elaboration of derivatives such as 68 (prepared according to Scheme 10) can be achieved as in Scheme 11. After hydrolysis of the methyl ester, Boc-deprotection under acidic conditions can give analogue 70. Alternatively, intermediate 69 can be converted to amides 71 upon exposure to a variety of secondary amines in the presence of a coupling reagent followed by treatment with TFA.

Scheme 11
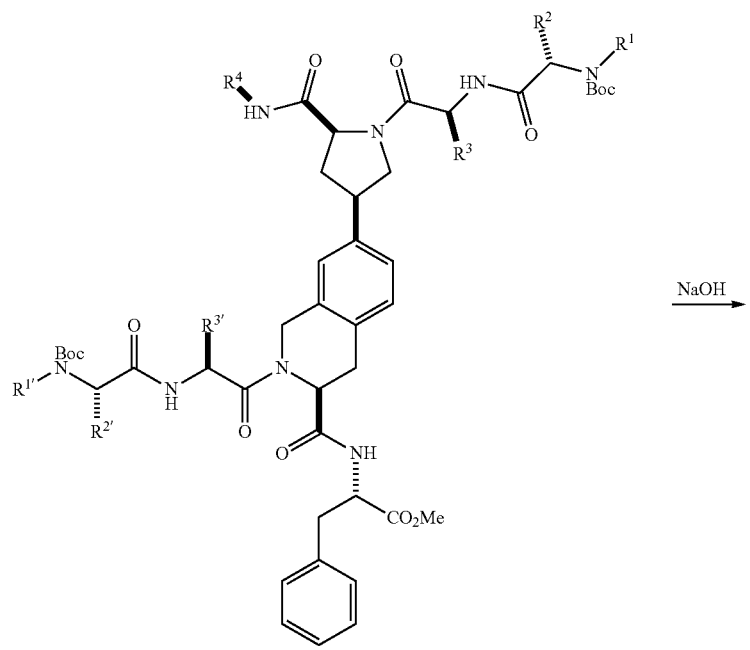
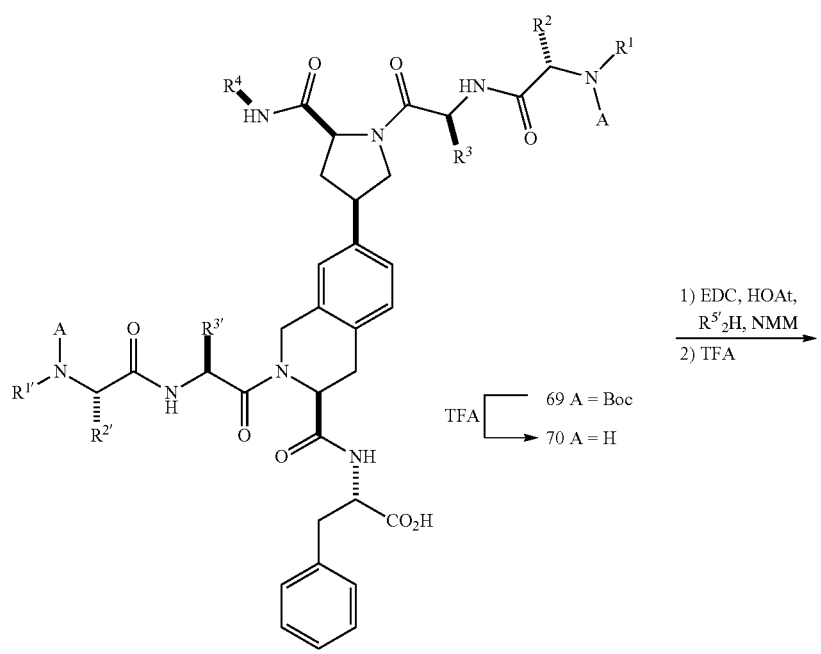

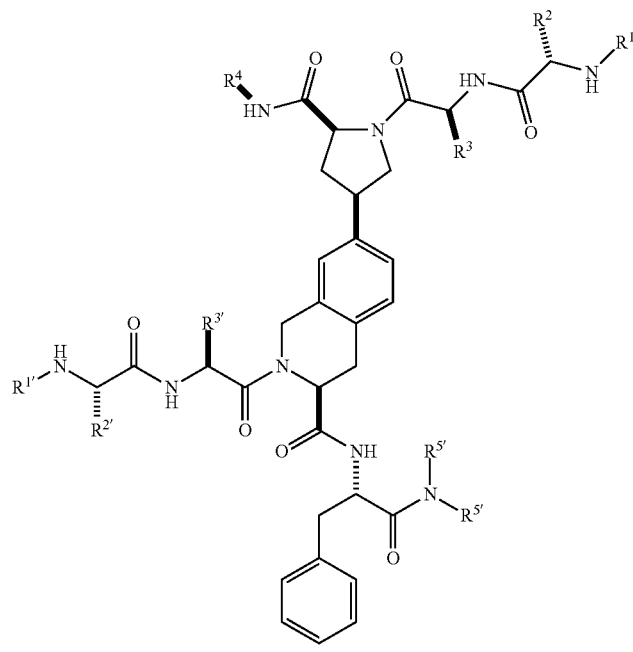

71

Related analogues can be prepared according to Scheme 12. Suzuki coupling of enol triflate 72, prepared in one step from (S)-1-tert-butyl 2-methyl 4-oxopyrrolidine-1,2-dicarboxylate (Aldrich, refer to Scheme 6), and boronate ester 39 (Scheme 6) gives 73 after hydrogenation. Elaboration to 74 can occur as previously described in Scheme 4. Ester hydrolysis under basic conditions followed by coupling with (S)-methyl 2-amino-3-phenylpropanoate (75) gives intermediate 76. Conversion to derivatives 77 can be achieved in three steps (hydrolysis, amide coupling, global Boc-deprotection).

Scheme 12

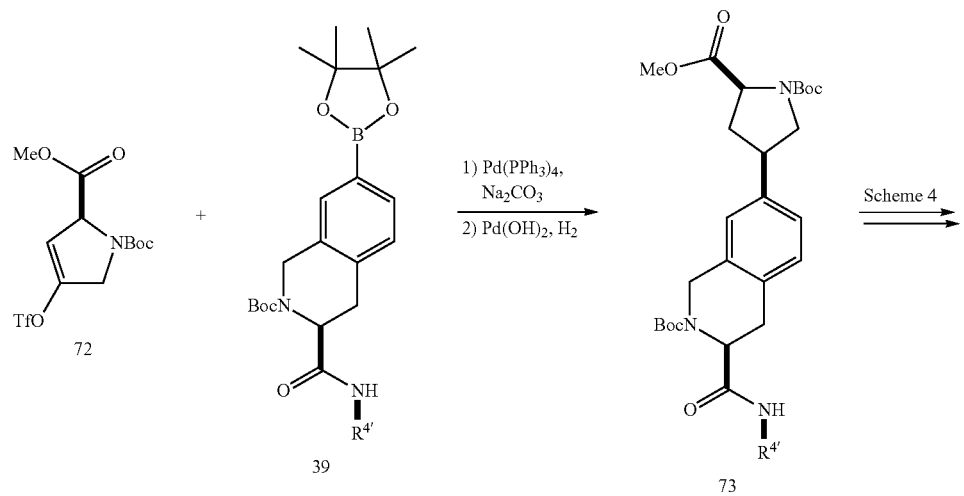

-continued
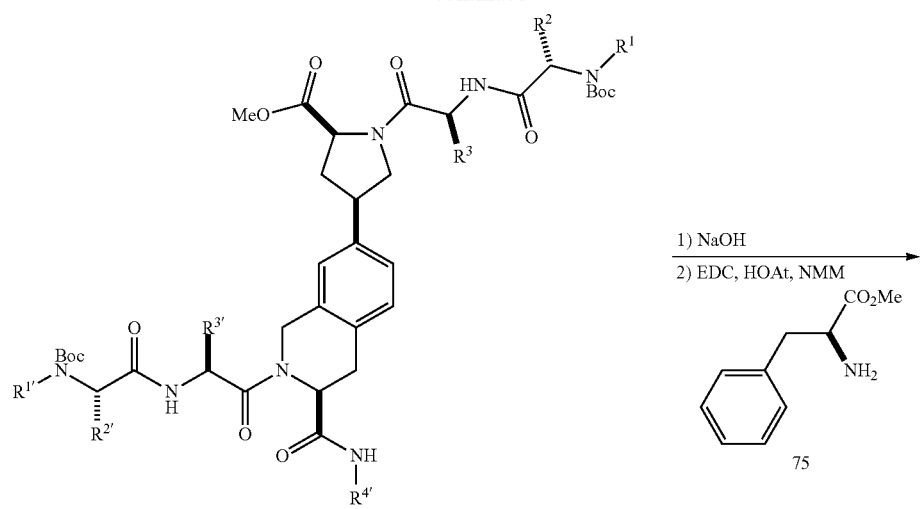
74
1) NaOH
2) EDC, HOAt, NMM
75
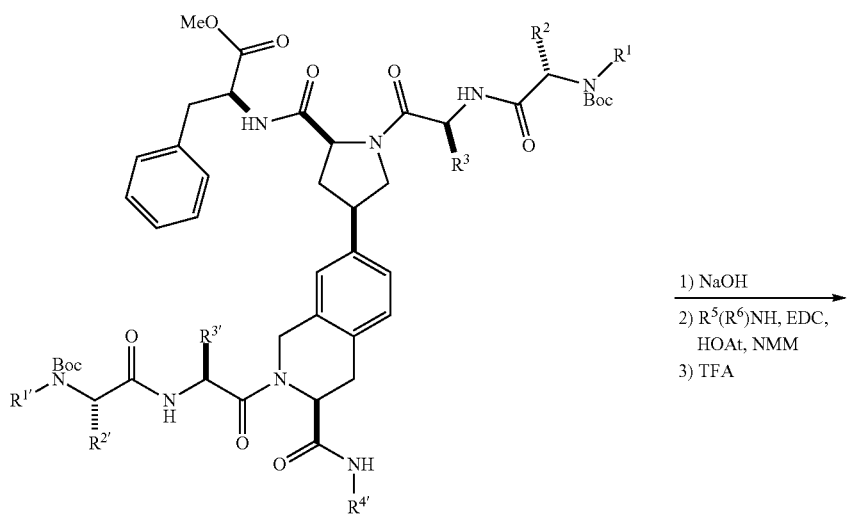
76
1) NaOH
2) R⁵(R⁶)NH, EDC, HOAt, NMM
3) TFA

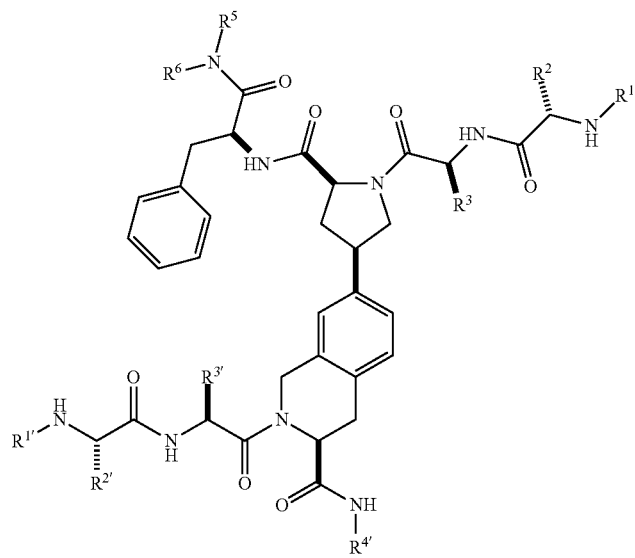

77

As an alternative to Scheme 6, symmetric analogues such as 42 can be prepared as shown in Scheme 13. Suzuki coupling of enol triflate 72 (Scheme 12) and boronate ester 64 (Scheme 10) gives bis-ester 78 after reduction of the olefin. Basic hydrolysis of the esters can be followed by coupling with various primary amines to give bis-amide 79. Conversion to the final analogues 42 can be achieved as previously described in Scheme 4.

Scheme 13

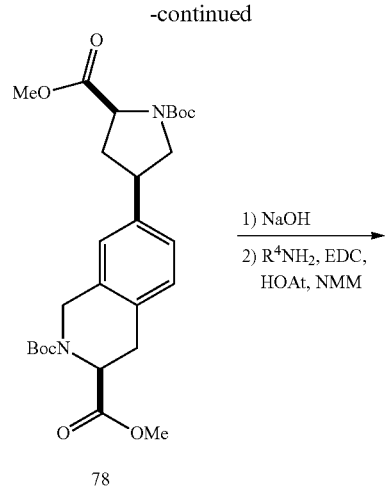

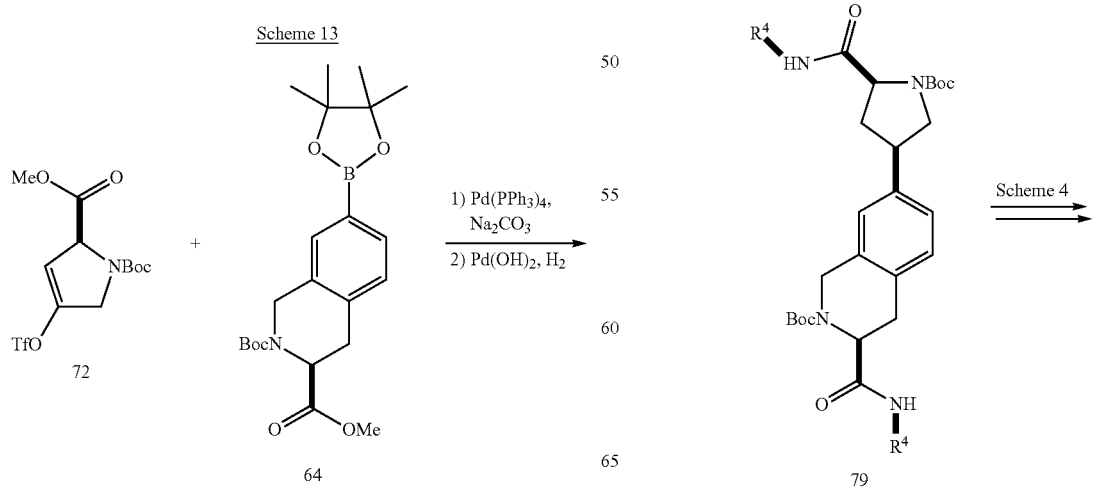

-continued

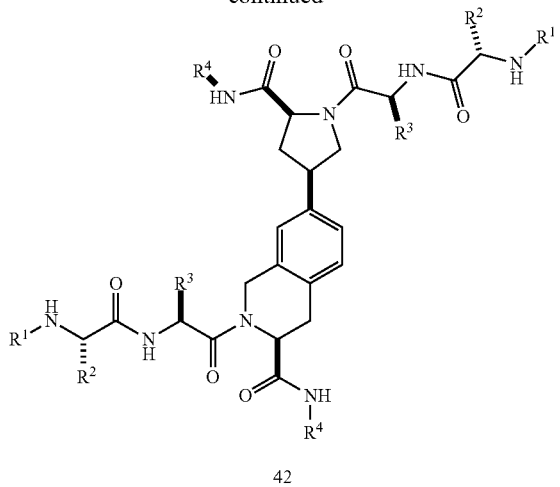

42

EXAMPLES

General Experimental

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using prepacked REDISEP® $R_f$ silica gel columns on a CombiFlash Companion machine.

Preparative Reverse Phase HPLC was performed with a linear gradient elution using $H_2O$/MeOH or $H_2O$/MeCN mixtures buffered with 0.1% trifluoroacetic acid or 10 mM $NH_4OAc$ and detection at 220 nm on one of the following columns: Shimadzu Sunfire S10 30×250 mm (flow rate=40 mL/min), or C18 PHENOMENEX® Luna S5 ODS 21×100 mm (flow rate=20 mL/min), or YMC S5 ODS 20×100 mm (flow rate=20 mL/min) or Waters XBridge C18 19×250 mm (flow rate=20 mL/min) Preparative Supercritical Fluid Chromatography (SFC) was performed using 78% $CO_2$/MeOH buffered with 0.1% diethylamine and detection at 220 nm on a CHIRALPAK® AS-H IDS 25×3 cm column (flow rate=85 mL/min)

All final products were characterized by $^1H$ NMR, RP HPLC and electrospray ionization (ESI) or atmospheric pressure ionization (API) mass spectrometry (MS). $^1H$ NMR spectra were obtained a 500 MHz or a 400 MHz Bruker instrument. Field strengths are expressed in units of δ (parts per million, ppm) relative to the solvent peaks, and peak multiplicities are designated as follows: s, singlet; d, doublet; dd, doublet of doublets; t, triplet; q, quartet; sxt, sextet; br s, broad singlet; m, multiplet.

ABBREVIATIONS

| | |
|---|---|
| AcOH | acetic acid |
| $Ac_2O$ | acetic anhydride |
| ADDP | 1,1'-(azodicarbonyl)dipiperidine |
| aq. | aqueous |
| Bn | benzyl |
| Boc | t-butyl carbamate |
| $Boc_2O$ | di-t-butyl dicarbonate |
| Bu | butyl |
| conc. | concentrated |
| DCE | dichloroethane |
| DCM | dichloromethane |
| DIAD | diisopropyl azodicarboxylate |
| DIPEA | diisopropylethylamine |
| DMAP | 4-N,N-dimethylaminopyridine |
| DMF | dimethyl formamide |
| DMSO | dimethyl sulfoxide |
| EDC | 1-(dimethylaminopropyl)-3-ethylcarbodiimide hydrochloride |
| Et | ethyl |
| EtOAc | ethyl acetate |
| EtOH | ethanol |
| $Et_2O$ | diethyl ether |
| $Et_3N$ | triethyl amine |
| h | hour(s) |
| HATU | O-(7-azabenzotriazol-1-yl)-N,N,N',N'-tetramethyluronium hexafluorophosphate |
| HOAt | 1-hydroxy-7-azabenzotriazole |
| HPLC | high pressure liquid chromatography |
| i-PrOH | isopropanol |
| KOAc | potassium acetate |
| min | minute(s) |
| Me | methyl |
| MeCN | acetonitrile |
| MeOH | methanol |
| $Me_2NH$ | dimethyl amine |
| NaHMDS | sodium bis(trimethylsilyl)amide |
| $Na(OAc)_3BH$ | sodium triacetoxyborohydride |
| n-BuLi | n-butyl lithium |
| NCS | N-chlorosuccinimide |
| NMM | N-methylmorpholine |
| NMP | n-methylpyrrolidinone |
| NMR | nuclear magnetic resonance |
| OTf | trifluoromethylsulfonyloxy |
| Pd/C | palladium on carbon |
| $Pd(dppf)_2Cl_2$ | [1,1'-bis(diphenylphosphino)ferrocene]dichloropalladium(II) |
| $Pd(OAc)_2$ | palladium acetate |
| $Pd(PPh_3)_4$ | tetrakis(triphenylphosphine)palladium |
| $Pd_2(dba)_3$ | tris(dibenzylideneacetone)dipalladium(0) |
| Ph | phenyl |
| PhMe | toluene |
| $PhNTf_2$ | N-phenyl-bis(trifluoromethanesulfonimide) |
| $PPh_3$ | triphenyl phosphorus |
| sat. | saturated |
| t-Bu | tertiary butyl |
| t-BuOH | tertiary butanol |
| TFA | trifluoroacetic acid |
| $Tf_2O$ | trifluoromethylsulfonic anhydride |
| THF | tetrahydrofuran |
| TMS | trimethylsilyl |
| TsO | p-toluenesulfonyl |

Example 1

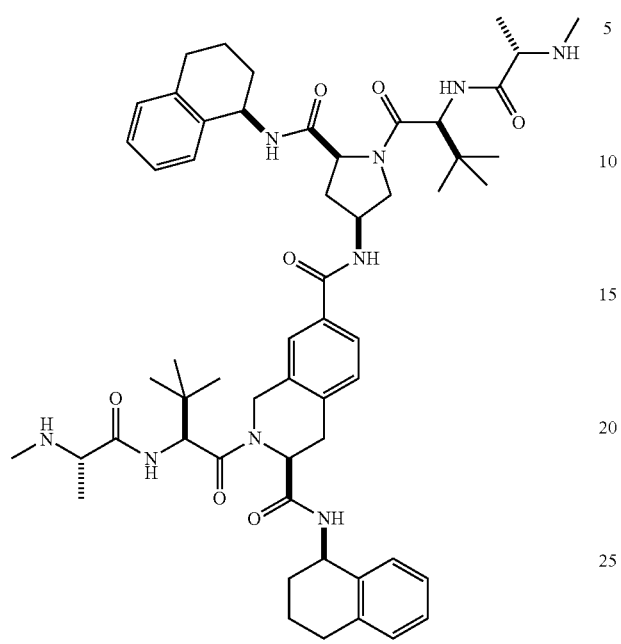

(S)-2-((S)-3,3-Dimethyl-2-((S)-2-(methylamino)propanamido)butanoyl)-N⁷-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N³—((R)-1,2,3,4-tetrahydronaphthalen-1-yl)-1,2,3,4-tetrahydroisoquinoline-3,7-dicarboxamide

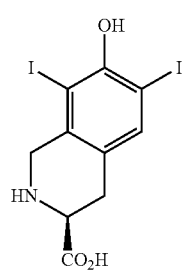 [SMILES: O=C(O)[C@@H]1Cc2cc(I)c(O)c(I)c2CN1]

A) (S)-7-Hydroxy-6,8-diiodo-1,2,3,4-tetrahydroisoquinoline-3-carboxylic acid A thick-walled reaction flask with a screw top was charged sequentially with (S)-2-amino-3-(4-hydroxy-3,5-diiodophenyl)propanoic acid (Chem-Impex Int'l Inc., 5.0 g, 12 mmol), 1,2-dimethoxyethane (5.0 mL), formaldehyde (37% wt. in H₂O, 4.5 mL, 60 mmol), and conc. HCl (60.2 mL, 1981 mmol). The resulting tan slurry was sealed with a screw top and heated to 72° C. slowly over 30 min and then maintained at 72° C. for 12 h. The resulting brown reaction slurry was then cooled to 0° C., filtered while cold, and washed with small amounts of 1,2-dimethoxyethane to give the title compound (2.42 g, 5.45 mmol, 47%) as a white solid. ¹H NMR (DMSO-d₆) δ 9.93 (br s, 1H), 9.69 (br s, 1H), 7.75 (s, 1H), 4.34 (d, J=7.7 Hz, 1H), 4.21-3.94 (m, 2H), 3.93-3.47 (m, 1H), 3.33-3.16 (m, 1H), 3.15-2.97 (m, 1H); MS (ESI⁺) m/z 445.9 (M+H)⁺.

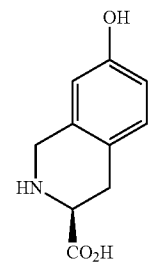

B) (S)-7-Hydroxy-1,2,3,4-tetrahydroisoquinoline-3-carboxylic acid (S)-7-Hydroxy-6,8-diiodo-1,2,3,4-tetrahydroisoquinoline-3-carboxylic acid (2.0 g, 4.5 mmol) and 5% Pd/C (0.48 g, 0.22 mmol) were suspended in H₂O (24 mL) and Et₃N (2.1 mL, 15 mmol). EtOH (73 mL) purged with H₂ was then syringed into a reaction flask. The reaction mixture was topped with a balloon of H₂ and stirred for 4 h. The reaction mixture was filtered through CELITE®, washing with MeOH, and concentrated in vacuo to give crude (S)-7-hydroxy-1,2,3,4-tetrahydroisoquinoline-3-carboxylic acid which was used directly in the next step. MS (ESL) m/z 193.1 (M+H)⁺.

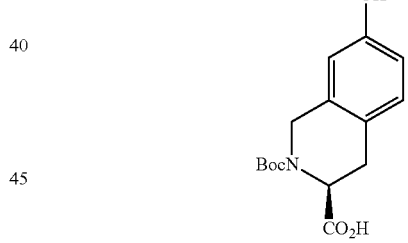

C) (S)-2-(tert-Butoxycarbonyl)-7-hydroxy-1,2,3,4-tetrahydroisoquinoline-3-carboxylic acid To a solution of crude L-7-hydroxy-1,2,3,4-tetrahydroisoquinoline-3-carboxylic acid (0.87 g, 4.5 mmol) and NaHCO₃ (0.76 g, 9.0 mmol) in THF (26 mL) and H₂O (26 mL) was added Boc₂O (1.1 mL, 4.9 mmol). After 12 h the reaction mixture was concentrated in vacuo to remove the volatiles and acidified to pH=4 with 1N HCl, resulting in a cloudy yellow solution. The solution was then partitioned in CH₂Cl₂, and the layers were separated. The aqueous layer was extracted with CH₂Cl₂ (3×), and the combined organic layer was dried over MgSO₄, filtered, and concentrated in vacuo to give crude (S)-2-(tert-butoxycarbonyl)-7-hydroxy-1,2,3,4-tetrahydroisoquinoline-3-carboxylic acid, which was used directly in the next step. MS (ESI⁺) m/z 294.3 (M+H)⁺.

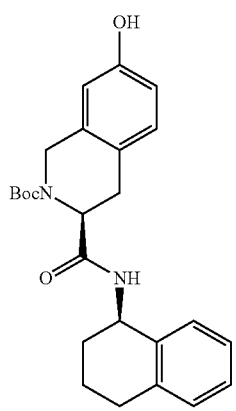 [SMILES: CC(C)(C)OC(=O)N1Cc2cc(O)ccc2C[C@H]1C(=O)N[C@@H]1CCCc2ccccc21]

D) (S)-tert-Butyl 7-hydroxy-3-(((R)-1,2,3,4-tetrahydronaphthalen-1-yl)carbamoyl)-3,4-dihydroisoquinoline-2(1H)-carboxylate To a 0° C. solution of (S)-2-(tert-butoxycarbonyl)-7-hydroxy-1,2,3,4-tetrahydroisoquinoline-3-carboxylic acid (1.32 g, 4.49 mmol) in DMF (30 mL) was added EDC (1.03 g, 5.39 mmol) followed by HOAt (0.73 g, 5.39 mmol). After 10 min, (R)-1,2,3,4-tetrahydronaphthalen-1-amine (Alfa Aesar, 0.66 mL, 4.49 mmol) and NMM (1.48 mL, 13.5 mmol) were added. The resulting reaction mixture was allowed to warm to room temperature over 4 h and then poured into a separatory funnel containing EtOAc and sat. aq. NaHCO$_3$ solution. The aqueous layer was extracted with EtOAc (3×), and the combined organic extracts were washed with 1N HCl, 10% LiCl and sat. NaCl and then dried over MgSO$_4$, filtered and concentrated in vacuo. The crude oil was then purified by flash chromatography (gradient elution from 0 to 70% EtOAc/hexanes) to afford the title compound (1.25 g, 2.96 mmol, 66% over 3 steps) as a light yellow foam. $^1$H NMR (CDCl$_3$) δ 7.18-6.86 (m, 4H), 6.84-6.67 (m, 1H), 6.58-6.39 (m, 1H), 6.04-5.74 (m, 2H), 4.94 (d, J=5.7 Hz, 1H), 4.78-4.61 (m, 1H), 4.56-4.41 (m, 1H), 4.20 (d, J=15.6 Hz, 1H), 3.34 (d, J=13.4 Hz, 1H), 3.02 (d, J=12.1 Hz, 1H), 2.81-2.60 (m, 2H), 1.87-1.68 (m, 2H), 1.67-1.54 (m, 2H), 1.53-1.37 (m, 9H); MS (ESI$^+$) m/z 423.2 (M+H)$^+$.

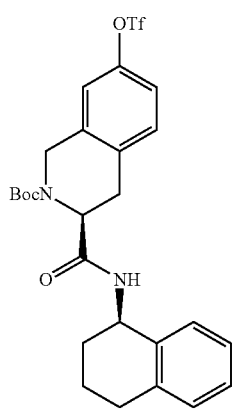 [SMILES: CC(C)(C)OC(=O)N1Cc2cc(OS(=O)(=O)C(F)(F)F)ccc2C[C@H]1C(=O)N[C@@H]1CCCc2ccccc21]

E) (S)-tert-Butyl 3-(((R)-1,2,3,4-tetrahydronaphthalen-1-yl)carbamoyl)-7-(((trifluoromethyl)sulfonyl)oxy)-3,4-dihydroisoquinoline-2(1H)-carboxylate To a solution of (S)-tert-butyl 7-hydroxy-3-(((R)-1,2,3,4-tetrahydronaphthalen-1-yl)carbamoyl)-3,4-dihydroisoquinoline-2(1H)-carboxylate (1.25 g, 2.96 mmol) in CH$_2$Cl$_2$ (30 mL) was added Et$_3$N (1.24 mL, 8.89 mmol) and DMAP (0.036 g, 0.30 mmol). The solution was cooled to 0° C. and PhNTf$_2$ (1.27 g, 3.55 mmol) was then added in one portion. After stirring at 0° C. for 15 min, the reaction mixture was allowed to warm to room temperature, stirred for 1 h and then concentrated in vacuo. The crude oil was purified by flash chromatography (gradient elution from 0 to 70% EtOAc/hexanes) to afford the title compound (1.39 g, 2.50 mmol, 84%) as a white foam. MS (ESI$^+$) m/z 555.4 (M+H)$^+$.

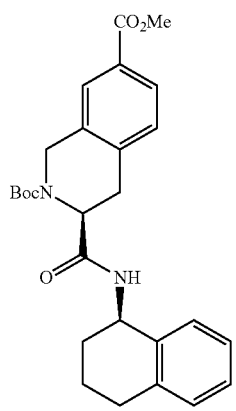 [SMILES: COC(=O)c1ccc2c(c1)CN(C(=O)OC(C)(C)C)[C@H](C(=O)N[C@@H]1CCCc3ccccc31)C2]

F) (S)-2-tert-Butyl 7-methyl 3-(((R)-1,2,3,4-tetrahydronaphthalen-1-yl)carbamoyl)-3,4-dihydroisoquinoline-2,7(1H)-dicarboxylate A 20 mL scintillation vial with a septum top was charged sequentially with (S)-tert-butyl 3-(((R)-1,2,3,4-tetrahydronaphthalen-1-yl)carbamoyl)-7-(((trifluoromethyl)sulfonyl)oxy)-3,4-dihydroisoquinoline-2(1H)-carboxylate (1.39 g, 2.50 mmol), Pd(OAc)$_2$ (0.028 g, 0.12 mmol), and 1,3-bis(diphenylphosphino)propane (0.052 g, 0.12 mmol). DMSO (3.7 mL), MeOH (2.5 mL), and Et$_3$N (0.77 mL, 5.50 mmol) were then added, and the reaction mixture was stirred for 5 min. A CO balloon was then used to purge the reaction vial, turning the solution black. The reaction was topped with the CO balloon and heated to 70° C. for 12 h. The reaction mixture was then filtered through an ACRODISC®, and the filtrate was poured into a separatory funnel containing EtOAc and sat. aq. NH$_4$Cl solution. The aqueous layer was extracted with EtOAc (2×). The combined organic layers were washed with sat. NaCl (2×), dried over MgSO$_4$, filtered and concentrated in vacuo. The crude oil was purified by flash column chromatography (gradient elution from 0 to 50% EtOAc/hexanes) to afford the title compound (1.06 g, 2.28 mmol, 91%) as a light yellow solid. MS (ESI$^+$) m/z 465.2 (M+H)$^+$.

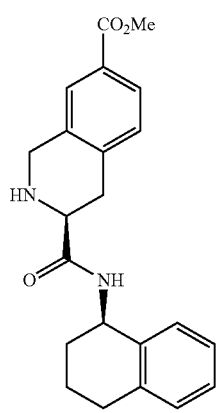 [SMILES: COC(=O)c1ccc2c(c1)CN[C@H](C(=O)N[C@@H]1CCCc3ccccc31)C2]

G) (S)-Methyl 3-(((R)-1,2,3,4-tetrahydronaphthalen-1-yl)carbamoyl)-1,2,3,4-tetrahydroisoquinoline-7-carboxylate To a solution of (S)-2-tert-butyl 7-methyl 3-(((R)-1,2,3,4-tetrahydronaphthalen-1-yl)carbamoyl)-3,4-dihydroisoquinoline-2,7(1H)-dicarboxylate (1.06 g, 2.28 mmol) in CH$_2$Cl$_2$ (22.8 mL) was added TFA (5.7 mL). The resulting reaction mixture was stirred at room temperature for 1 h and then quenched with sat. aq. NaHCO$_3$ solution. The aqueous layer was extracted with EtOAc (3×), and the combined organic extracts were washed with brine, dried over MgSO$_4$, filtered and concentrated in vacuo. The resulting oil was then lyophilized from MeCN/H$_2$O overnight to give the title compound (0.79 g, 2.18 mmol, 96%) as a light yellow solid. $^1$H NMR (DMSO-d$_6$) δ 8.39 (d, J=8.6 Hz, 1H), 7.85-7.67 (m, 2H), 7.34 (d, J=7.9 Hz, 1H), 7.24-7.02 (m, 4H), 5.12-4.93 (m, 1H), 4.23-3.97 (m, 2H), 3.86 (s, 3H), 3.73 (dd, J=10.0, 4.7 Hz, 1H), 3.33 (br s, 1H), 3.18-3.05 (m, 1H), 3.03-2.88 (m, 1H), 2.86-2.63 (m, 2H), 2.02-1.83 (m, 2H), 1.81-1.64 (m, 2H); MS (ESI$^+$) m/z 365.1 (M+H)$^+$.

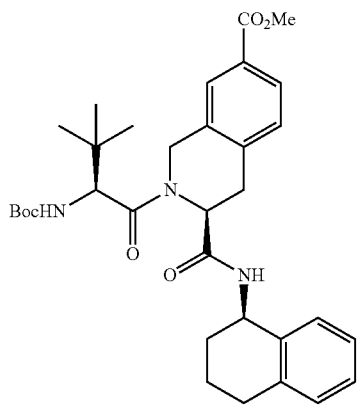 [SMILES: COC(=O)c1ccc2c(c1)CN(C(=O)[C@@H](NC(=O)OC(C)(C)C)C(C)(C)C)[C@H](C(=O)N[C@@H]1CCCc3ccccc31)C2]

H) (S)-Methyl 2-((S)-2-((tert-butoxycarbonyl)amino)-3,3-dimethylbutanoyl)-3-(((R)-1,2,3,4-tetrahydronaphthalen-1-yl)carbamoyl)-1,2,3,4-tetrahydroisoquinoline-7-carboxylate To a 0° C. solution of (S)-2-((tert-butoxycarbonyl)amino)-3,3-dimethylbutanoic acid (473 mg, 2.04 mmol) and (S)-methyl 3-(((R)-1,2,3,4-tetrahydronaphthalen-1-yl)carbam oyl)-1,2,3,4-tetrahydroisoquinoline-7-carboxylate (745 mg, 2.04 mmol) in CH$_2$Cl$_2$ (12.4 mL) was added EDC (471 mg, 2.45 mmol), HOAt (334 mg, 2.45 mmol) and NMM (675 µL, 6.14 mmol). The resulting reaction mixture was allowed to warm to room temperature overnight and then quenched with EtOAc and sat. NaHCO$_3$. The aqueous layer was extracted with EtOAc (3×). The combined organic extracts were washed with 1N HCl (2×), sat. aq. NaCl solution (1×), dried over MgSO$_4$, filtered and concentrated in vacuo to give the title compound (1.18 g, 2.045 mmol, 100%) as a light yellow foam, which was used without further purification. MS (ESI$^+$) m/z 578.2 (M+H)$^+$.

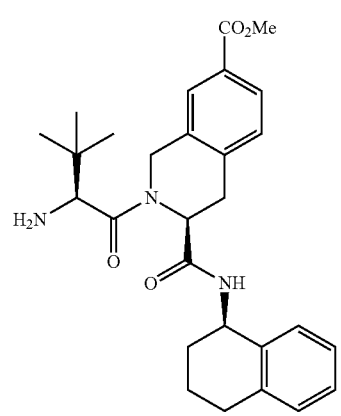 [SMILES: COC(=O)c1ccc2c(c1)CN(C(=O)[C@@H](N)C(C)(C)C)[C@H](C(=O)N[C@@H]1CCCc3ccccc31)C2]

I) (S)-Methyl 2-((S)-2-amino-3,3-dimethylbutanoyl)-3-(((R)-1,2,3,4-tetrahydronaphthalen-1-yl)carbamoyl)-1,2,3,4-tetrahydroisoquinoline-7-carboxylate A solution of (S)-methyl 2-((S)-2-((tert-butoxycarbonyl)amino)-3,3-dimethylbutanoyl)-3-(((R)-1,2,3,4-tetrahydronaphthalen-1-yl)carbamoyl)-1,2,3,4-tetrahydroisoquinoline-7-carboxylate (1.21 g, 2.09 mmol) in CH$_2$Cl$_2$ (13.9 mL) was charged with TFA (3.49 mL) at room temperature. After 40 min, the reaction mixture was quenched carefully with sat. NaHCO$_3$ and then extracted with EtOAc (3×). The combined extracts were washed with sat. NaCl, dried over MgSO$_4$, filtered and concentrated in vacuo to afford the title compound (0.97 g, 2.02 mmol, 97%) as a light yellow foam, which was used without further purification. MS (ESI$^+$) m/z 478.2 (M+H)$^+$.

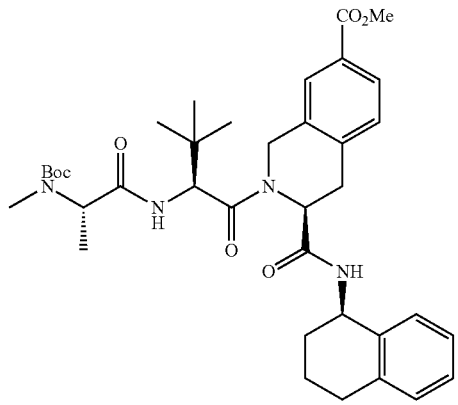 [SMILES: COC(=O)c1ccc2c(c1)CN(C(=O)[C@@H](NC(=O)[C@H](C)N(C)C(=O)OC(C)(C)C)C(C)(C)C)[C@H](C(=O)N[C@@H]1CCCc3ccccc31)C2]

J) (S)-Methyl 2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxylate To a 0° C. solution of (S)-methyl 2-((S)-2-amino-3,3-dimethylbutanoyl)-3-(((R)-1,2,3,4-tetrahydronaphthalen-1-yl)carbamoyl)-1,2,3,4-tetrahydroisoquinoline-7-carboxylate (966 mg, 2.02 mmol) and (S)-2-((tert-butoxycarbonyl)(methyl)amino)propanoic acid (Advanced ChemTech, 411 mg, 2.02 mmol) in DMF (20 mL) was added EDC (465 mg, 2.43 mmol), followed by HOAt (330 mg, 2.43 mmol). NMM (667 µl, 6.07 mmol) was then added, and the resulting reaction mixture was stirred at 0° C. for 30 min, then warmed to room temperature and stirred for 4 h. The reaction mixture was then poured into a separatory funnel containing EtOAc and sat. aq. NaHCO₃ solution. The aqueous layer was extracted with EtOAc (3×). The combined organic extracts were washed with 1N HCl (2×) and 10% LiCl, dried over MgSO₄, filtered, and concentrated in vacuo to give the title compound (1.34 g, 2.02 mmol, 100%) as a light yellow foam, which was used without further purification. MS (ESI$^+$) m/z 663.3 (M+H)$^+$.

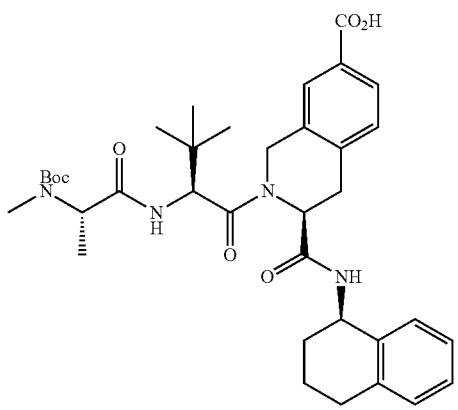 [SMILES: C[C@@H](C(=O)N[C@H](C(=O)N1Cc2cc(C(=O)O)ccc2C[C@H]1C(=O)N[C@@H]1CCCc2ccccc21)C(C)(C)C)N(C)C(=O)OC(C)(C)C]

K) (S)-2-((S)-2-((S)-2-((tert-Butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxylic acid To a solution of (S)-methyl 2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxylate (1.34 g, 2.02 mmol) in THF (13.5 mL) and MeOH (6.7 mL) was added NaOH(aq.) (3N, 3.4 mL, 10.1 mmol). After 3 h, the reaction mixture was poured into a sep funnel containing EtOAc and 1N HCl. The aqueous layer was extracted with EtOAc (3×), and the combined organic extracts were dried over MgSO₄, filtered and concentrated in vacuo to afford the title compound (1.25 g, 1.93 mmol, 95%) as a light yellow foam, which was used without further purification. MS (ESI$^+$) m/z 649.3 (M+H)$^+$.

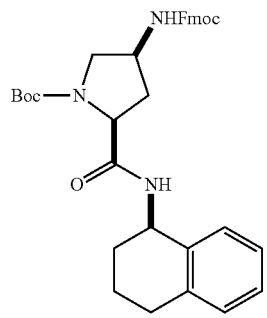

L) (2S,4S)-tert-Butyl 4-(((((9H-fluoren-9-yl)methoxy)carbonyl)amino)-2-(((R)-1,2,3,4-tetrahydronaphthalen-1-yl)carbamoyl)pyrrolidine-1-carboxylate To a solution of (2S,4S)-Boc-gamma-(Fmoc-amino)-proline (Chem-Impex, 6.00 g, 13.3 mmol) in DMF (20 mL) at 0° C. were added EDC (3.05 g, 15.9 mmol), HOAt (2.17 g, 15.9 mmol) and NMM (4.38 mL, 39.8 mmol). The reaction mixture was stirred at ice bath temperature for 20 min then treated with a solution of (R)-1,2,3,4-tetrahydronaphthalen-1-amine (Alfa Aesar, 2.15 g, 14.6 mmol) in DMF (2 mL). The reaction mixture was stirred at rt for 1 h and cold water (100 mL) was added to the reaction mixture. The solid that formed was collected by filtration and washed with cold water (100 mL). The solid was dissolved in CH₂Cl₂ (200 mL) and the organic solution was washed with 5% aq. citric acid solution and brine, dried over MgSO₄, and filtered. The filtrate was concentrated in vacuo. The residue was dissolved in CH₂Cl₂ and purified by flash column chromatography (gradient elution from 10 to 30% EtOAc in CH₂Cl₂) provided the title compound (6.70 g, 87%) as a light tan solid. $^1$H NMR (400 MHz, CDCl₃) δ 7.79 (d, J=7.5 Hz, 2H), 7.67 (d, J=7.3 Hz, 2H), 7.42 (td, J=7.2, 4.0 Hz, 2H), 7.37-7.03 (m, 6H), 5.22 (br. s., 1H), 4.57-4.23 (m, 5H), 3.68-3.49 (m, 2H), 2.91-2.74 (m, 2H), 2.52 (d, J=13.4 Hz, 1H), 2.35-2.21 (m, 1H), 2.14 (d, J=5.1 Hz, 1H), 1.97-1.80 (m, 3H), 1.44 (s, 9H); MS (ESI$^+$) m/z 582.2 (M+H)$^+$.

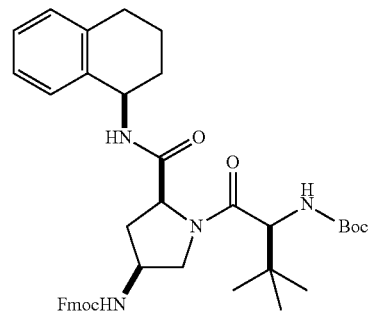

M) tert-Butyl ((S)-3,3-dimethyl-1-((2S,4S)-4-((((9H-fluoren-9-yl)methoxy)carbonyl)amino)-2-(((R)-1,2,3,4-tetrahydronaphthalen-1-yl)carbamoyl)pyrrolidin-1-yl)-1-oxobutan-2-yl)carbamate To a solution of (2S,4S)-tert-butyl 4-(((((9H-fluoren-9-yl)methoxy)carbonyl)amino)-2-(((R)-1,2,3,4-tetrahydronaphthalen-1-yl)carbamoyl)pyrrolidine-1-carboxylate (6.70 g, 11.5 mmol) in CH$_2$Cl$_2$ (50 mL) at rt was added TFA (15 mL) dropwise. The reaction mixture was stirred at rt for 2 h, and then concentrated in vacuo. The residue was dissolved in CH$_2$Cl$_2$ (200 mL) and washed with aq. K$_2$HPO$_4$ solution (50 mL). The organic layer was dried over MgSO$_4$, filtered and concentrated in vacuo to give crude (9H-fluoren-9-yl)methyl ((3S,5S)-5-(((R)-1,2,3,4-tetrahydronaphthalen-1-yl)carbamoyl)pyrrolidin-3-yl)carbamate (5.54 g, 100%), which was used directly in the next step.

To a solution of (S)-2-((tert-butoxycarbonyl)amino)-3,3-dimethylbutanoic acid (3.19 g, 13.8 mmol) in DMF (20 mL) at 0° C. were added EDC (3.31 g, 17.3 mmol), HOAt (2.35 g, 17.3 mmol) and NMM (3.80 mL, 34.5 mmol). The reaction mixture was stirred at ice bath temperature for 20 min, then treated with a suspension of (9H-fluoren-9-yl)methyl ((3S,5S)-5-(((R)-1,2,3,4-tetrahydronaphthalen-1-yl)carbamoyl)pyrrolidin-3-yl)carbamate (5.54 g, 11.5 mmol) in DMF (5 mL). The reaction mixture was stirred at rt for 1 h and cold water (200 mL) was added to the reaction mixture. The solid that formed was collected by filtration and washed with of cold water (100 mL). The solid was dissolved in CH$_2$Cl$_2$ (200 mL). The organic solution was washed with sat. aq. NaHCO$_3$ solution, 5% aq. citric acid solution and brine, dried over MgSO$_4$ and filtered. The filtrate was concentrated in vacuo. The residue was dissolved in CH$_2$Cl$_2$ and purified using flash column chromatography (gradient elution from 10 to 30% EtOAc in CH$_2$Cl$_2$) provided the title compound (7.10 g, 89%) as a light tan solid. MS (ESI$^+$) m/z 695.5 (M+H)$^+$.

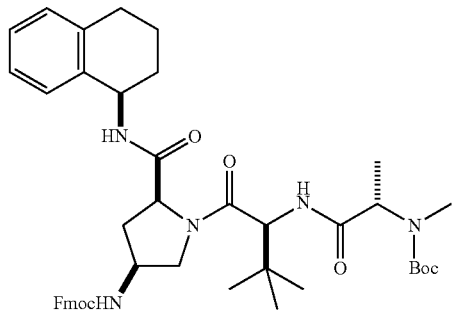

N) tert-Butyl ((S)-1-(((S)-1-((2S,4S)-4-((((9H-fluoren-9-yl)methoxy)carbonyl)amino)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of tert-butyl ((S)-3,3-dimethyl-1-((2S,4S)-4-(((9H-fluoren-9-yl)methoxy)carbonyl)amino)-2-(((R)-1,2,3,4-tetrahydronaphthalen-1-yl)carbamoyl)pyrrolidin-1-yl)-1-oxobutan-2-yl)carbamate (7.10 g, 10.2 mmol) in CH$_2$Cl$_2$ (50 mL) at rt was added TFA (15 mL) dropwise. The reaction mixture was stirred at rt for 2 h, and then concentrated in vacuo. The residue was dissolved in CH$_2$Cl$_2$ (200 mL) and washed with aq. K$_2$HPO$_4$ solution (50 mL). The organic layer was dried over MgSO$_4$, filtered and concentrated in vacuo to give crude (9H-fluoren-9-yl)methyl ((3S,5S)-5-(((R)-1,2,3,4-tetrahydronaphthalen-1-yl)carbamoyl)pyrrolidin-3-yl)carbamate (6.08 g, 100%), which was used directly in the next step.

To a solution of (S)-2-((tert-butoxycarbonyl)(methyl)amino)propanoic acid (Chem-Impex, 2.49 g, 12.3 mmol) in DMF (20 mL) at 0° C. were added EDC (2.94 g, 15.3 mmol), HOAt (2.09 g, 15.3 mmol) and NMM (2.81 mL, 25.6 mmol). The reaction mixture was stirred at ice bath temperature for 20 min, and then treated with a solution of (9H-fluoren-9-yl)methyl ((3S,5S)-5-(((R)-1,2,3,4-tetrahydronaphthalen-1-yl)carbamoyl)pyrrolidin-3-yl)carbamate (6.45 g, 10.2 mmol) in DMF (5 mL). The reaction mixture was stirred at rt for 2 h and then cold water (200 mL) was added to the reaction mixture. The solid that formed was collected by filtration and washed with cold water (100 mL). The solid was dissolved in CH$_2$Cl$_2$ (200 mL). The organic solution was washed with sat. aq. NaHCO$_3$ solution, 5% aq. citric acid solution and brine, dried over MgSO$_4$, and filtered. The filtrate was concentrated in vacuo. The residue was dissolved in CH$_2$Cl$_2$ and purified by flash column chromatography (gradient elution from 10 to 40% EtOAc in CH$_2$Cl$_2$) provided the title compound (6.14 g, 77%) as a light tan solid. MS (ESI$^+$) m/z 780.5 (M+H)$^+$.

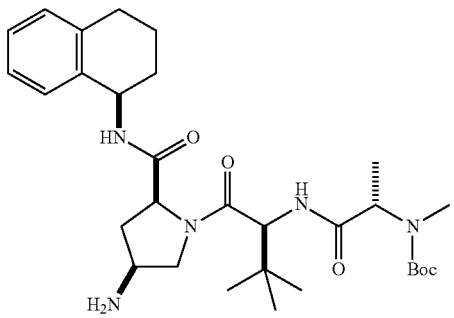

O) tert-Butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of tert-butyl ((S)-1-(((S)-1-((2S,4S)-4-((((9H-fluoren-9-yl)methoxy)carbonyl)amino)-2-(R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (6.14 g, 7.87 mmol) in CH$_2$Cl$_2$ (40 mL) was added piperidine (4.67 mL, 47.2 mmol) dropwise. The reaction mixture was stirred at rt for 2 h and concentrated in vacuo. The residue was washed with methanol and the resulting solid was removed by filtration. The filtrate was concentrated in vacuo and purified by flash column chromatography (gradient elution from 0 to 10% MeOH/CH$_2$Cl$_2$) to give the title compound (3.48 g, 79%) as a light tan solid. MS (ESI$^+$) m/z 558.4 (M+H)$^+$.

P)

Following procedures analogous to those for the preparation of Compounds D and G, (S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxylic acid (Compound K, 63 mg, 0.097 mmol) and tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound O, 57 mg, 0.10 mmol) were converted to the title compound (24 mg, 27% over 2 steps) after purification using prep HPLC. MS (ESI$^+$) m/z 988.6 (M+H)$^+$.

Alternatively, Example 1 could be prepared as follows:

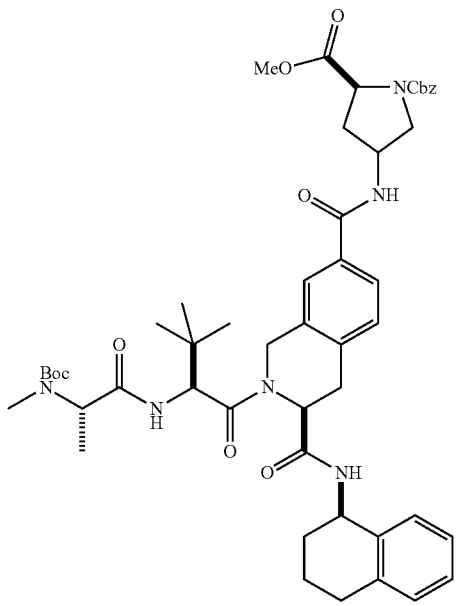

Q) (2S,4S)-1-Benzyl 2-methyl 4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxamido)pyrrolidine-1,2-dicarboxylate Following a procedure analogous to that for the synthesis of Compound D, (S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxylic acid (Compound K, 165 mg, 0.25 mmol) and (2S,4S)-1-benzyl 2-methyl 4-aminopyrrolidine-1,2-dicarboxylate, HCl (Acesys Pharmatech, 80 mg, 0.25 mmol) were converted to the title compound (192 mg, 83%). MS (ESI⁺) m/z 909.3 (M+H)⁺.

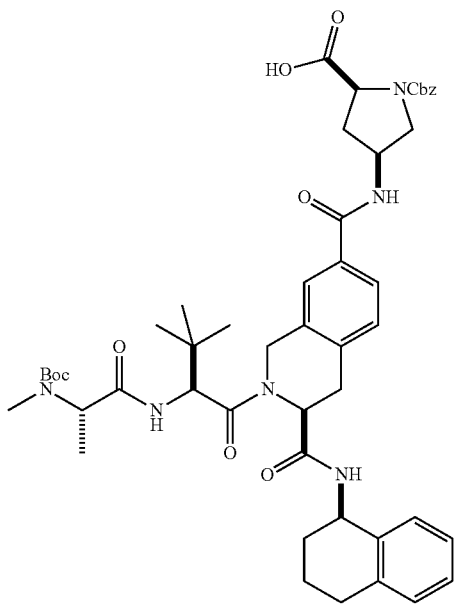

R) (2S,4S)-1-((Benzyloxy)carbonyl)-4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxamido)pyrrolidine-2-carboxylic acid Following a procedure analogous to that for the synthesis of Compound K, (2S,4S)-1-benzyl 2-methyl 4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxamido)pyrrolidine-1,2-dicarboxylate (192 mg, 0.21 mmol) was converted to the title compound (187 mg, 99%). MS (ESI⁺) m/z 895.5 (M+H)⁺.

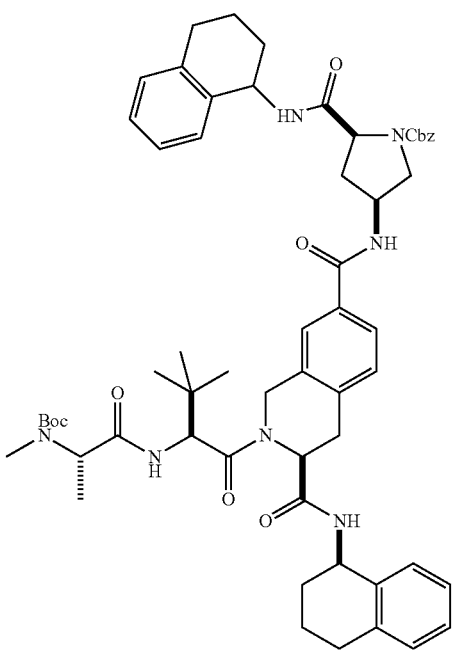

S) (2S,4S)-Benzyl 4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxamido)-2-(((R)-1,2,3,4-tetrahydronaphthalen-1-yl)carbamoyl)pyrrolidine-1-carboxylate Following a procedure analogous to that for the synthesis of Compound D, (2S,4S)-1-((benzyloxy)carbonyl)-4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxamido)pyrrolidine-2-carboxylic acid (187 mg, 0.21 mmol) and (R)-1,2,3,4-tetrahydronaphthalen-1-amine (Alfa Aesar, 31 μL, 0.21 mmol) were converted to the title compound (178 mg, 83%). MS (ESI⁺) m/z 1024.6 (M+H)⁺.

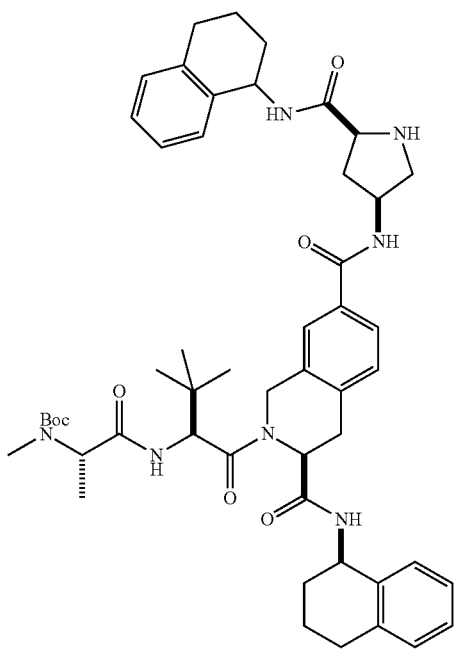

T) tert-Butyl ((S)-1-(((S)-3,3-dimethyl-1-oxo-1-4S)-3-(((R)-1,2,3,4-tetrahydronaphthalen-1-yl)carbamoyl)-7-(((3S,5S)-5-(((R)-1,2,3,4-tetrahydronaphthalen-1-yl)carbamoyl)pyrrolidin-3-yl)carbamoyl)-3,4-dihydroisoquinolin-2(1H)-yl)butan-2-yl)amino)-1-oxopropan-2-yl)(methyl)carbamate To a 50 mL pressure flask containing Pd(OH)$_2$ on carbon (2 mg, 0.02 mmol) was added a solution of (2S,4S)-benzyl 4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-7-carboxamido)-2-(((R)-1,2,3,4-tetrahydronaphthalen-1-yl)carbamoyl)pyrrolidine-1-carboxylate (177 mg, 0.17 mmol) in MeOH (5.8 mL). The resulting reaction mixture was stirred under H$_2$ at 15 psi for 2 h and then filtered through a pad of CELITE® washing with EtOAc. The filtrate was concentrated in vacuo, and the resulting crude oil was purified using flash column chromatography (gradient elution from 0 to 10% NH$_3$/MeOH/CH$_2$Cl$_2$) to give the title compound (80 mg, 52%) as a colorless oil. MS (ESI$^+$) m/z 890.6 (M+H)$^+$.

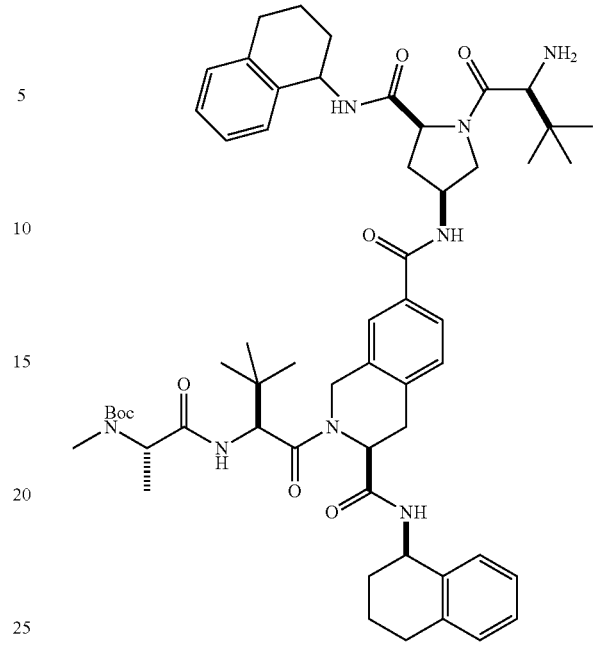

U) tert-Butyl ((S)-1-(((S)-1-(S)-7-(((3S,5S)-1-((S)-2-amino-3,3-dimethylbutanoyl)-5-(((R)-1,2,3,4-tetrahydronaphthalen-1-yl)carbamoyl)pyrrolidin-3-yl) carbamoyl)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl) (methyl)carbamate Following a procedure analogous to that for the synthesis of Compounds H, tert-butyl ((S)-1-(S)-3,3-dimethyl-1-oxo-1-((S)-3-(((R)-1,2,3,4-tetrahydronaphthalen-1-yl)carbamoyl)-7-(3S,5S)-5-(((R)-1,2,3,4-tetrahydronaphthalen-1-yl)carbamoyl)pyrrolidin-3-yl)carbamoyl)-3,4-dihydroisoquinolin-2(1H)-yl)butan-2-yl)amino)-1-oxopropan-2-yl)(methyl)carbamate (80 mg, 0.090 mmol) and (S)-2-((((9H-fluoren-9-yl)methoxy)carbonyl)amino)-3,3-dimethylbutanoic acid (Chem Impex, 33 mg, 0.094 mmol) were reacted to give a crude oil, which was then dissolved in CH$_2$Cl$_2$ (1.8 mL). Piperidine (71 µL, 0.72 mmol) was added, and the resulting reaction mixture was stirred at room temperature overnight and then concentrated in vacuo. The crude oil was redissolved in MeOH and concentrated in vacuo again. The resulting residue was dissolved in a minimal amount of CH$_2$Cl$_2$ and filtered through a pad of silica gel washing with 50% EtOAc/hexanes (50 mL). The silica pad was then washed with 10% MeOH/CH$_2$Cl$_2$ (50 mL) followed by 20% NH$_3$/MeOH/CH$_2$Cl$_2$ (35 mL) into separate flasks. The combined MeOH washes were concentrated in vacuo to give the title compound which was used directly in the subsequent step. MS (ESI$^+$) m/z 1003.6 (M+H)$^+$.

V) (S)-2-((S)-3,3-Dimethyl-2-((S)-2-(methylamino) propanamido)butanoyl)-N$^7$-((3S,5S)-1-((S)-3,3-dimethyl-2-((S)-2-(methylamino)propanamido)butanoyl)-5-(((R)-1,2,3,4-tetrahydronaphthalen-1-yl) carbamoyl)pyrrolidin-3-yl)-N$^3$—((R)-1,2,3,4-tetrahydronaphthalen-1-yl)-1,2,3,4-tetrahydroisoquinoline-3,7-dicarboxamide Following a procedure analogous to that for the synthesis of Compounds J, tert-butyl ((S)-1-(((S)-1-((S)-7-(((3S,5S)-1-

((S)-2-amino-3,3-dimethylbutanoyl)-5-(((R)-1,2,3,4-tetrahydronaphthalen-1-yl)carbamoyl)pyrrolidin-3-yl)carbamoyl)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (90 mg, 0.090 mmol) and (S)-2-((tert-butoxycarbonyl)(methyl)amino)propanoic acid (Advanced ChemTech, 19 mg, 0.094 mmol) were reacted to give a crude oil which was used without purification in the subsequent step. MS (ESI⁺) m/z 1188.7 (M+H)⁺.

The crude oil from above was dissolved in TFA (2.1 mL, 5.40 mmol, 20% in $CH_2Cl_2$) and stirred at room temperature for 1 h. The reaction mixture was then concentrated in vacuo and purified using prep HPLC to give the title compound (45 mg, 50% over 4 steps) as a white solid after lyophilization. MS (ESI⁺) m/z 988.6 (M+H)⁺.

Examples 2 to 5

The following Examples were prepared according to the procedures described for the synthesis of Example 1.

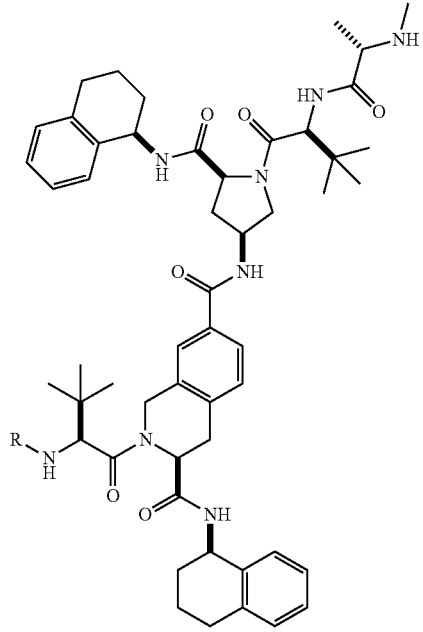

| Ex. No. | R | Name | LCMS (M + H) |
|---|---|---|---|
| 2 | ethylamino-methyl-propanoyl group | (S)-$N^7$-(3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-2-((S)-2-((S)-2-(ethylamino)propanamido)-3,3-dimethylbutanoyl)-$N^3$-((R)-1,2,3,4-tetrahydronaphthalen-1-yl)-1,2,3,4-tetrahydroisoquinoline-3,7-dicarboxamide | 1002.9 |
| 3 | methylamino-ethyl-propanoyl group | (S)-2-((S)-3,3-Dimethyl-2-((S)-2-(methylamino)butanamido)butanoyl)-$N^7$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-$N^3$-((R)-1,2,3,4-tetrahydronaphthalen-1-yl)-1,2,3,4-tetrahydroisoquinoline-3,7-dicarboxamide | 1002.9 |
| 4 | methylamino-isopropyl-propanoyl group | (S)-$N^7$-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-2-((S)-3,3-dimethyl-2-((S)-3-methyl-2-(methylamino)butanamido)butanoyl)-$N^3$-((R)-1,2,3,4-tetrahydronaphthalen-1-yl)-1,2,3,4-tetrahydroisoquinoline-3,7-dicarboxamide | 1016.9 |
| 5 | methylamino-cyclopropyl-acetyl group | (S)-2-((S)-2-((S)-2-Cyclopropyl-2-(methylamino)acetamido)-3,3-dimethylbutanoyl)-$N^7$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-$N^3$-((R)-1,2,3,4-tetrahydronaphthalen-1-yl)-1,2,3,4-tetrahydroisoquinoline-3,7-dicarboxamide | 1014.8 |

Examples 6 to 13

The following Examples were prepared according to the procedures described for the synthesis of Example 1.

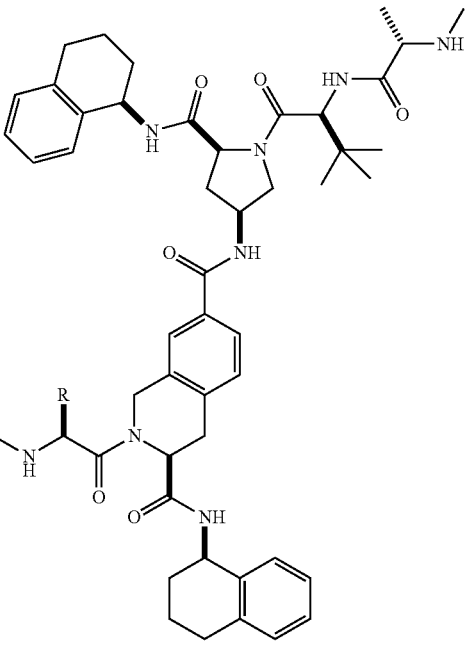

| Ex. No. | R | Name | LCMS (M + H) |
|---|---|---|---|
| 6 | cyclopentylmethyl | (S)-2-((S)-3-Cyclopentyl-2-((S)-2-(methylamino) propanamido)propanoyl)-N$^7$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N$^3$-((R)-1,2,3,4-tetrahydronaphthalen-1-yl)-1,2,3,4-tetrahydroisoquinoline-3,7-dicarboxamide | 1015.8 |
| 7 | 1-methoxyethyl | (S)-N$^7$-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-2-((2S,3R)-3-methoxy-2-((S)-2-(methylamino)propanamido)butanoyl)-N$^3$-((R)-1,2,3,4-tetrahydronaphthalen-1-yl)-1,2,3,4-tetrahydroisoquinoline-3,7-dicarboxamide | 991.6 |
| 8 | sec-butyl-CH | (S)-N$^7$-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-2-((S)-3-ethyl-2-((S)-2-(methylamino)propanamido)pentanoyl)-N$^3$-((R)-1,2,3,4-tetrahydronaphthalen-1-yl)-1,2,3,4-tetrahydroisoquinoline-3,7-dicarboxamide | 1002.4 |
| 9 | cyclohexylmethyl | (S)-2-((S)-3-Cyclohexyl-2-((S)-2-(methylamino) propanamido)propanoyl)-N$^7$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N$^3$-((R)-1,2,3,4-tetrahydronaphthalen-1-yl)-1,2,3,4-tetrahydroisoquinoline-3,7-dicarboxamide | 1028.3 |
| 10 | adamantan-1-yl | (S)-2-((S)-2-((3S,5S,7S)-Adamantan-1-yl)-2-((S)-2-(methylamino)propanamido)acetyl)-N$^7$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl) pyrrolidin-3-yl )-N$^3$-((R)-1,2,3,4-tetrahydronaphthalen-1-yl)-1,2,3,4-tetrahydroisoquinoline-3,7-dicarboxamide | 1066.5 |

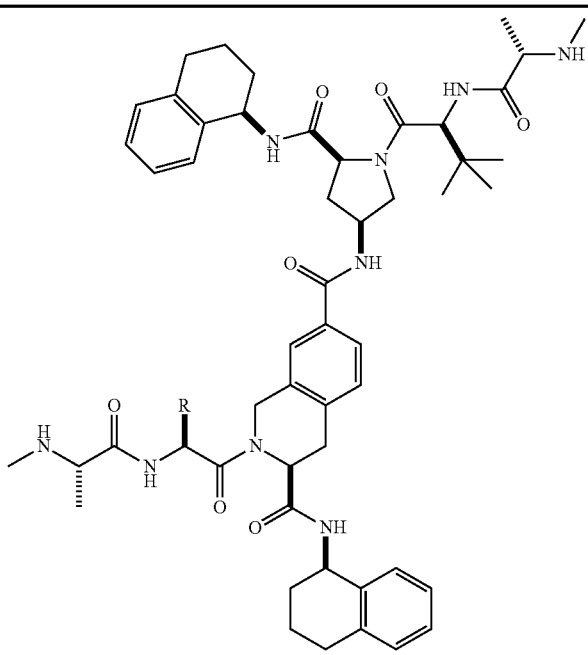

| Ex. No. | R | Name | LCMS (M + H) |
|---|---|---|---|
| 11 | 3,5-difluorobenzyl | (S)-2-((S)-3-(3,5-Difluorophenyl)-2-((S)-2-(methylamino) propanamido)propanoyl)-N⁷-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N³-((R)-1,2,3,4-tetrahydronaphthalen-1-yl)-1,2,3,4-tetrahydroisoquinoline-3,7-dicarboxamide | 1058.4 |
| 12 | cyclopentyl | (S)-2-((S)-2-Cyclopentyl-2-((S)-2-(methylamino) propanamido)acetyl)-N⁷-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N³-((R)-1,2,3,4-tetrahydronaphthalen-1-yl)-1,2,3,4-tetrahydroisoquinoline-3,7-dicarboxamide | 1000.7 |
| 13 | tetrahydro-2H-pyran-4-yl | (S)-N⁷-(3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-2-((S)-2-((S)-2-(methylamino)propanamido)-2-(tetrahydro-2H-pyran-4-yl)acetyl)-N³-((R)-1,2,3,4-tetrahydronaphthalen-1-yl)-1,2,3,4-tetrahydroisoquinoline-3,7-dicarboxamide | 1016.7 |

Examples 14 to 17

The following Examples were prepared according to the procedures described for the synthesis of Example 1.

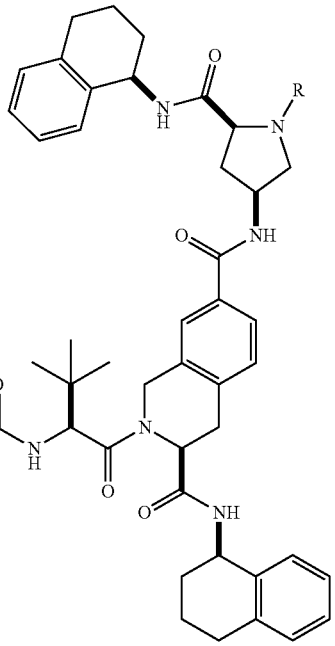

| Ex. No. | R | Name | LCMS (M + H) |
|---|---|---|---|
| 14 | | (S)-2-((S)-3,3-Dimethyl-2-((S)-2-(methylamino) propanamido)butanoyl)-N⁷-((3S,5S)-1-((S)-2-((S)-2-(ethylamino)propanamido)-3,3-dimethylbutanoyl)-5-(((R)-1,2,3,4-tetrahydronaphthalen-1-yl)carbamoyl) pyrrolidin-3-yl)-N³-((R)-1,2,3,4-tetrahydronaphthalen-1-yl)-1,2,3,4-tetrahydroisoquinoline-3,7-dicarboxamide | 1002.6 |
| 15 | | (S)-N⁷-((3S,5S)-1-((S)-3,3-Dimethyl-2-((S)-2-(methylamino)butanamido)butanoyl)-5-(((R)-1,2,3,4-tetrahydronaphthalen-1-yl)carbamoyl)pyrrolidin-3-yl)-2-((S)-3,3-dimethyl-2-((S)-2-(methylamino)propanamido) butanoyl)-N³-((R)-1,2,3,4-tetrahydronaphthalen-1-yl)-1,2,3,4-tetrahydroisoquinoline-3,7-dicarboxamide | 1002.7 |
| 16 | | (S)-2-((S)-3,3-Dimethyl-2-((S)-2-(methylamino) propanamido)butanoyl)-N⁷-((3S,5S)-1-((S)-3-ethyl-2-((S)-2-(methylamino)butanamido)pentanoyl)-5-(((R)-1,2,3,4-tetrahydronaphthalen-1-yl)carbamoyl)pyrrolidin-3-yl)-N³-((R)-1,2,3,4-tetrahydronaphthalen-1-yl)-1,2,3,4-tetrahydroisoquinoline-3,7-dicarboxamide | 1017.2 |
| 17 | | (S)-2-((S)-3,3-Dimethyl-2-((S)-2-(methylamino) propanamido)butanoyl)-N⁷-((3S,5S)-1-((S)-3-ethyl-2-((S)-2-(methylamino)propanamido)pentanoyl)-5-(((R)-1,2,3,4-tetrahydronaphthalen-1-yl)carbamoyl)pyrrolidin-3-yl)-N³-((R)-1,2,3,4-tetrahydronaphthalen-1-yl)-1,2,3,4-tetrahydroisoquinoline-3,7-dicarboxamide | 1002.8 |

Examples 18 and 19

The following Examples were prepared according to the procedures described for the synthesis of Example 1.

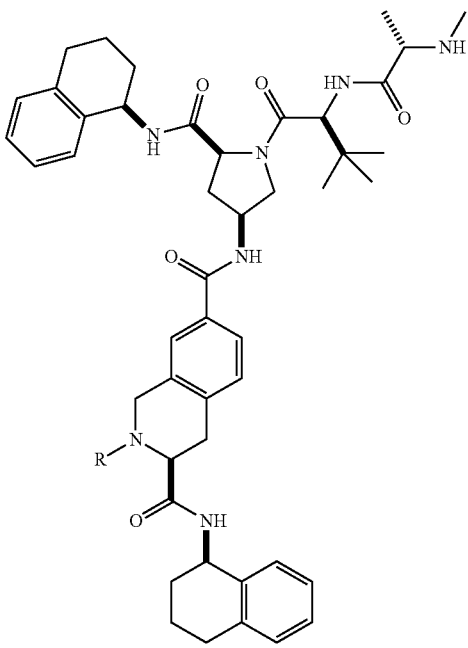

| Ex. No. | R | Name | LCMS (M + H) |
|---|---|---|---|
| 18 | ![R group] | (S)-N⁷-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-2-((S)-3-ethyl-2-((S)-2-(ethylamino)propanamido)pentanoyl)-N³-((R)-1,2,3,4-tetrahydronaphthalen-1-yl)-1,2,3,4-tetrahydroisoquinoline-3,7-dicarboxamide | 1016.6 |
| 19 | ![R group] | (S)-N⁷-((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-2-((S)-3-ethyl-2-((S)-2-(methylamino)butanamido)pentanoyl)-N³-((R)-1,2,3,4-tetrahydronaphthalen-1-yl)-1,2,3,4-tetrahydroisoquinoline-3,7-dicarboxamide | 1016.6 |

Example 20

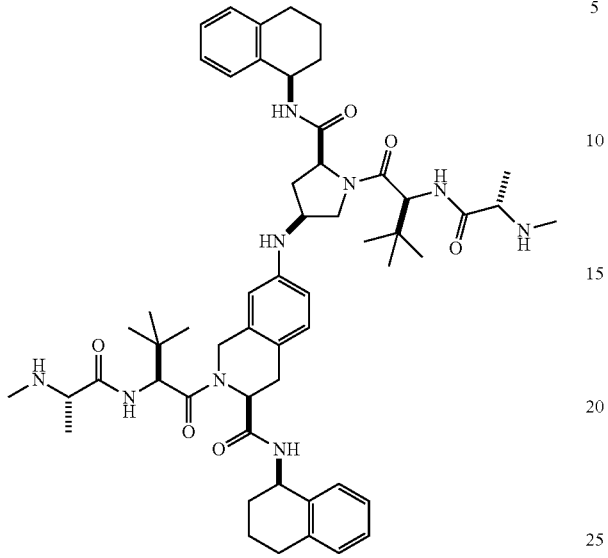

(S)-2-((S)-3,3-Dimethyl-2-((S)-2-(methylamino)
propanamido)butanoyl)-7-((((3S,5S)-1-((S)-3,3-dim-
ethyl-2-((S)-2-(methylamino)propanamido)bu-
tanoyl)-5-(((R)-1,2,3,4-tetrahydronaphthalen-1-yl)
carbamoyl)pyrrolidin-3-yl)amino)-N—((R)-1,2,3,4-
tetrahydronaphthalen-1-yl)-1,2,3,4-
tetrahydroisoquinoline-3-carboxamide

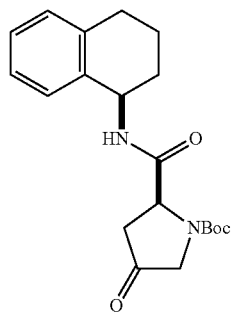

A) (S)-tert-Butyl 4-oxo-2-(((R)-1,2,3,4-tetrahy-
dronaphthalen-1-yl)carbamoyl)pyrrolidine-1-car-
boxylate Following a procedure analogous to that for the synthesis of Compound D of Example 1, (S)-1-(tert-butoxycarbonyl)-4-oxopyrrolidine-2-carboxylic acid (OmegaChem, 500 mg, 2.18 mmol) and (R)-1,2,3,4-tetrahydronaphthalen-1-amine (Alfa Aesar, 320 µL, 2.18 mmol) were converted to the title compound (782 mg, 100%). MS (ESI+) m/z 359.2 (M+H)+.

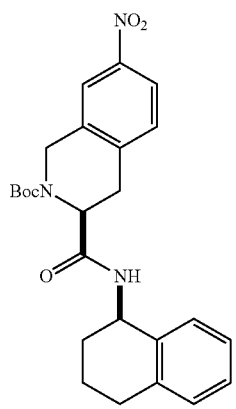

B) (S)-tert-Butyl 7-nitro-3-(((R)-1,2,3,4-tetrahy-
dronaphthalen-1-yl)carbamoyl)-3,4-dihydroiso-
quinoline-2(1H)-carboxylate To a 0° C. solution of (S)-2-(tert-butoxycarbonyl)-7-nitro-1,2,3,4-tetrahydroisoquinoline-3-carboxylic acid[1] (3.49 g, 10.8 mmol) in DMF (72 mL) was added EDC (2.49 g, 13.0 mmol) followed by HOAt (1.77 g, 13.0 mmol). After 10 min, (R)-1,2,3,4-tetrahydronaphthalen-1-amine (Alfa Aesar, 1.59 mL, 10.8 mmol) and NMM (3.57 mL, 32.5 mmol) were added, and the resulting reaction mixture was stirred warming to room temperature overnight. The reaction mixture was then diluted with EtOAc and sat. aq. NaHCO₃ solution. The aqueous layer was extracted with EtOAc (3×), and the combined organic extracts were washed with 1N HCl, water, 10% aq. LiCl solution and brine. The extracts were dried over Na₂SO₄, filtered through a pad of silica gel and concentrated in vacuo to provide the title compound (4.27 g, 87%) as a yellow solid. MS (ESI+) m/z 452.3 (M+H)+.

[1] Anderson, P. C. et al., European Patent. Application No., EP 401676 A1 (1990).

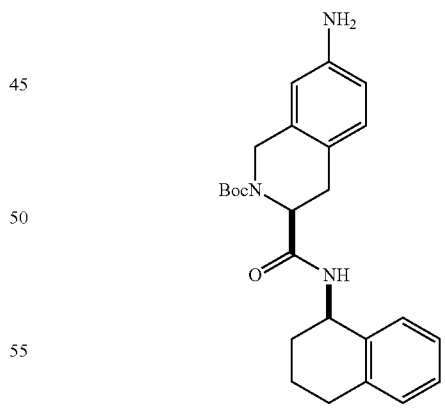

C) (S)-tert-Butyl 7-amino-3-(((R)-1,2,3,4-tetrahy-
dronaphthalen-1-yl)carbamoyl)-3,4-dihydroiso-
quinoline-2(1H)-carboxylate To a pressure flask containing 5% Pd/C (91 mg, 0.085 mg) was added a solution of (S)-tert-butyl 7-nitro-3-(((R)-1,2,3,4-tetrahydronaphthalen-1-yl)carbamoyl)-3,4-dihydroiso-quinoline-2(1H)-carboxylate (0.38 g, 0.85 mmol) in MeOH (8.5 mL). The resulting reaction mixture was stirred under 5 psi H$_2$ for 1 h and then filtered through a pad of CELITE®, rinsing with EtOAc. The filtrate was concentrated in vacuo to give the title compound (301 mg, 84%) as a colorless oil. MS (ESI$^+$) m/z 422.2 (M+H)$^+$.

organics were washed with brine, dried over Na$_2$SO$_4$, filtered and concentrated in vacuo to give the title compound (151 mg, 97%) as a colorless oil. MS (ESI$^+$) m/z 764.5 (M+H)$^+$.

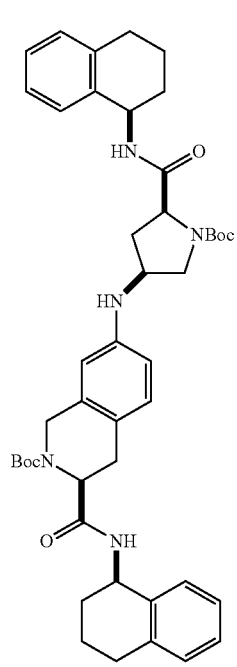

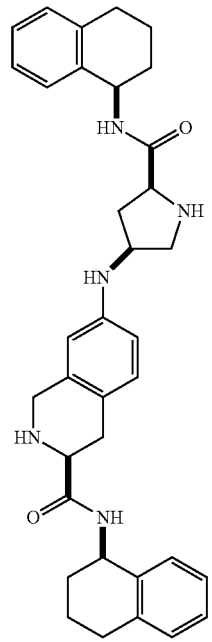

D) (S)-tert-Butyl 7-(((3S,5S)-1-(tert-butoxycarbonyl)-5-(((R)-1,2,3,4-tetrahydronaphthalen-1-yl)carbamoyl)pyrrolidin-3-yl)amino)-3-(((R)-1,2,3,4-tetrahydronaphthalen-1-yl)carbamoyl)-3,4-dihydroisoquinoline-2(1H)-carboxylate To a solution of (S)-tert-butyl 4-oxo-2-(((R)-1,2,3,4-tetrahydronaphthalen-1-yl)carbamoyl)pyrrolidine-1-carboxylate (73 mg, 0.20 mmol) in DCE (2.0 mL) was added (S)-tert-butyl 7-amino-3-(((R)-1,2,3,4-tetrahydronaphthalen-1-yl)carbamoyl)-3,4-dihydroisoquinoline-2(1H)-carboxylate (86 mg, 0.20 mmol) and AcOH (12 µL, 0.20 mmol). Na(OAc)$_3$BH (78 mg, 0.37 mmol) was then added, and the resulting reaction mixture was stirred at room temperature for 4 h. Additional AcOH (12 µL, 0.20 mmol) and Na(OAc)$_3$BH (78 mg, 0.37 mmol) were added, and stirring was continued overnight at room temperature. The reaction mixture was poured into a separatory funnel containing 1N HCl and EtOAc. The aqueous layer was extracted with EtOAc (3×). The combined E) (S)—N—((R)-1,2,3,4-Tetrahydronaphthalen-1-yl)-7-(((3S,5S)-5-(((R)-1,2,3,4-tetrahydronaphthalen-1-yl)carbamoyl)pyrrolidin-3-yl)amino)-1,2,3,4-tetrahydroisoquinoline-3-carboxamide To a solution of (S)-tert-butyl 7-(((3S,5S)-1-(tert-butoxycarbonyl)-5-(((R)-1,2,3,4-tetrahydronaphthalen-1-yl)carbamoyl)pyrrolidin-3-yl)amino)-3-(((R)-1,2,3,4-tetrahydronaphthalen-1-yl)carbamoyl)-3,4-dihydroisoquinoline-2(1H)-carboxylate (150 mg, 0.20 mmol) in CH$_2$Cl$_2$ (2.2 mL) was added TFA (303 µL, 3.93 mmol). The resulting solution was stirred at room temperature for 1 h. Additional TFA (303 µL, 3.93 mmol) was added. The reaction mixture was stirred for 2 h, then quenched carefully with sat. aq. NaHCO$_3$ solution and poured into a separatory funnel containing EtOAc. The layers were separated, and the aqueous layer was extracted with EtOAc (3×). The combined organics were washed with brine, dried over Na$_2$SO$_4$, filtered and concentrated in vacuo to give the title compound (111 mg, 100%) as a tan solid. MS (ESI$^+$) m/z 564.4 (M+H)$^+$.

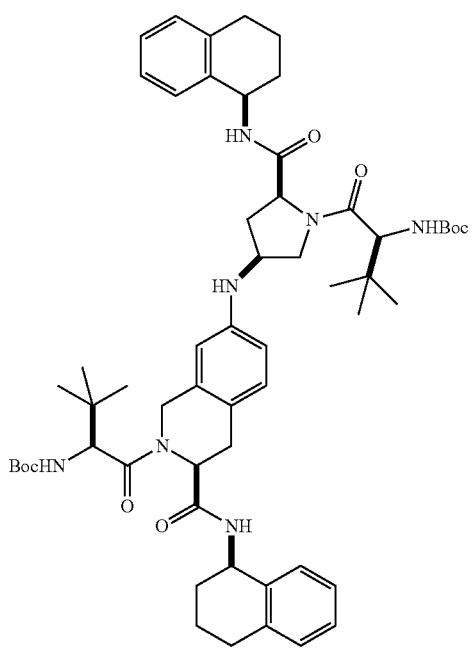

F) (S)-2-((S)-3,3-Dimethyl-2-((S)-2-((tert-butoxycarbonyl)(methylamino)propanamido)butanoyl)-7-(((3S,5S)-1-((S)-3,3-dimethyl-2-((S)-2-((tert-butoxycarbonyl)(methylamino)propanamido)butanoyl)-5-(((R)-1,2,3,4-tetrahydronaphthalen-1-yl)carbamoyl)pyrrolidin-3-yl)amino)-N—((R)-1,2,3,4-tetrahydronaphthalen-1-yl)-1,2,3,4-tetrahydroisoquinoline-3-carboxamide To a 0° C. solution of (S)-2-((tert-butoxycarbonyl)amino)-3,3-dimethylbutanoic acid (47 mg, 0.20 mmol) and (S)—N—((R)-1,2,3,4-tetrahydronaphthalen-1-yl)-7-(((3S,5S)-5-(((R)-1,2,3,4-tetrahydronaphthalen-1-yl)carbamoyl)pyrrolidin-3-yl)amino)-1,2,3,4-tetrahydroisoquinoline-3-carboxamide (55 mg, 0.10 mmol) in CH$_2$Cl$_2$ (1.0 mL) was added EDC (45 mg, 0.23 mmol) followed by HOAt (32 mg, 0.23 mmol). NMM (64 µL, 0.58 mmol) was added, and the resulting reaction mixture was stirred warming to room temperature overnight. The reaction mixture was then poured into a separatory funnel containing EtOAc and sat. aq. NaHCO$_3$ solution. The aqueous layer was extracted with EtOAc (3×). The combined organic extracts were washed with 1N HCl and brine. The extracts were dried over Na$_2$SO$_4$, filtered and concentrated in vacuo to give the title compound (93 mg, 96%) as a pale yellow oil. MS (ESI$^+$) m/z 990.6 (M+H)$^+$.

G) (S)-2-((S)-3,3-Dimethyl-2-((S)-2-(methylamino)propanamido)butanoyl)-7-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)amino)-N—((R)-1,2,3,4-tetrahydronaphthalen-1-yl)-1,2,3,4-tetrahydroisoquinoline-3-carboxamide (S)-2-((S)-3,3-Dimethyl-2-((S)-2-((tert-butoxycarbonyl)(methylamino) propanamido)butanoyl)-7-(((3S,5S)-1-((S)-3,3-dimethyl-2-((S)-2-((tert-butoxycarbonyl)(methylamino)propanamido)butanoyl)-5-(((R)-1,2,3,4-tetrahydronaphthalen-1-yl)carbamoyl)pyrrolidin-3-yl)amino)-N—((R)-1,2,3,4-tetrahydronaphthalen-1-yl)-1,2,3,4-tetrahydroisoquinoline-3-carboxamide (93 mg, 0.09 mmol) was subjected to the reaction conditions described for the synthesis of Compound E. The resulting crude oil was dissolved in DMF (1.0 mL) and cooled to 0° C. (S)-2-((tert-Butoxycarbonyl)(methyl)amino)propanoic acid (Advanced ChemTech, 40 mg, 0.20 mmol) was added followed by EDC (43 mg, 0.22 mmol) and HOAt (31 mg, 0.22 mmol). NMM (62 µL, 0.56 mmol) was then added. The resulting reaction mixture was stirred warming to room temperature over 3 h and then poured into a sep funnel containing EtOAc and sat. NaHCO$_3$. The aqueous layer was extracted with EtOAc (3×), and the combined organic extracts were washed with 1N HCl and brine. The extracts were dried over Na$_2$SO$_4$, filtered and concentrated in vacuo. The resulting crude oil was subjected to the reaction conditions described for the synthesis of Compound E to give the title compound (26 mg, 28%) after purification using prep HPLC. MS (ESI$^+$) m/z 960.6 (M+H)$^+$.

Example 21

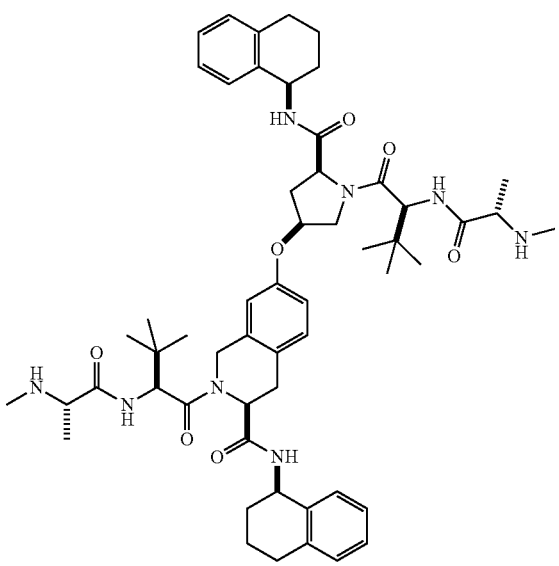

(S)-2-((S)-3,3-Dimethyl-2-((S)-2-(methylamino)
propanamido)butanoyl)-7-(((3S,5S)-1-((S)-3,3-dim-
ethyl-2-((S)-2-(methylamino)propanamido)bu-
tanoyl)-5-(((R)-1,2,3,4-tetrahydronaphthalen-1-yl)
carbamoyl)pyrrolidin-3-yl)oxy)-N—((R)-1,2,3,4-
tetrahydronaphthalen-1-yl)-1,2,3,4-
tetrahydroisoquinoline-3-carboxamide

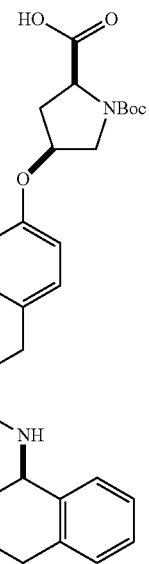

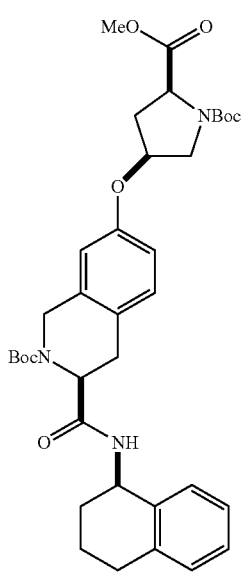

A) (2S,4S)-1-tert-Butyl 2-methyl 4-(((S)-2-(tert-
butoxycarbonyl)-3-(((R)-1,2,3,4-tetrahydronaphtha-
len-1-yl)carbamoyl)-1,2,3,4-tetrahydroisoquinolin-7-
yl)oxy)pyrrolidine-1,2-dicarboxylate To a solution of (S)-tert-butyl 7-hydroxy-3-(((R)-1,2,3,4-tetrahydronaphthalen-1-yl)carbamoyl)-3,4-dihydroisoquinoline-2(1H)-carboxylate (Compound D of Example 1, 50 mg, 0.12 mmol) in CH$_2$Cl$_2$ (1.0 mL) was added PPh$_3$ (37 mg, 0.14 mmol), (2S,4R)-1-tert-butyl 2-methyl 4-hydroxypyrrolidine-1,2-dicarboxylate (Aldrich, 35 mg, 0.14 mmol) and ADDP (37 mg, 0.14 mmol). The resulting reaction mixture was allowed to stir overnight at room temperature. Additional (2S,4R)-1-tert-butyl 2-methyl 4-hydroxypyrrolidine-1,2-dicarboxylate (35 mg, 0.14 mmol), PPh$_3$ (37 mg, 0.14 mmol) and ADDP (37 mg, 0.14 mmol) were then added. The reaction mixture was allowed to stir at room temperature for 60 h, then concentrated in vacuo and purified using flash column chromatography (gradient from 0% to 60% EtOAc/hexanes) to give the title compound (66 mg, 86%) as a colorless oil. MS (ESI$^+$) m/z 650.4 (M+H)$^+$.

B) (2S,4S)-1-(tert-Butoxycarbonyl)-4-(((S)-2-(tert-
butoxycarbonyl)-3-(((R)-1,2,3,4-tetrahydronaphtha-
len-1-yl)carbamoyl)-1,2,3,4-tetrahydroisoquinolin-7-
yl)oxy)pyrrolidine-2-carboxylic acid Following a procedure analogous to that for the synthesis of Compound K of Example 1, (2S,4S)-1-tert-butyl 2-methyl 4-(((S)-2-(tert-butoxycarbonyl)-3-(((R)-1,2,3,4-tetrahydronaphthalen-1-yl)carbamoyl)-1,2,3,4-tetrahydroisoquinolin-7-yl)oxy)pyrrolidine-1,2-dicarboxylate (66 mg, 0.10 mmol) was converted to the title compound (61 mg, 94%). MS (ESI$^+$) m/z 636.3 (M+H)$^+$.

C) (S)-2-((S)-3,3-Dimethyl-2-((S)-2-(methylamino)
propanamido)butanoyl)-7-(((3S,5S)-1-((S)-3,3-dim-
ethyl-2-((S)-2-(methylamino)propanamido)bu-
tanoyl)-5-(((R)-1,2,3,4-tetrahydronaphthalen-1-yl)
carbamoyl)pyrrolidin-3-yl)oxy)-N—((R)-1,2,3,4-
tetrahydronaphthalen-1-yl)-1,2,3,4-
tetrahydroisoquinoline-3-carboxamide Following a procedure analogous to that for the synthesis of Compound D of Example 1, (2S,4S)-1-(tert-butoxycarbonyl)-4-(((S)-2-(tert-butoxycarbonyl)-3-(((R)-1,2,3,4-tetrahydronaphthalen-1-yl)carbamoyl)-1,2,3,4-tetrahydroisoquinolin-7-yl)oxy)pyrrolidine-2-carboxylic acid (61 mg, 0.10 mmol) and (R)-1,2,3,4-tetrahydronaphthalen-1-amine (Alfa Aesar, 14 µL, 0.10 mmol) were reacted to give a crude oil, which was used without purification in the subsequent step. MS (ESI$^+$) m/z 765.5 (M+H)$^+$.

Following procedures analogous to those described for the preparation of Compounds E, F and G of Example 20, the crude oil obtained above was converted to the title compound (30 mg, 32% over 5 steps). MS (ESI+) m/z 961.3 (M+H)+.

Example 22

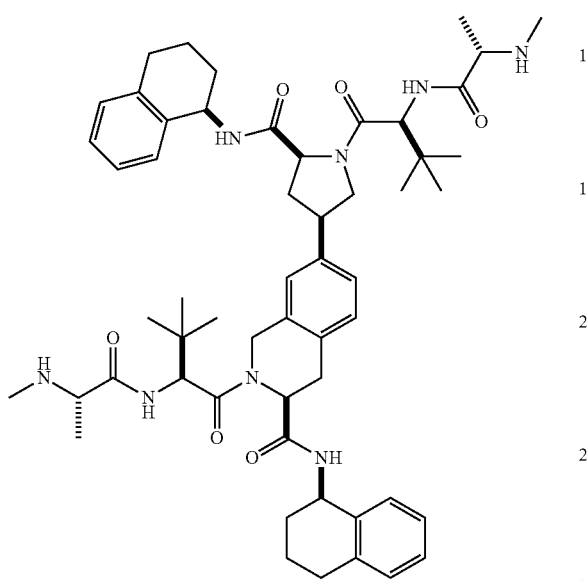

(S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N—((R)-1,2,3,4-tetrahydronaphthalen-1-yl)-1,2,3,4-tetrahydroisoquinoline-3-carboxamide

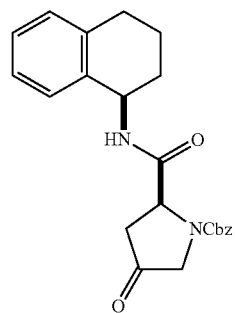

A) (S)-Benzyl 4-oxo-2-(((R)-1,2,3,4-tetrahydronaphthalen-1-yl)carbamoyl)pyrrolidine-1-carboxylate Following a procedure analogous to that for the synthesis of Compound D of Example 1, (S)-1-((benzyloxy)carbonyl)-4-oxopyrrolidine-2-carboxylic acid (Aldrich, 4.00 g, 15.2 mmol) and (R)-1,2,3,4-tetrahydronaphthalen-1-amine (Alfa Aesar, 2.23 mL, 15.2 mmol) were converted to the title compound (5.96 g, 100%). MS (ESI+) m/z 393.1 (M+H)+.

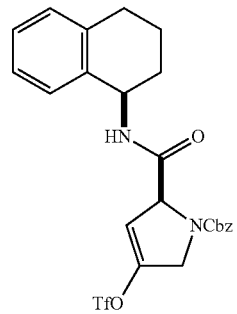

B) (S)-Benzyl 2-(((R)-1,2,3,4-tetrahydronaphthalen-1-yl)carbamoyl)-4-(((trifluoromethyl)sulfonyl)oxy)-2,5-dihydro-1H-pyrrole-1-carboxylate To a −78° C. solution of NaHMDS (2.55 mL, 2.55 mmol, 1M in THF) was added a sonicated fine suspension of (S)-benzyl 4-oxo-2-(((R)-1,2,3,4-tetrahydronaphthalen-1-yl)carbamoyl)pyrrolidine-1-carboxylate (400 mg, 1.02 mmol) in THF (1.0 mL). After 15 min, PhNTf$_2$ (728 mg, 2.04 mmol) in THF (1.6 mL) was added dropwise via syringe. The resulting reaction mixture was warmed to −10° C. over 2 h, and then quenched with sat. aq. NaHCO$_3$ solution and warmed to room temperature. The solution was poured into a separatory funnel containing EtOAc. The aqueous layer was extracted with EtOAc (3×). The combined organics were washed with brine, dried over Na$_2$SO$_4$, filtered and concentrated in vacuo to give a crude oil. Purification using flash column chromatography (gradient from 0% to 35% EtOAc/hexanes) provided the title compound (226 mg, 42%) as a colorless oil. MS (ESI+) m/z 524.9 (M+H)+.

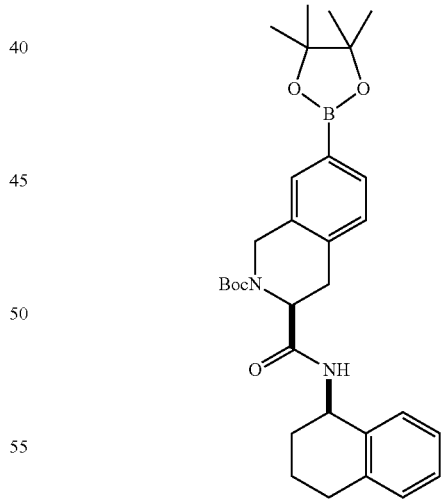

C) (S)-tert-Butyl 3-(((R)-1,2,3,4-tetrahydronaphthalen-1-yl)carbamoyl)-7-(4,4,5,5-tetramethyl-1,3,2-dioxaborolan-2-yl)-3,4-dihydroisoquinoline-2(1H)-carboxylate A solution of (S)-tert-butyl 3-(((R)-1,2,3,4-tetrahydronaphthalen-1-yl)carbamoyl)-7-(((trifluoromethyl)sulfonyl)oxy)-3,4-dihydroisoquinoline-2(1H)-carboxylate (Compound D of Example 1, 0.50 g, 0.90 mmol), KOAc (270 mg, 2.75 mmol) and 4,4,4',4',5,5,5',5''-octamethyl-2,2'-bi(1,3,2-dioxaborolane) (275 mg, 1.08 mmol) in dioxane (6.0 mL) was degassed with argon. Pd(dppf)$_2$Cl$_2$ (132 mg, 0.18 mmol) was added, and the orange reaction mixture was stirred at 85° C. overnight and then poured into a separatory funnel containing EtOAc and water. The aqueous layer was extracted with EtOAc (3×). The combined organics were washed with brine, dried over Na$_2$SO$_4$, filtered and concentrated in vacuo. The crude oil was purified using flash column chromatography (gradient from 0% to 100% EtOAc/hexanes) to give the title compound (440 mg, 92%) as a colorless oil. MS (ESI$^+$) m/z 533.2 (M+H)$^+$.

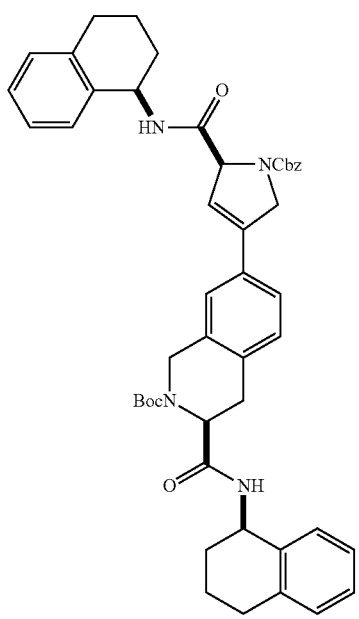

D) (S)-tert-Butyl 7-((S)-1-((benzyloxy)carbonyl)-5-(((R)-1,2,3,4-tetrahydronaphthalen-1-yl)carbamoyl)-2,5-dihydro-1H-pyrrol-3-yl)-3-(((R)-1,2,3,4-tetrahydronaphthalen-1-yl)carbamoyl)-3,4-dihydroisoquinoline-2(1H)-carboxylate A solution of (S)-benzyl 2-(((R)-1,2,3,4-tetrahydronaphthalen-1-yl)carbamoyl)-4-(((trifluoromethyl)sulfonyl)oxy)-2,5-dihydro-1H-pyrrole-1-carboxylate (226 mg, 0.43 mmol), (S)-tert-butyl 3-(((R)-1,2,3,4-tetrahydronaphthalen-1-yl)carbamoyl)-7-(4,4,5,5-tetramethyl-1,3,2-dioxaborolan-2-yl)-3,4-dihydroisoquinoline-2(1H)-carboxylate (229 mg, 0.43 mmol) and 2M aq. Na$_2$CO$_3$ (540 µL, 1.08 mmol) in dioxane (4.3 mL) was degassed with argon. Pd(Ph$_3$P)$_4$ (50 mg, 0.043 mmol) was added, and the reaction mixture was stirred at 100° C. for 2 h and then poured into a sep funnel containing sat. NH$_4$Cl. The aqueous layer was extracted with EtOAc (3×). The combined organic extracts were washed with sat. NaCl, dried over Na$_2$SO$_4$, filtered and concentrated in vacuo to give a crude oil. Purification using flash column chromatography (gradient elution from 0 to 100% EtOAc/hexanes) provided the title compound (265 mg, 79%) as a colorless oil. MS (ESI$^+$) m/z 781.2 (M+H)$^+$.

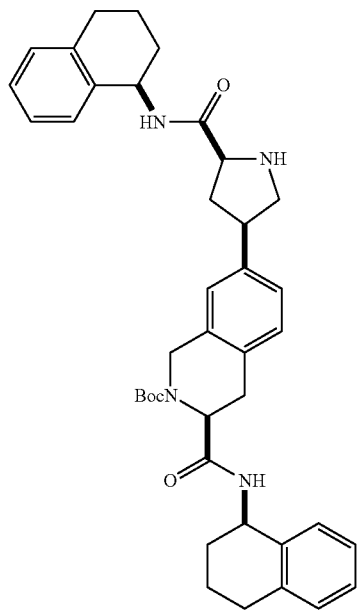

E) (S)-tert-Butyl 3-(((R)-1,2,3,4-tetrahydronaphthalen-1-yl)carbamoyl)-7-((3R,5S)-5-(((R)-1,2,3,4-tetrahydronaphthalen-1-yl)carbamoyl)pyrrolidin-3-yl)-3,4-dihydroisoquinoline-2(1H)-carboxylate Following a procedure analogous to that for the synthesis of Compound T of Example 1, tert-butyl ((S)-1-(((S)-3,3-dimethyl-1-((2S,4S)-4-(4-nitrobenzamido)-2-(((R)-1,2,3,4-tetrahydronaphthalen-1-yl)carbamoyl)pyrrolidin-1-yl)-1-oxobutan-2-yl)amino)-1-oxopropan-2-yl)(methyl)carbamate (265 mg, 0.34 mmol) was converted to the title compound (195 mg, 89%). MS (ESI$^+$) m/z 649.5 (M+H)$^+$.

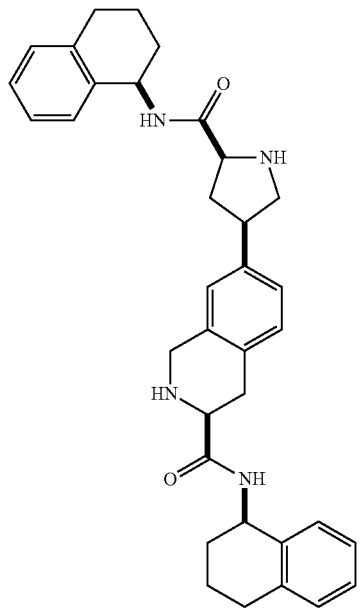

103

F) (S)—N—((R)-1,2,3,4-Tetrahydronaphthalen-1-yl)-7-((3R,5S)-5-(((R)-1,2,3,4-tetrahydronaphthalen-1-yl)carbamoyl)pyrrolidin-3-yl)-1,2,3,4-tetrahydroisoquinoline-3-carboxamide Following a procedure analogous to that for the synthesis of Compound G of Example 1, (S)-tert-butyl 3-(((R)-1,2,3,4-tetrahydronaphthalen-1-yl)carbamoyl)-7-((3R,5S)-5-(((R)-1,2,3,4-tetrahydronaphthalen-1-yl)carbamoyl)pyrrolidin-3-yl)-3,4-dihydroisoquinoline-2(1H)-carboxylate (97 mg, 0.15 mmol) was converted to the title compound (82 mg, 100%). MS (ESI$^+$) m/z 549.2 (M+H)$^+$.

G) (S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N—((R)-1,2,3,4-tetrahydronaphthalen-1-yl)-1,2,3,4-tetrahydroisoquinoline-3-carboxamide Following procedures analogous to those described for the preparation of Compounds F and G of Example 20, (S)—N—((R)-1,2,3,4-tetrahydronaphthalen-1-yl)-7-((3R,5S)-5-(((R)-1,2,3,4-tetrahydronaphthalen-1-yl)carbamoyl)pyrrolidin-3-yl)-1,2,3,4-tetrahydroisoquinoline-3-carboxamide (82, 0.15 mmol) was converted to the title compound (27 mg, 24% over 4 steps). MS (ESI$^+$) m/z 945.8 (M+H)$^+$.

Example 23

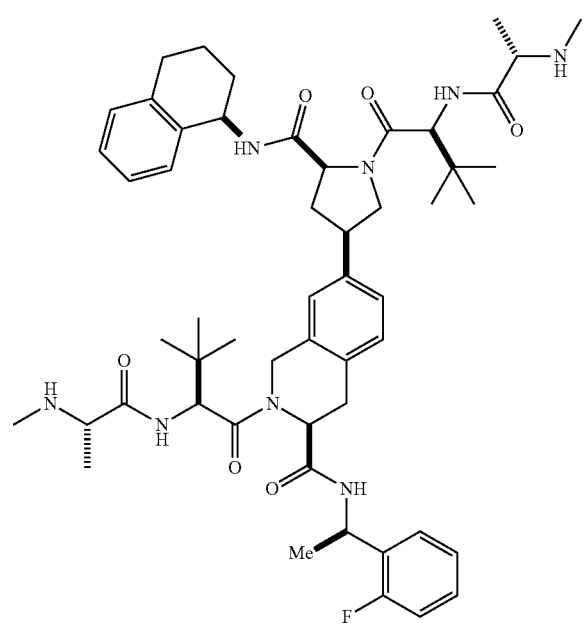

104

(S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N—((R)-1-(2-fluorophenyl)ethyl)-1,2,3,4-tetrahydroisoquinoline-3-carboxamide

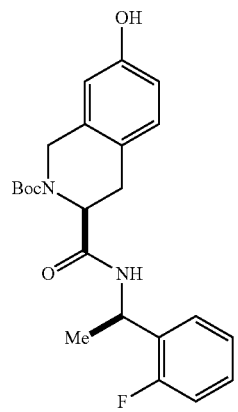 [SMILES: C[C@@H](NC(=O)[C@@H]1Cc2ccc(O)cc2CN1C(=O)OC(C)(C)C)c1ccccc1F]

A) (S)-tert-Butyl 3-(((R)-1-(2-fluorophenyl)ethyl)carbamoyl)-7-hydroxy-3,4-dihydroisoquinoline-2(1H)-carboxylate Following a procedure analogous to that for the synthesis of Compound D of Example 1, (S)-2-(tert-butoxycarbonyl)-7-hydroxy-1,2,3,4-tetrahydroisoquinoline-3-carboxylic acid (Compound C of Example 1, 750 mg, 2.56 mmol) and (R)-1-(2-fluorophenyl)ethanamine, HCl (Kingston Chemicals, 449 mg, 2.56 mmol) were converted to the title compound (760 mg, 72%). MS (ESI$^+$) m/z 415.2 (M+H)$^+$.

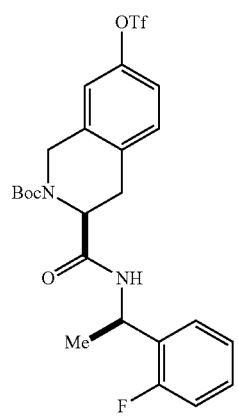 [SMILES: C[C@@H](NC(=O)[C@@H]1Cc2ccc(OS(=O)(=O)C(F)(F)F)cc2CN1C(=O)OC(C)(C)C)c1ccccc1F]

105

B) (S)-tert-Butyl 3-(((R)-1-(2-fluorophenyl)ethyl) carbamoyl)-7-((((trifluoromethyl)sulfonyl)oxy)-3,4-dihydroisoquinoline-2(1H)-carboxylate

Following a procedure analogous to that for the synthesis of Compound E of Example 1, (S)-tert-butyl 3-(((R)-1-(2-fluorophenyl)ethyl)carbamoyl)-7-hydroxy-3,4-dihydroisoquinoline-2(1H)-carboxylate (0.76 g, 1.83 mmol) was converted to the title compound (197 mg, 20%). MS (ESI+) m/z 547.0 (M+H)+.

C) (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl) carbamoyl)pyrrolidin-3-yl)-N—((R)-1-(2-fluorophenyl)ethyl)-1,2,3,4-tetrahydroisoquinoline-3-carboxamide

Following procedures analogous to those described for the synthesis of Example 22, (S)-tert-butyl 3-(((R)-1-(2-fluorophenyl)ethyl)carbamoyl)-7-((((trifluoromethyl)sulfonyl) oxy)-3,4-dihydroisoquinoline-2(1H)-carboxylate (150 mg, 0.27 mmol) was converted to the title compound (32 mg, 13% over 9 steps). MS (ESI+) m/z 937.6 (M+H)+.

Example 24

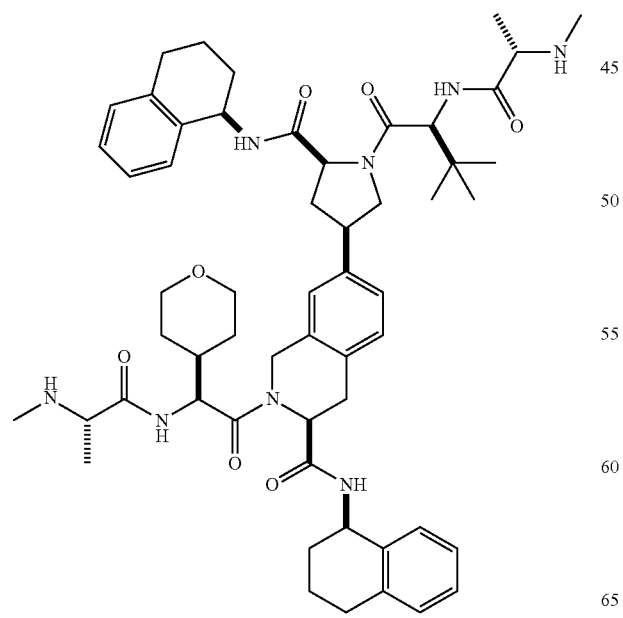

106

(S)-7-((3R,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-2-((S)-2-((S)-2-(methylamino)propanamido)-2-(tetrahydro-2H-pyran-4-yl)acetyl)-N—((R)-1,2,3,4-tetrahydronaphthalen-1-yl)-1,2,3,4-tetrahydroisoquinoline-3-carboxamide

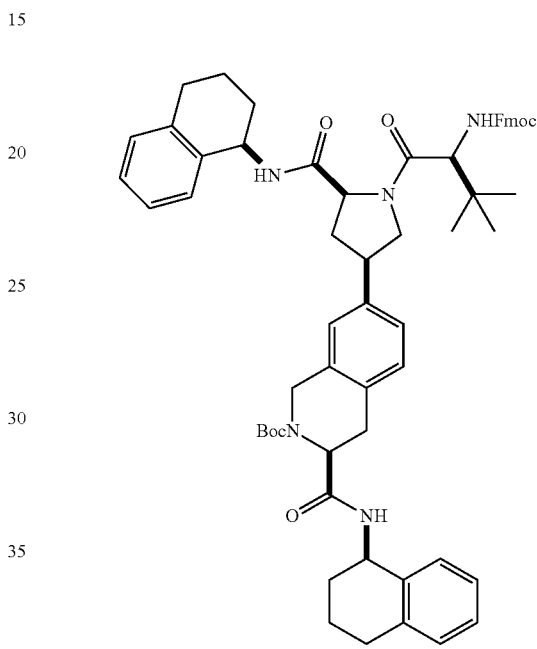

A) (S)-tert-Butyl 7-((3R,5S)-1-((S)-2-(((((9H-fluoren-9-yl)methoxy)carbonyl)amino)-3,3-dimethylbutanoyl)-5-(((R)-1,2,3,4-tetrahydronaphthalen-1-yl) carbamoyl)pyrrolidin-3-yl)-3-(((R)-1,2,3,4-tetrahydronaphthalen-1-yl)carbamoyl)-3,4-dihydroisoquinoline-2(1H)-carboxylate

Following a procedure analogous to that for the synthesis of Compound H of Example 1, (S)—N—((R)-1,2,3,4-tetrahydronaphthalen-1-yl)-7-((3R,5S)-5-(((R)-1,2,3,4-tetrahydronaphthalen-1-yl)carbamoyl)pyrrolidin-3-yl)-1,2,3,4-tetrahydroisoquinoline-3-carboxamide (Compound F of Example 15, 65 mg, 0.10 mmol) and (S)-2-(((((9H-fluoren-9-yl)methoxy)carbonyl)amino)-3,3-dimethylbutanoic acid (Chem Impex, 37 mg, 0.10 mmol) were converted to the title compound (97 mg, 98%). MS (ESI+) m/z 984.5 (M+H)+.

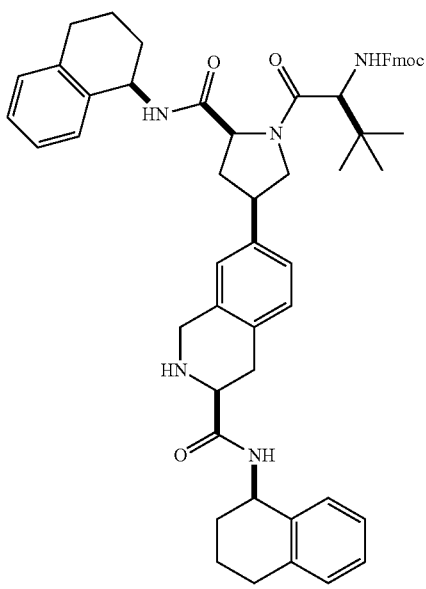

B) (9H-Fluoren-9-yl)methyl ((S)-3,3-dimethyl-1-oxo-1-((2S,4R)-2-(((R)-1,2,3,4-tetrahydronaphthalen-1-yl)carbamoyl)-4-((S)-3-(((R)-1,2,3,4-tetrahydronaphthalen-1-yl)carbamoyl)-1,2,3,4-tetrahydroisoquinolin-7-yl)pyrrolidin-1-yl)butan-2-yl)carbamate Following a procedure analogous to that for the synthesis of Compound G of Example 1, (S)-tert-butyl 7-((3R,5S)-1-((S)-2-((((9H-fluoren-9-yl)methoxy)carbonyl)amino)-3,3-dimethylbutanoyl)-5-(((R)-1,2,3,4-tetrahydronaphthalen-1-yl)carbamoyl)pyrrolidin-3-yl)-3-(((R)-1,2,3,4-tetrahydronaphthalen-1-yl)carbamoyl)-3,4-dihydroisoquinoline-2(1H)-carboxylate (97 mg, 0.10 mmol) was converted to the title compound (85 mg, 97%). MS (ESI⁺) m/z 884.4 (M+H)⁺.

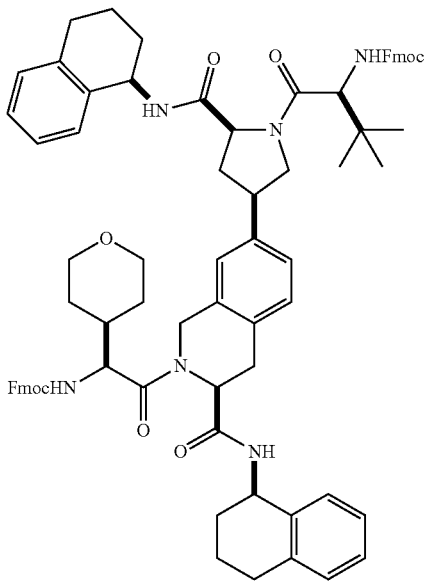

C) Fmoc Precursor I

Following a procedure analogous to that for the synthesis of Compound H of Example 1, (9H-fluoren-9-yl)methyl ((S)-3,3-dimethyl-1-oxo-1-((2S,4R)-2-(((R)-1,2,3,4-tetrahydronaphthalen-1-yl)carbamoyl)-4-((S)-3-(((R)-1,2,3,4-tetrahydronaphthalen-1-yl)carbamoyl)-1,2,3,4-tetrahydroisoquinolin-7-yl)pyrrolidin-1-yl)butan-2-yl)carbamate (85 mg, 0.096 mmol) and (S)-2-((((9H-fluoren-9-yl)methoxy)carbonyl)amino)-2-(tetrahydro-2H-pyran-4-yl)acetic acid (Amatek, 38 mg, 0.10 mmol) were converted to the title compound (78 mg, 58%). MS (ESI⁺) m/z 1248.7 (M+H)⁺.

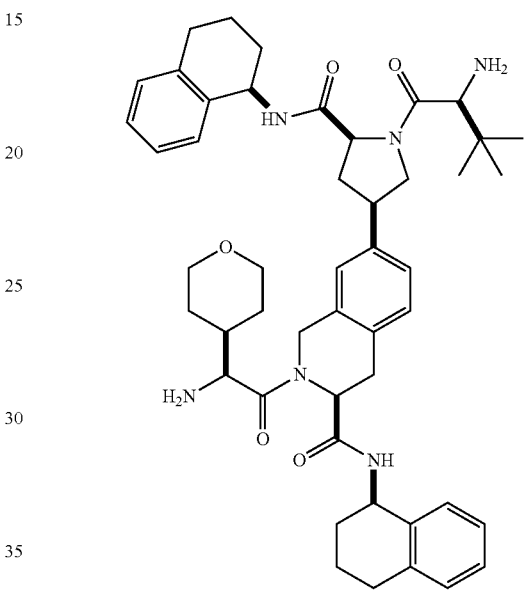

D) (S)-2-((S)-2-Amino-2-(tetrahydro-2H-pyran-4-yl)acetyl)-7-((3R,5S)-1-((S)-2-amino-3,3-dimethylbutanoyl)-5-(((R)-1,2,3,4-tetrahydronaphthalen-1-yl)carbamoyl)pyrrolidin-3-yl)-N—((R)-1,2,3,4-tetrahydronaphthalen-1-yl)-1,2,3,4-tetrahydroisoquinoline-3-carboxamide To a solution of Fmoc Precursor I (70 mg, 0.056 mmol) in CH₂Cl₂ (2.0 mL) was added piperidine (44 µL, 0.450 mmol). The resulting reaction mixture was stirred at room temperature for 1.5 h and then additional piperidine (44 µL, 0.450 mmol) was added. After stirring for 1 h at room temperature, the reaction mixture was concentrated in vacuo, then dissolved in a minimal amount of CH₂Cl₂ and filtered through a pad of silica gel washing with 50% EtOAc/hexanes (50 mL). The silica was then washed with 20% NH₃/MeOH/CH₂Cl₂ (50 mL) into a separate flask. The MeOH wash was concentrated in vacuo to give the title compound which was used crude in the subsequent experiment. MS (ESI⁺) m/z 803.5 (M+H)⁺.

E) (S)-7-((3R,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-2-((S)-2-((S)-2-(methylamino)propanamido)-2-(tetrahydro-2H-pyran-4-yl)acetyl)-N—((R)-1,2,3,4-tetrahydronaphthalen-1-yl)-1,2,3,4-tetrahydroisoquinoline-3-carboxamide Following a procedure analogous to that for the synthesis of Compound F of Example 20, (S)-2-((S)-2-amino-2-(tetrahydro-2H-pyran-4-yl)acetyl)-7-((3R,5S)-1-((S)-2-amino-3,3-dimethylbutanoyl)-5-(((R)-1,2,3,4-tetrahydronaphthalen-1-yl)carbamoyl)pyrrolidin-3-yl)-N—((R)-1,2,3,4-tetrahydronaphthalen-1-yl)-1,2,3,4-tetrahydroisoquinoline-3-carboxamide (45 mg, 0.056 mmol) and (S)-2-((tert-butoxycarbonyl)(methyl)amino)propanoic acid (24 mg, 0.12 mmol) were reacted to give a crude oil, which was subjected to the reaction conditions described for Compound E of Example 20 to provide the title compound (39 mg, 70% over 3 steps) after purification using preparative HPLC. MS (ESI$^+$) m/z 973.6 (M+H)$^+$.

Example 25

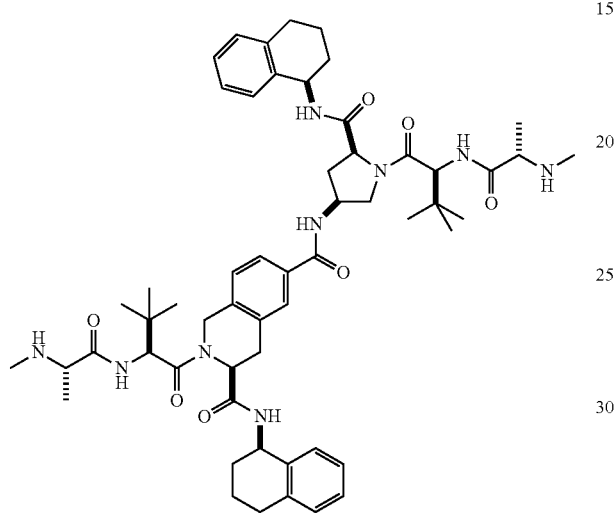

(S)-2-((S)-3,3-Dimethyl-2-((S)-2-(methylamino)propanamido)butanoyl)-N6-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N$^3$—((R)-1,2,3,4-tetrahydronaphthalen-1-yl)-1,2,3,4-tetrahydroisoquinoline-3,6-dicarboxamide Example 26

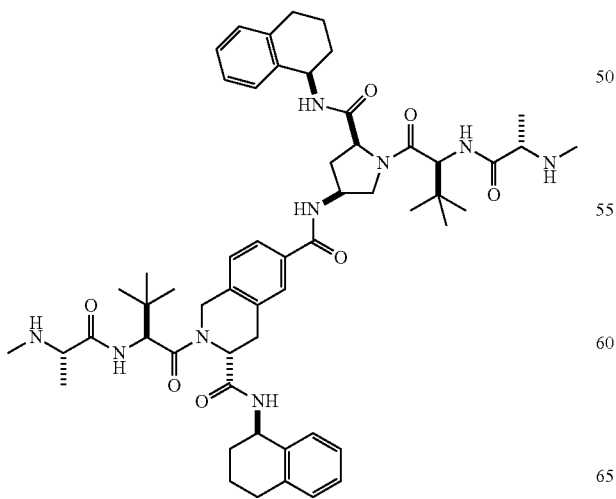

(R)-2-((S)-3,3-Dimethyl-2-((S)-2-(methylamino)propanamido)butanoyl)-N6-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N$^3$—((R)-1,2,3,4-tetrahydronaphthalen-1-yl)-1,2,3,4-tetrahydroisoquinoline-3,6-dicarboxamide

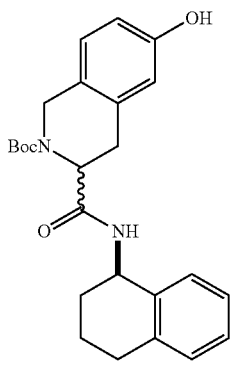

A) tert-Butyl 6-hydroxy-3-(((R)-1,2,3,4-tetrahydronaphthalen-1-yl)carbamoyl)-3,4-dihydroisoquinoline-2(1H)-carboxylate To a solution of (±)-6-hydroxy-1,2,3,4-tetrahydroisoquinoline-3-carboxylic acid (Aldrich, 500 mg, 2.59 mmol) in dioxane (11.8 mL) and water (14.2 mL) was added Boc$_2$O (678 mg, 3.11 mmol) followed by i-Pr$_2$NH (0.55 mL, 3.88 mmol). The resulting reaction mixture was stirred at room temperature for 60 h and then diluted with EtOAc and washed with 1N HCl. The aqueous layer was extracted with EtOAc (2×), and the combined organic extracts were washed with sat. NaHCO$_3$ and sat. NaCl. The extracts were dried over Na$_2$SO$_4$, filtered, concentrated in vacuo to give a crude oil which was used in the subsequent step without purification.

The crude oil from above was subjected to the reaction conditions described for the synthesis of Compound D of Example 1 to give the title compound (875 mg, 80% over 2 steps) as a white solid. MS (ESI$^+$) m/z 423.3 (M+H)$^+$.

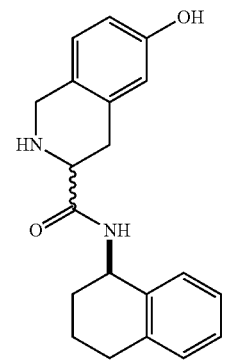

B) 6-Hydroxy-N—((R)-1,2,3,4-tetrahydronaphthalen-1-yl)-1,2,3,4-tetrahydroisoquinoline-3-carboxamide To a solution of tert-butyl 6-hydroxy-3-(((R)-1,2,3,4-tetrahydronaphthalen-1-yl)carbamoyl)-3,4-dihydroisoquinoline-2(1H)-carboxylate (875 mg, 2.07 mmol) in CH$_2$Cl$_2$ (10.4 mL) was added TFA (2.4 mL, 31.1 mmol). The resulting solution was stirred at room temperature for 2 h and then quenched with sat. NaHCO$_3$. The aqueous layer was extracted with CH$_2$Cl$_2$ (3×). The combined organic extracts were dried over Na$_2$SO$_4$, filtered and concentrated in vacuo to give the title compound (340 mg, 51%) as pale yellow solid. MS (ESI$^+$) m/z 323.2 (M+H)$^+$.

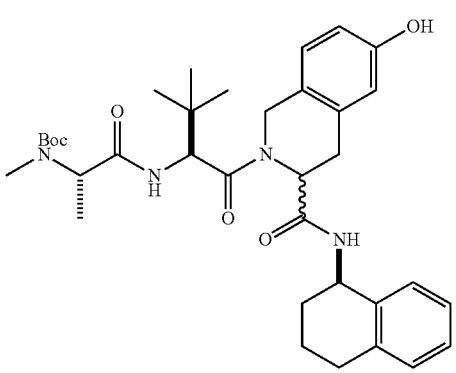

C) tert-Butyl ((2S)-1-(((2S)-1-(6-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl) carbamate Following procedures analogous to those described for the preparation of Compounds H, I and J of Example 1, 6-hydroxy-N—((R)-1,2,3,4-tetrahydronaphthalen-1-yl)-1,2,3,4-tetrahydroisoquinoline-3-carboxamide (340 mg, 1.06 mmol) was converted to the title compound (398 mg, 61% over 3 steps). MS (ESI$^+$) m/z 621.4.

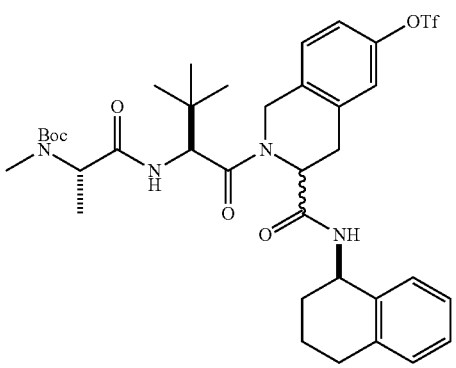

D) 2-((S)-2-((S)-2-((tert-Butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-6-yl trifluoromethanesulfonate Following a procedure analogous to that for the synthesis of Compound E of Example 1, tert-butyl ((2S)-1-(((2S)-1-(6-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (211 mg, 0.34 mmol) was converted to the title compound (126 mg, 49%). MS (ESI$^+$) m/z 753.2 (M+H)$^+$.

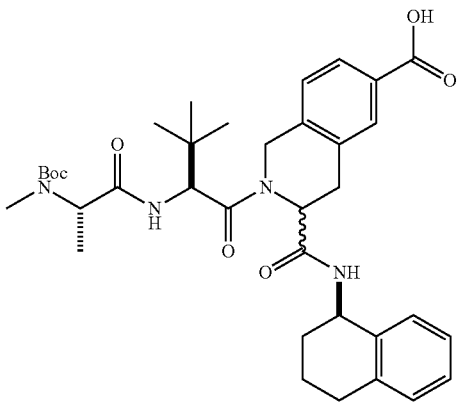

E) 2-((S)-2-((S)-2-((tert-Butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-6-carboxylic acid To a 2-neck 25 mL round bottom flask equipped with a reflux condenser was added 2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-6-yl trifluoromethanesulfonate (126 mg, 0.17 mmol) in DMF (2.0 mL) and water (0.7 mL). Pd(OAc)$_2$ (2 mg, 10.0 mol), 1,3-bis(diphenylphosphino)propane (8 mg, 0.020 mmol) and i-Pr$_2$EtN (58 µL, 0.34 mmol) were then added, and a three-way stopcock was attached to the reflux condenser with one outlet connected to a balloon filled with CO. The flask was evacuated and purged with CO (3×) and heated at 65° C. for 2 h and then at 50° C. overnight. The reaction mixture was poured into a sep funnel containing Et$_2$O and sat. NaHCO$_3$. The layers were separated and the Et$_2$O layer was extracted with sat. aq. NaHCO$_3$ solution (2×). The aqueous layer was acidified to pH=1 with 2N HCl and then extracted with EtOAc (3×). The combined organics were washed with water and sat. NaCl and then dried over MgSO$_4$. Filtration and concentration in vacuo gave the title compound (109 mg, 100%) as a colorless oil. MS (ESI$^+$) m/z 649.6 (M+H)$^+$.

F) (R)-2-((S)-3,3-Dimethyl-2-((S)-2-(methylamino)propanamido)butanoyl)-N6-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N$^3$—((R)-1,2,3,4-tetrahydronaphthalen-1-yl)-1,2,3,4-tetrahydroisoquinoline-3,6-dicarboxamide Following procedures analogous to those for the preparation of Compounds D and G of Example 1, 2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinoline-6-carboxylic acid (109 mg, 0.17 mmol) and tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl) amino)-1-oxopropan-2-yl)(methyl)carbamate (Compound O of Example 1, 94 mg, 0.17 mmol) were converted to the title compounds (32 mg, 15% and 14 mg, 7% over 2 steps, respectively) after separation of the diastereomers using preparative SFC. MS (ESI⁺) m/z 988.3 (M+H)⁺ for both.

Example 27

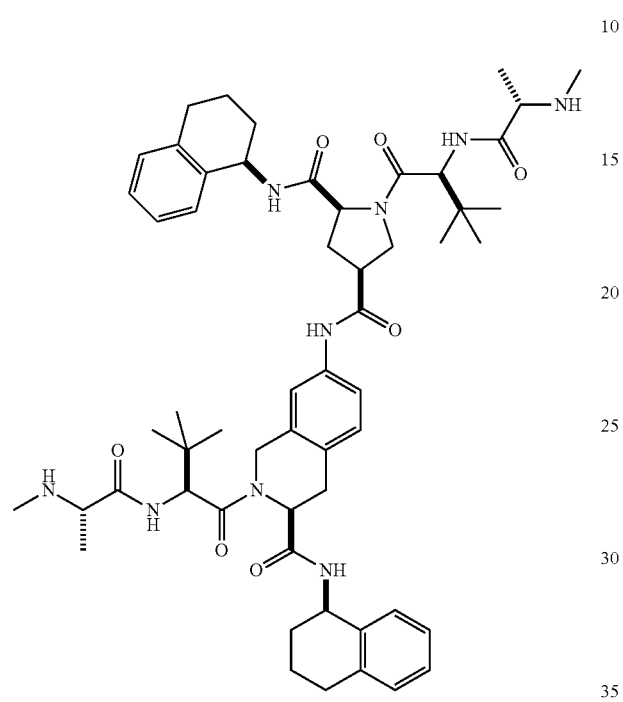

(2S,4S)-1-((S)-3,3-Dimethyl-2-((S)-2-(methylamino) propanamido)butanoyl)-N⁴—((S)-2-((S)-3,3-dimethyl-2-((S)-2-(methylamino)propanamido)butanoyl)-3-(((R)-1,2,3,4-tetrahydronaphthalen-1-yl) carbamoyl)-1,2,3,4-tetrahydroisoquinolin-7-yl)-N²— ((R)-1,2,3,4-tetrahydronaphthalen-1-yl)pyrrolidine-2,4-dicarboxamide

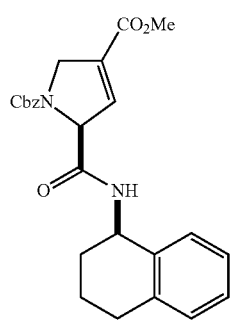

A) (S)-1-Benzyl 3-methyl 5-(((R)-1,2,3,4-tetrahydronaphthalen-1-yl)carbamoyl)-1H-pyrrole-1,3(2H, 5H)-dicarboxylate Following a procedure analogous to that for the synthesis of Compound F of Example 1, (S)-benzyl 2-(((R)-1,2,3,4-tetrahydronaphthalen-1-yl)carbamoyl)-4-(((trifluoromethyl) sulfonyl)oxy)-2,5-dihydro-1H-pyrrole-1-carboxylate (Compound B of Example 22, 250 mg, 0.48 mmol) was converted to the title compound (156 mg, 75%). MS (ESI⁺) m/z 435.3 (M+H)⁺.

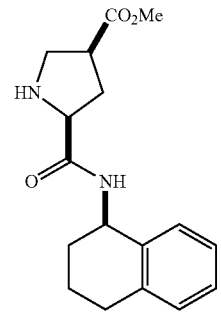

B) (3S,5S)-Methyl 5-(((R)-1,2,3,4-tetrahydronaphthalen-1-yl)carbamoyl)pyrrolidine-3-carboxylate Following a procedure analogous to that for the synthesis of Compound T of Example 1, (S)-1-benzyl 3-methyl 5-(((R)-1,2,3,4-tetrahydronaphthalen-1-yl)carbamoyl)-1H-pyrrole-1,3(2H,5H)-dicarboxylate (156 mg, 0.36 mmol) was converted to the title compound (105 mg, 97%). MS (ESI⁺) m/z 303.2 (M+H)⁺.

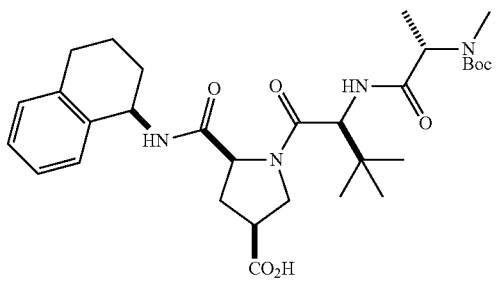

C) (3S,5S)-1-((S)-2-((S)-2-((tert-Butoxycarbonyl) (methyl)amino)propanamido)-3,3-dimethylbutanoyl)-5-(((R)-1,2,3,4-tetrahydronaphthalen-1-yl) carbamoyl)pyrrolidine-3-carboxylic acid Following procedures analogous to those described for the preparation of Compounds H, I, J and K of Example 1, (3S, 5S)-methyl 5-(((R)-1,2,3,4-tetrahydronaphthalen-1-yl)carbamoyl)pyrrolidine-3-carboxylate (105 mg, 0.35 mmol) was converted to the title compound (191 mg, 94% over 4 steps). MS (ESI⁺) m/z 587.4 (M+H)⁺.

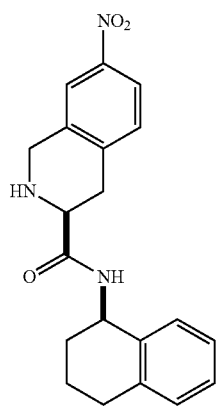

D) (S)-7-Nitro-N—((R)-1,2,3,4-tetrahydronaphthalen-1-yl)-1,2,3,4-tetrahydroisoquinoline-3-carboxamide To a solution of (S)-tert-butyl 7-nitro-3-(((R)-1,2,3,4-tetrahydronaphthalen-1-yl)carbamoyl)-3,4-dihydroisoquinoline-2(1H)-carboxylate (Compound C of Example 20, 4.45 g, 9.86 mmol) in CH$_2$Cl$_2$ (49 mL) was added TFA (11.4 mL, 148 mmol). The resulting solution was stirred at room temperature for 1 h and then quenched carefully with sat. NaHCO$_3$ until bubbling ceased. The aqueous layer was extracted with CH$_2$Cl$_2$ (3×), and the combined organic extracts were washed with sat. NaHCO$_3$, water and sat. NaCl. The extracts were dried over Na$_2$SO$_4$, filtered and concentrated in vacuo to give 3.38 g of the title compound as a pale yellow solid. $^1$H NMR (CDCl$_3$, mixture of amide rotamers) δ 8.05 (d, J=6.6 Hz, 1H), 7.97-7.88 (m, 1H), 7.53-7.32 (m, 2H), 7.22-6.94 (m, 4H), 5.25-5.03 (m, 1H), 4.18-3.94 (m, 2H), 3.83-3.65 (m, 1H), 3.35 (dd, J=16.7, 5.1 Hz, 1H), 3.09 (dd, J=17.1, 9.1 Hz, 1H), 2.90-2.70 (m, 2H), 2.18-1.96 (m, 1H), 1.93-1.44 (m, 3H); MS (ESI$^+$) m/z 352.2 (M+H)$^+$.

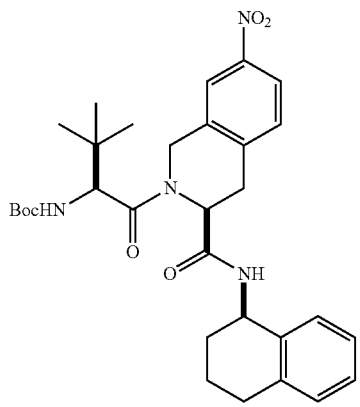

E) tert-Butyl ((S)-3,3-dimethyl-1-((S)-7-nitro-3-(((R)-1,2,3,4-tetrahydronaphthalen-1-yl)carbamoyl)-3,4-dihydroisoquinolin-2(1H)-yl)-1-oxobutan-2-yl)carbamate Following a procedure analogous to that for the synthesis of Compound D, (S)-7-nitro-N—((R)-1,2,3,4-tetrahydronaphthalen-1-yl)-1,2,3,4-tetrahydroisoquinoline-3-carboxamide (1.69 g, 4.81 mmol) and (S)-2-((tert-butoxycarbonyl)amino)-3,3-dimethylbutanoic acid (1.22 g, 5.29 mmol) were converted to the title compound (2.65 g, 98%). MS (ESI$^+$) m/z 565.3 (M+H)$^+$.

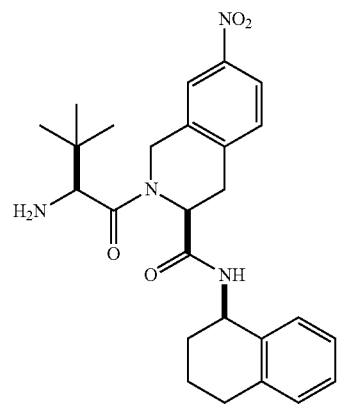

F) (S)-2-((S)-2-Amino-3,3-dimethylbutanoyl)-7-nitro-N—((R)-1,2,3,4-tetrahydronaphthalen-1-yl)-1,2,3,4-tetrahydroisoquinoline-3-carboxamide Following a procedure analogous to that for the synthesis of Compound E, tert-butyl ((S)-3,3-dimethyl-1-((S)-7-nitro-3-(((R)-1,2,3,4-tetrahydronaphthalen-1-yl)carbamoyl)-3,4-dihydroisoquinolin-2(1H)-yl)-1-oxobutan-2-yl)carbamate (2.65 g, 4.69 mmol) was converted to the title compound (2.17 g, 100%). MS (ESI$^+$) m/z 465.3 (M+H)$^+$.

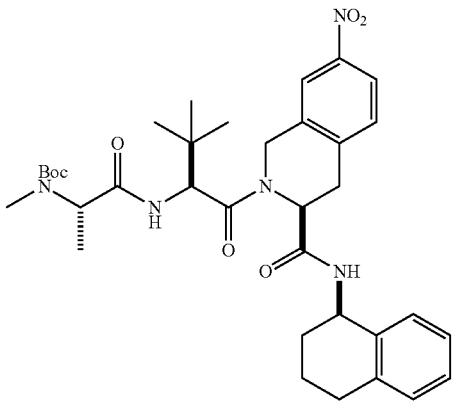

G) tert-Butyl ((S)-1-(((S)-3,3-dimethyl-1-((S)-7-nitro-3-(((R)-1,2,3,4-tetrahydronaphthalen-1-yl)carbamoyl)-3,4-dihydroisoquinolin-2(1H)-yl)-1-oxobutan-2-yl)amino)-1-oxopropan-2-yl)(methyl)carbamate Following a procedure analogous to that for the synthesis of Compound D, (S)-2-((S)-2-amino-3,3-dimethylbutanoyl)-7-nitro-N—((R)-1,2,3,4-tetrahydronaphthalen-1-yl)-1,2,3,4-tetrahydroisoquinoline-3-carboxamide (2.17 g, 4.67 mmol) and (S)-2-((tert-butoxycarbonyl)(methyl)amino)propanoic acid (Advanced ChemTech, 0.95 g, 4.67 mmol) were converted to the title compound (2.93 g, 97%). MS (ESI$^+$) m/z 650.5 (M+H)$^+$.

117

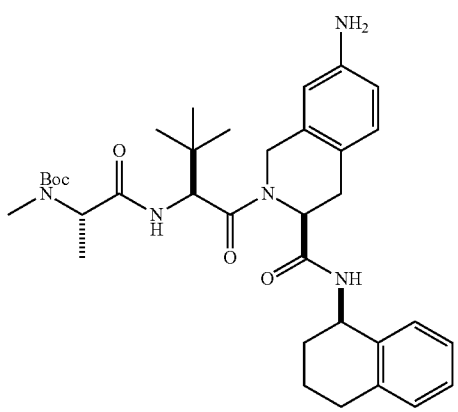

H) tert-Butyl ((S)-1-(((S)-1-((S)-7-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate To a pressure flask containing 10% Pd/C (240 mg, 0.23 mmol) was added a solution of tert-butyl ((S)-1-(((S)-3,3-dimethyl-1-((S)-7-nitro-3-(((R)-1,2,3,4-tetrahydronaphthalen-1-yl)carbamoyl)-3,4-dihydroisoquinolin-2(1H)-yl)-1-oxobutan-2-yl)amino)-1-oxopropan-2-yl)(methyl)carbamate (1.46 g, 2.25 mmol) in MeOH (11.2 mL). The resulting reaction mixture was stirred under $H_2$ at 15 psi for 3 h and then filtered through a pad of CELITE® rinsing with EtOAc. The filtrate was concentrated in vacuo and redissolved in $CH_2Cl_2$. The solution was filtered through a 0.45 µM PTFE filter and concentrated in vacuo to give the title compound (1.28 g, 92%) as a yellow solid. MS (ESI$^+$) m/z 620.4 (M+H)$^+$.

I) (2S,4S)-1-((S)-3,3-Dimethyl-2-((S)-2-(methylamino)propanamido)butanoyl)-N$^4$—((S)-2-((S)-3,3-dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)-N$^2$—((R)-1,2,3,4-tetrahydronaphthalen-1-yl)pyrrolidine-2,4-dicarboxamide Following a procedure analogous to that for the synthesis of Compound P of Example 1, (3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidine-3-carboxylic acid (Compound C, 48 mg, 0.082 mmol) and tert-butyl ((S)-1-(((S)-1-((S)-7-amino-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (51 mg, 0.082 mmol) were converted to the title compound (33 mg, 40% over 2 steps). MS (ESI$^+$) m/z 988.9 (M+H)$^+$.

Example 28

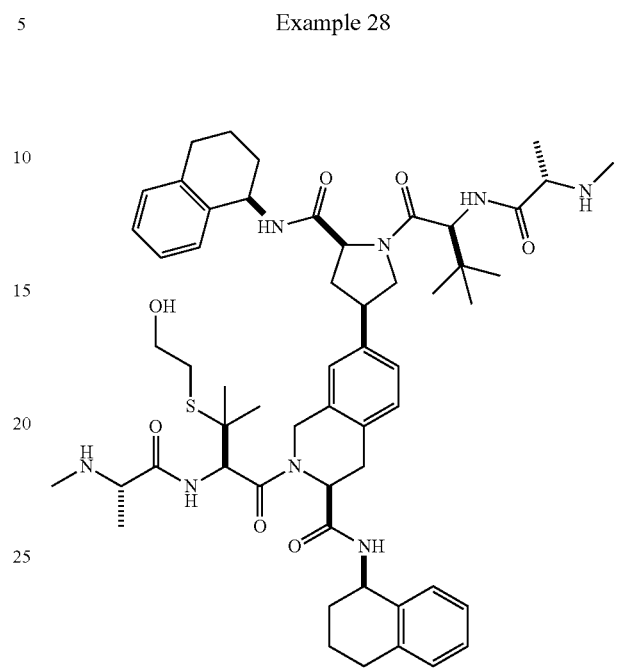

(S)-7-((3R,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-2-((R)-3-((2-hydroxyethyl)thio)-3-methyl-2-((S)-2-(methylamino)propanamido)butanoyl)-N—((R)-1,2,3,4-tetrahydronaphthalen-1-yl)-1,2,3,4-tetrahydroisoquinoline-3-carboxamide

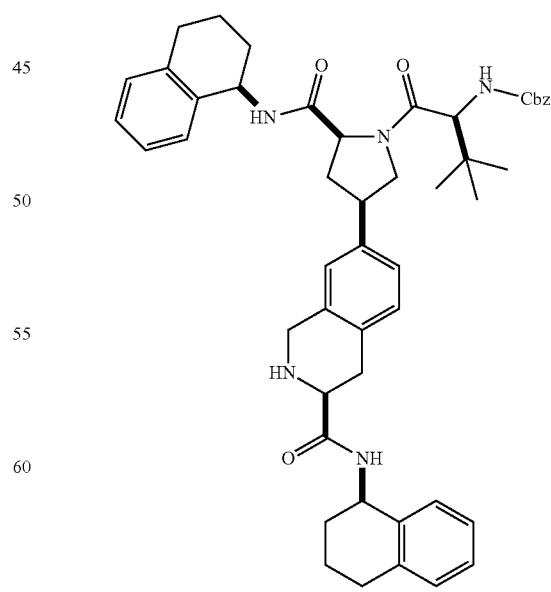

A) Benzyl ((S)-3,3-dimethyl-1-oxo-1-((2S,4R)-2-(((R)-1,2,3,4-tetrahydronaphthalen-1-yl)carbamoyl)-4-((S)-3-(((R)-1,2,3,4-tetrahydronaphthalen-1-yl)carbamoyl)-1,2,3,4-tetrahydroisoquinolin-7-yl)pyrrolidin-1-yl)butan-2-yl)carbamate (S)-2-(((Benzyloxy)carbonyl)amino)-3,3-dimethylbutanoic acid dicyclohexylammonium salt (0.40 g, 0.89 mmol) (Chem-Impex) was dissolved in EtOAc and 1 N HCl solution. The organic layer was separated, washed with brine and dried over MgSO$_4$. The filtrate was concentrated in vacuo to give the free acid. To the above acid in DMF (6 mL) were added EDC (0.17 g, 0.90 mmol) and HOAt at ice bath temperature. The reaction mixture was stirred for 10 min, followed by addition of a solution of Compound E of Example 22 (0.45 g, 0.69 mmol) in DMF (3 mL) and NMM (0.15 mL, 1.39 mmol). The resulting mixture was stirred at rt overnight. The reaction mixture was poured into a separatory funnel containing brine and EtOAc. The aqueous layer was extracted twice and the organic layers were combined, washed with sat. NaHCO$_3$ solution, and dried over MgSO$_4$. The filtrate was concentrated in vacuo. The residue was purified by flash chromatography (gradient elution from 0 to 70% EtOAc/hexanes) to afford the product (0.44 g, 71%) as a white foam. MS (ESI$^+$) m/z 896.6 (M+H)$^+$.

To a solution of (S)-tert-butyl 7-((3R,5S)-1-((S)-2-(((benzyloxy)carbonyl)amino)-3,3-dimethylbutanoyl)-5-(((R)-1,2,3,4-tetrahydronaphthalen-1-yl)carbamoyl)pyrrolidin-3-yl)-3-(((R)-1,2,3,4-tetrahydronaphthalen-1-yl)carbamoyl)-3,4-dihydroisoquinoline-2(1H)-carboxylate (0.44 g, 0.49 mmol) in DCE (5 mL) was added TFA (1.2 mL, 15.6 mmol). The reaction mixture was stirred at rt for 2 h and concentrated in vacuo. The residue was basified with sat. aq. NaHCO$_3$ solution. The resulting mixture was extracted with EtOAc (2×) and the organic layer was separated, washed with brine and dried over MgSO$_4$. The filtrate was concentrated in vacuo to give the title compound as a light yellow solid (0.35 g, 91%). MS (ESI$^+$) m/z 796.5 (M+H)$^+$.

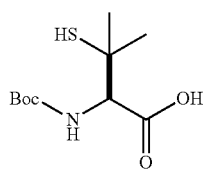

B) (R)-2-((tert-Butoxycarbonyl)amino)-3-mercapto-3-methylbutanoic acid

To a suspension of (R)-2-amino-3-mercapto-3-methylbutanoic acid (8.0 g, 53.6 mmol) in 1,4-dioxane (90 mL) was added a solution of NaOH (4.72 g, 118 mmol) in water (45 mL). The reaction mixture was then cooled with an ice bath, and at this point di-t-butyldicarbonate (14.04 g, 64.3 mmol) was added dropwise. The reaction mixture was then stirred at rt for 20 h and then extracted with EtOAc. The aqueous layer was acidified with 2N HCl solution (pH=1). The resulting aqueous layer was extracted with EtOAc (3×). The organic layer was separated and dried over MgSO$_4$. The filtrate was concentrated in vacuo and dried under vacuum to give the title compound as a white solid (11.8 g, 88%). $^1$H NMR (DMSO-d$_6$) δ 6.90 (d, J=9.2 Hz, 1H), 4.07 (d, J=9.2 Hz, 1H), 3.57 (s, 1H), 3.00 (br. s, 1H), 1.40 (s, 15H); MS (ESI$^+$) m/z 194.1 (M-56) (M+H)$^+$.

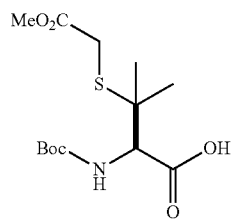 [SMILES: COC(=O)CSC(C)(C)[C@H](NC(=O)OC(C)(C)C)C(=O)O]

C) (R)-2-((tert-Butoxycarbonyl)amino)-3-((2-methoxy-2-oxoethyl)thio)-3-methylbutanoic acid To a solution of (R)-2-((tert-butoxycarbonyl)amino)-3-mercapto-3-methylbutanoic acid (4.5 g, 18.05 mmol) in THF (60 mL) was added a solution of methyl 2-bromoacetate (3.04 g, 19.85 mmol) in THF (10 mL) followed by DIPEA (9.46 mL, 54.1 mmol). The resulting mixture was stirred at rt for 4.5 h. The reaction mixture was concentrated in vacuo to remove most of the solvent, and the residue was diluted with EtOAc and sat. aq. NaHCO$_3$ solution. The aqueous layer was acidified with 1N HCl solution to adjust the pH to 2-3. The resulting aqueous layer was extracted with EtOAc (2×). The organic layers were combined and dried over MgSO$_4$. The filtrate was concentrated in vacuo to give the title compound as solid (4.8 g, 83%). $^1$H NMR (400 MHz, DMSO-d$_6$) δ 6.93 (d, J=9.0 Hz, 1H), 4.10 (d, J=9.5 Hz, 1H), 3.62 (s, 3H), 3.41 (s, 2H), 1.39 (s, 9H), 1.33 (s, 3H), 1.27 (s, 3H); MS (ESI$^+$) m/z 266.0 (M-55)$^+$.

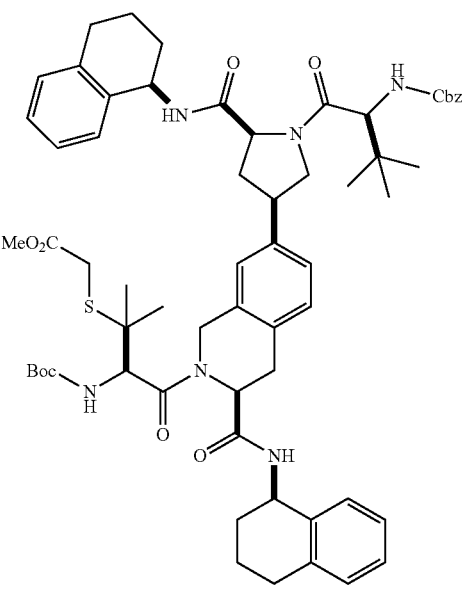

D) Methyl 2-(((R)-4-((S)-7-((3R,5S)-1-((S)-2-(((benzyloxy)carbonyl)amino)-3,3-dimethylbutanoyl)-5-(((R)-1,2,3,4-tetrahydronaphthalen-1-yl)carbamoyl)pyrrolidin-3-yl)-3-(((R)-1,2,3,4-tetrahydronaphthalen-1-yl)carbamoyl)-3,4-dihydroisoquinolin-2(1H)-yl)-3-((tert-butoxycarbonyl)amino)-2-methyl-4-oxobutan-2-yl)thio)acetate To a solution of (R)-2-((tert-butoxycarbonyl)amino)-3-((2-methoxy-2-oxoethyl)thio)-3-methylbutanoic acid (0.19 g, 0.58 mmol) in DMF (4 mL) was added HATU (0.24 g, 0.62 mmol) at ice bath temperature. The reaction mixture was stirred at 0° C. for 10 min, followed by addition of a solution of benzyl ((S)-3,3-dimethyl-1-oxo-1-((2S,4R)-2-(((R)-1,2,3,4-tetrahydronaphthalen-1-yl)carbamoyl)-4-((S)-3-(((R)-1,2,3,4-tetrahydronaphthalen-1-yl)carbamoyl)-1,2,3,4-tetrahydroisoquinolin-7-yl)pyrrolidin-1-yl)butan-2-yl)carbamate (Compound A, 0.35 g, 0.44 mmol) in DMF (2 mL) and NMM (0.08 mL, 0.71 mmol). The resulting mixture was stirred at rt for 4 h. The reaction mixture was poured into a separatory funnel containing EtOAc and brine. The organic layer was separated and washed with sat. aq. NaHCO$_3$ solution and brine successively. The organic layer was dried over MgSO$_4$ and filtered. The filtrate was concentrated in vacuo. The residue was purified by flash chromatography (gradient elution from 0 to 60% EtOAc/DCM) to afford the title compound (0.40 g, 82%) as a white foam. MS (ESI$^+$) m/z 1099.6 (M+H)$^+$.

dronaphthalen-1-yl)carbamoyl)pyrrolidin-3-yl)-3-(((R)-1,2,3,4-tetrahydronaphthalen-1-yl)carbamoyl)-3,4-dihydroisoquinolin-2(1H)-yl)-3-((tert-butoxycarbonyl)amino)-2-methyl-4-oxobutan-2-yl)thio)acetate (0.34 g, 0.35 mmol) in DCM (6 mL) was added TFA (1.2 mL, 15.6 mmol) slowly. The reaction mixture was stirred at rt for 40 min and concentrated in vacuo. The residue was basified with sat. aq. NaHCO$_3$ solution to adjust the pH to 8-9. The resulting mixture was extracted with EtOAc (2×). The organic layers were combined and washed with brine, dried over MgSO$_4$ and filtered. The filtrate was concentrated in vacuo to afford the title compound as a white solid (0.30 g, 100%). MS (ESI$^+$) m/z 865.5 (M+H)$^+$.

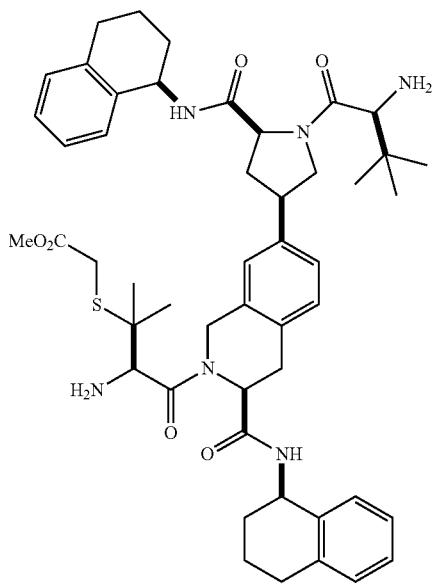

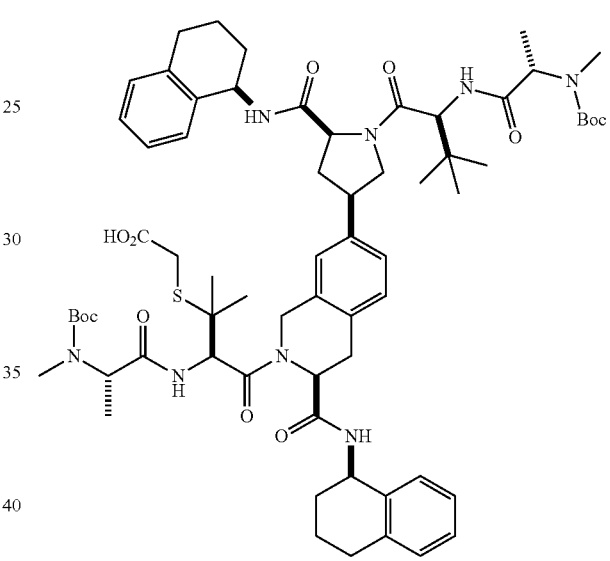

E) Methyl 2-(((R)-3-amino-4-((S)-7-((3R,5S)-1-((S)-2-amino-3,3-dimethylbutanoyl)-5-(((R)-1,2,3,4-tetrahydronaphthalen-1-yl)carbamoyl)pyrrolidin-3-yl)-3-(((R)-1,2,3,4-tetrahydronaphthalen-1-yl)carbamoyl)-3,4-dihydroisoquinolin-2(1H)-yl)-2-methyl-4-oxobutan-2-yl)thio)acetate To a solution of methyl 2-(((R)-4-((S)-7-((3R,5S)-1-((S)-2-(((benzyloxy)carbonyl)amino)-3,3-dimethylbutanoyl)-5-(((R)-1,2,3,4-tetrahydronaphthalen-1-yl)carbamoyl)pyrrolidin-3-yl)-3-(((R)-1,2,3,4-tetrahydronaphthalen-1-yl)carbamoyl)-3,4-dihydroisoquinolin-2(1H)-yl)-3-((tert-butoxycarbonyl)amino)-2-methyl-4-oxobutan-2-yl)thio)acetate (0.4 g, 0.36 mmol) in MeOH (8 mL) was added Pd(OH)$_2$ (0.20 g, 0.29 mmol). The reaction mixture was evacuated and stirred under hydrogen balloon for 6 h. The reaction mixture was filtered through a CELITER pad and the pad was washed with MeOH. The filtrate was concentrated in vacuo to give a white solid (0.34 g, 97%). MS (ESI$^+$) m/z 965.5 (M+H)$^+$.

To a solution of methyl 2-(((R)-4-((S)-7-((3R,5S)-1-((S)-2-amino-3,3-dimethylbutanoyl)-5-(((R)-1,2,3,4-tetrahy- F) (6S,9R)-9-((S)-7-((3R,5S)-1-((S)-2-((S)-2-((tert-Butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)-3-(((R)-1,2,3,4-tetrahydronaphthalen-1-yl)carbamoyl)-1,2,3,4-tetrahydroisoquinoline-2-carbonyl)-2,2,5,6,10,10-hexamethyl-4,7-dioxo-3-oxa-11-thia-5,8-diazamidecan-13-oic acid To a solution of (S)-2-((tert-butoxycarbonyl)(methyl)amino)propanoic acid (0.16 g, 0.79 mmol) in DMF (3 mL) was added EDC (0.17 g, 0.90 mmol) at ice bath temperature. After 5 min, HOAt (0.11 g, 0.82 mmol) was added. The resulting mixture was stirred at 0° C. for 5 min, followed by addition of a solution of methyl 2-(((R)-3-amino-4-((S)-7-((3R,5S)-1-((S)-2-amino-3,3-dimethylbutanoyl)-5-(((R)-1,2,3,4-tetrahydronaphthalen-1-yl)carbamoyl)pyrrolidin-3- yl)-3-(((R)-1,2,3,4-tetrahydronaphthalen-1-yl)carbamoyl)-3,4-dihydroisoquinolin-2(1H)-yl)-2-methyl-4-oxobutan-2-yl)thio)acetate (0.31 g, 0.36 mmol) in DMF (4 mL) and NMM (0.16 mL, 1.43 mmol). The reaction mixture was then stirred at rt for 1.5 h and then diluted with EtOAc and brine. The organic layer was separated and washed with sat. aq. NaHCO₃ solution and brine successively. The organic layer was dried over MgSO₄ and filtered. The filtrate was concentrated in vacuo to give a white solid (0.42 g, 95%). MS (ESI⁺) m/z 1235.7 (M+H)⁺.

To a solution of (6S,9R)-methyl 9-((S)-7-((3R,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)-3-(((R)-1,2,3,4-tetrahydronaphthalen-1-yl)carbamoyl)-1,2,3,4-tetrahydroisoquinoline-2-carbonyl)-2,2,5,6,10,10-hexamethyl-4,7-dioxo-3-oxa-11-thia-5,8-diazamidecan-13-oate (0.42 g, 0.34 mmol) in THF (3 mL) and MeOH (3 mL) was added 2N LiOH solution (1.4 mL, 2.80 mmol). The reaction mixture was stirred at rt for 1 h and then diluted with water. The pH was adjusted to 1-2 with 1N HCl solution, and the resulting mixture was extracted with EtOAc (2×). The combined organic layer was washed with brine, dried over MgSO₄ and filtered. The filtrate was concentrated in vacuo to give the title compound as a white solid (0.39 g, 94%). MS (ESI⁺) m/z 1221.7 (M+H)⁺.

G) (S)-7-((3R,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-2-((R)-3-((2-hydroxyethyl)thio)-3-methyl-2-((S)-2-(methylamino)propanamido)butanoyl)-N—((R)-1,2,3,4-tetrahydronaphthalen-1-yl)-1,2,3,4-tetrahydroisoquinoline-3-carboxamide To a solution of (6S,9R)-9-((S)-7-((3R,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)-3-(((R)-1,2,3,4-tetrahydronaphthalen-1-yl)carbamoyl)-1,2,3,4-tetrahydroisoquinoline-2-carbonyl)-2,2,5,6,10,10-hexamethyl-4,7-dioxo-3-oxa-11-thia-5,8-diazamidecan-13-oic acid (50 mg, 0.041 mmol) in THF (4 mL) were added di(1H-imidazol-1-yl)methanone (27 mg, 0.16 mmol) at rt. The reaction mixture was stirred at 50° C. for 1.5 h. At this point, NaBH₄ (10 mg, 0.25 mmol) and a few drops of water was added. The reaction mixture was stirred at rt for 30 min. To the reaction mixture was added 2 mL of water and the mixture was stirred for 20 min. The resulting mixture was extracted with EtOAc. The organic layer was washed with saturated aq. NaHCO₃ solution and dried over MgSO₄. The filtrate was concentrated in vacuo to give a white solid (40 mg, 81%). MS (ESI⁺) m/z 1207.6 (M+H)⁺.

The crude solid from above (40 mg, 0.033 mmol) was dissolved in DCM (2 mL) TFA (0.5 mL, 6.5 mmol) was added. The reaction mixture was stirred at rt for 40 min and concentrated in vacuo. The residue was purified by preparative HPLC and lyophilized to afford the title compound as a white solid (35 mg, 98%). MS (ESI⁺) m/z 1007.5 (M+H)⁺.

Example 29

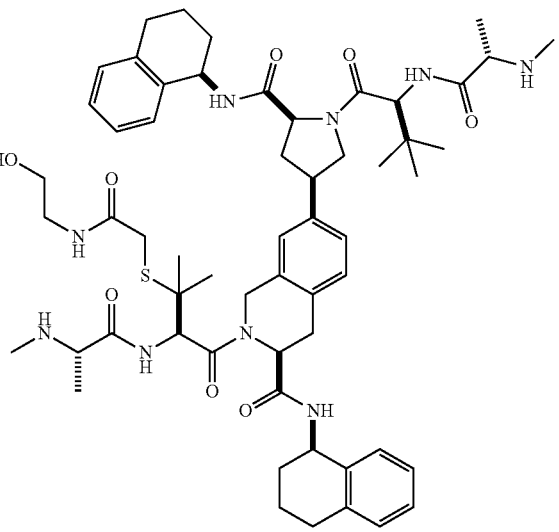

(S)-7-((3R,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-2-((R)-3-((2-((2-hydroxyethyl)amino)-2-oxoethyl)thio)-3-methyl-2-((S)-2-(methylamino)propanamido)butanoyl)-N—((R)-1,2,3,4-tetrahydronaphthalen-1-yl)-1,2,3,4-tetrahydroisoquinoline-3-carboxamide To a solution of Compound F of Example 28 (80 mg, 0.065 mmol) in DMF (2 mL) was added HATU (40 mg, 0.11 mmol). The reaction mixture was stirred at rt for 10 min, and then 2-aminoethanol (16 mg, 0.26 mmol) and NMM (0.014 mL, 0.13 mmol) were added. The resulting mixture was stirred at rt for 1 h. The reaction mixture was concentrated in vacuo and purified by preparative HPLC to give a white solid (48 mg, 58%). MS (ESI⁺) m/z 1264.7 (M+H)⁺.

To a solution of the above product (45 mg, 0.036 mmol) in DCM (3 mL) was added HCl (4N solution in dioxane, 1 mL, 4.0 mmol) dropwise. The reaction mixture was stirred at rt for 50 min. The reaction mixture was then concentrated in vacuo, and the residue was purified by preparative HPLC and then lyophilized to afford the title compound as a white solid (39 mg, 84%). MS (ESI⁺) m/z 1064.7 (M+H)⁺.

Examples 30 and 31

The following Examples were prepared according to the procedures described for the synthesis of Example 29.

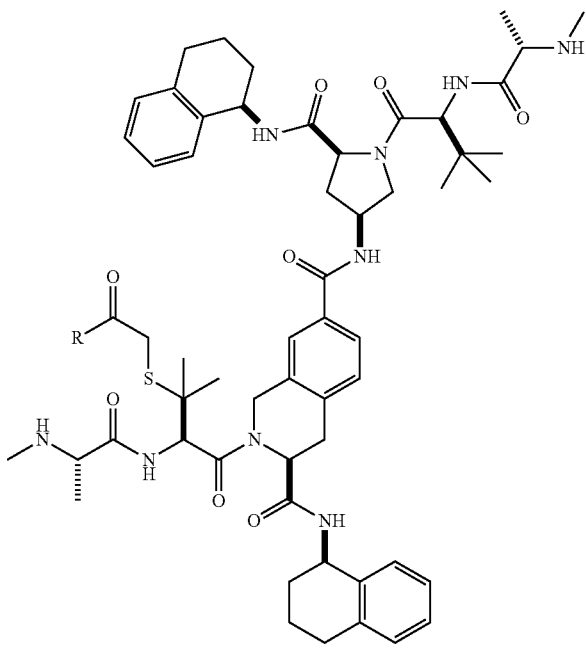

| Ex. No. | R | Name | LCMS (M + H) |
|---|---|---|---|
| 30 | 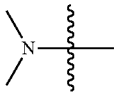 [SMILES: *N(C)C] | (S)-7-((3R,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-2-((R)-3 -((2-(dimethylamino)-2-oxoethyl)thio)-3-methyl-2-((S)-2-(methylamino)propanamido)butanoyl)-N-((R)-1,2,3,4-tetrahydronaphthalen-1-yl)-1,2,3,4-tetrahydroisoquinoline-3-carboxamide | 1048.5 |
| 31 | 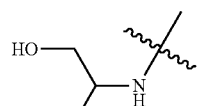 | (S)-2-((R)-3-((2-((1,3-Dihydroxypropan-2-yl)amino)-2-oxoethyl)thio)-3-methyl-2-((S)-2-(methylamino)propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N-((R)-1,2,3,4-tetrahydronaphthalen-1-yl)-1,2,3,4-tetrahydroisoquinoline-3-carboxamide | 1094.7 |

Example 32

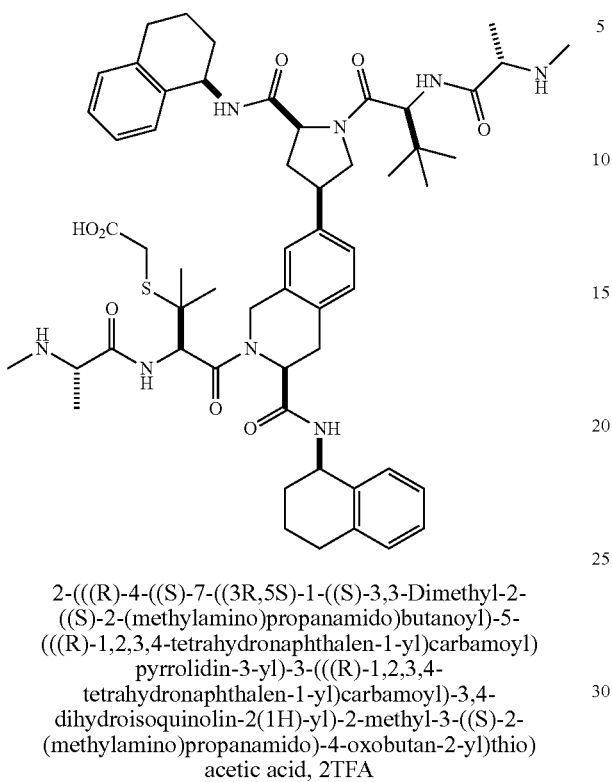

2-(((R)-4-((S)-7-((3R,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)-3-(((R)-1,2,3,4-tetrahydronaphthalen-1-yl)carbamoyl)-3,4-dihydroisoquinolin-2(1H)-yl)-2-methyl-3-((S)-2-(methylamino)propanamido)-4-oxobutan-2-yl)thio)acetic acid, 2TFA A solution of TFA (20% in $CH_2Cl_2$, 1.06 mmol) was added to Compound F of Example 28 (13 mg, 0.011 mmol). The resulting reaction mixture was stirred at room temperature for 1 h and then concentrated in vacuo. The crude oil was purified by preparative HPLC to give the title compound (2.5 mg, 18%) as a white solid after lyophilization. MS (ESI$^+$) m/z 1021.6 (M+H)$^+$.

Example 33

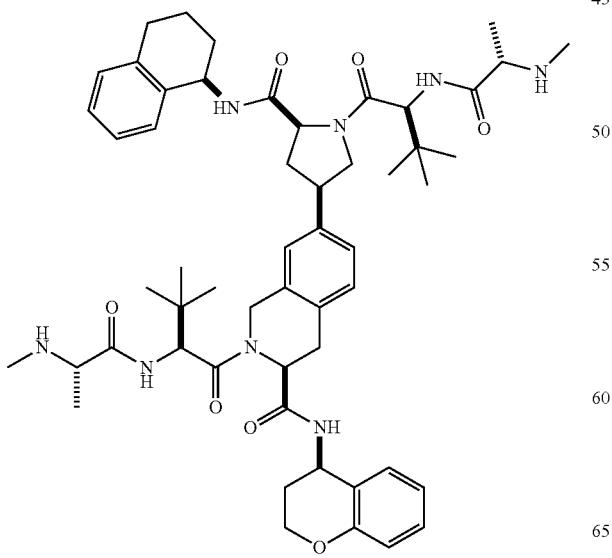

(S)—N—((R)—Chroman-4-yl)-2-((S)-3,3-dimethyl-2-((S)-2-(methylamino)propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-1,2,3,4-tetrahydroisoquinoline-3-carboxamide

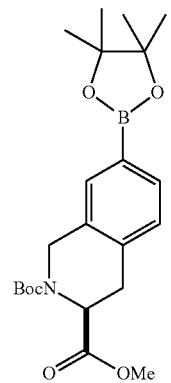

A) (S)-2-tert-Butyl 3-methyl 7-(4,4,5,5-tetramethyl-1,3,2-dioxaborolan-2-yl)-3,4-dihydroisoquinoline-2,3(1H)-dicarboxylate Following a procedure analogous to that for the synthesis of Compound C of Example 22, (S)-2-tert-butyl 3-methyl 7-(((trifluoromethyl)sulfonyl)oxy)-3,4-dihydroisoquinoline-2,3(1H)-dicarboxylate[2] (3.00 g, 6.83 mmol) was converted to the title compound (2.78 g, 98%). $^1$H NMR (CDCl$_3$, mixture of rotamers) δ 7.73-7.52 (m, 2H), 7.16 (d, J=7.5 Hz, 1H), 5.14 (dd, J=5.9, 3.1 Hz, 0.5H), 4.89-4.65 (m, 1.5H), 4.61-4.39 (m, 1H), 3.65-3.57 (m, 3H), 3.32-3.07 (m, 2H), 1.52 (s, 6H), 1.46 (s, 3H), 1.34 (s, 12H). MS (ESI$^+$) m/z 418.3 (M+H)$^+$.

[2] Ohta, M. et al., *Chem. Pharm. Bull.*, 58:1066-1076 (2010).

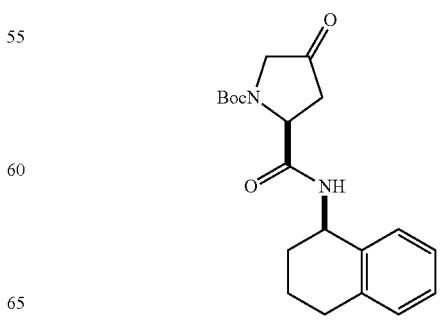

B) (S)-tert-Butyl 4-oxo-2-(((R)-1,2,3,4-tetrahydronaphthalen-1-yl)carbamoyl)pyrrolidine-1-carboxylate Following a procedure analogous to that for the synthesis of Compound A of Example 22, (S)-1-(tert-butoxycarbonyl)-4-oxopyrrolidine-2-carboxylic acid (Chem-Impex, 4.33 g, 18.89 mmol) was converted to the title compound (6.77 g, 100%). MS (ESI⁺) m/z 359.3 (M+H)⁺.

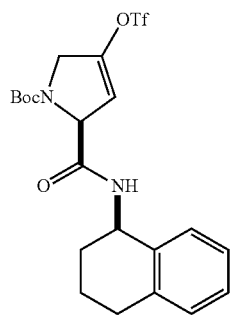

C) (S)-tert-Butyl 2-(((R)-1,2,3,4-tetrahydronaphthalen-1-yl)carbamoyl)-4-(((trifluoromethyl)sulfonyl)oxy)-2,5-dihydro-1H-pyrrole-1-carboxylate Following a procedure analogous to that for the synthesis of Compound B of Example 22, (S)-tert-butyl 4-oxo-2-(((R)-1,2,3,4-tetrahydronaphthalen-1-yl)carbamoyl)pyrrolidine-1-carboxylate (3.38 g, 9.43 mmol) was converted to the title compound (2.82 g, 61%). MS (ESI⁺) m/z 491.2 (M+H)⁺.

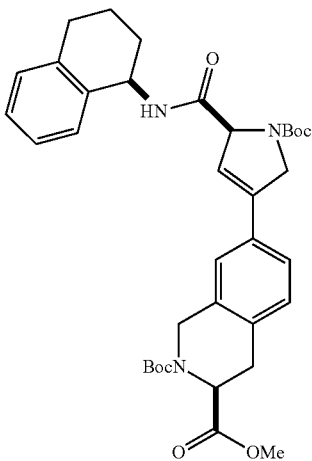

D) (S)-2-tert-Butyl 3-methyl 7-((S)-1-(tert-butoxycarbonyl)-5-(((R)-1,2,3,4-tetrahydronaphthalen-1-yl)carbamoyl)-2,5-dihydro-1H-pyrrol-3-yl)-3,4-dihydroisoquinoline-2,3(1H)-dicarboxylate Following a procedure analogous to that for the synthesis of Compound D of Example 22, (S)-tert-butyl 2-(((R)-1,2,3,4-tetrahydronaphthalen-1-yl)carbamoyl)-4-(((trifluoromethyl)sulfonyl)oxy)-2,5-dihydro-1H-pyrrole-1-carboxylate (683 mg, 1.39 mmol) and (S)-2-tert-butyl 3-methyl 7-(4,4,5,5-tetramethyl-1,3,2-dioxaborolan-2-yl)-3,4-dihydroisoquinoline-2,3(1H)-dicarboxylate (726 mg, 1.74 mmol) were converted to the title compound (730 mg, 83%). MS (ESI⁺) m/z 632.5 (M+H)⁺.

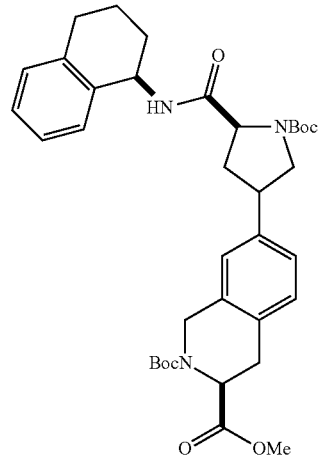

E) (S)-2-tert-Butyl 3-methyl 7-((3R,5S)-1-(tert-butoxycarbonyl)-5-(((R)-1,2,3,4-tetrahydronaphthalen-1-yl)carbamoyl)pyrrolidin-3-yl)-3,4-dihydroisoquinoline-2,3(1H)-dicarboxylate Following a procedure analogous to that for the synthesis of Compound E of Example 22, (S)-2-tert-butyl 3-methyl 7-((S)-1-(tert-butoxycarbonyl)-5-(((R)-1,2,3,4-tetrahydronaphthalen-1-yl)carbamoyl)-2,5-dihydro-1H-pyrrol-3-yl)-3,4-dihydroisoquinoline-2,3(1H)-dicarboxylate (730 mg, 1.16 mmol) was converted to the title compound (650 mg, 89%). MS (ESI⁺) m/z 634.5 (M+H)⁺.

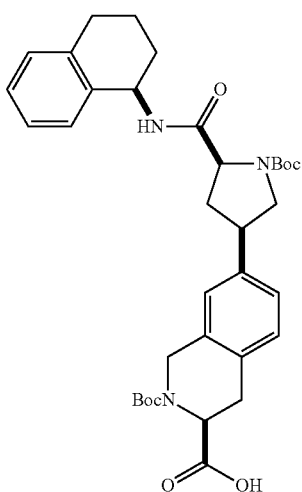

F) (S)-2-(tert-Butoxycarbonyl)-7-((3R,5S)-1-(tert-butoxycarbonyl)-5-(((R)-1,2,3,4-tetrahydronaphthalen-1-yl)carbamoyl)pyrrolidin-3-yl)-1,2,3,4-tetrahydroisoquinoline-3-carboxylic acid Following a procedure analogous to that for the synthesis of Compound K of Example 1, (S)-2-tert-butyl 3-methyl 7-((3R,5S)-1-(tert-butoxycarbonyl)-5-(((R)-1,2,3,4-tetrahydronaphthalen-1-yl)carbamoyl)pyrrolidin-3-yl)-3,4-dihydroisoquinoline-2,3(1H)-dicarboxylate (650 mg, 1.03 mmol) was converted to the title compound (599 mg, 94%). MS (ESI+) m/z 620.5 (M+H)+.

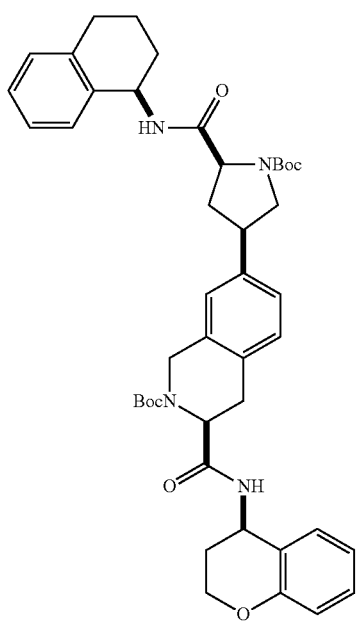

G) (S)-tert-Butyl 7-((3R,5S)-1-(tert-butoxycarbonyl)-5-(((R)-1,2,3,4-tetrahydronaphthalen-1-yl)carbamoyl)pyrrolidin-3-yl)-3-((R)-chroman-4-ylcarbamoyl)-3,4-dihydroisoquinoline-2(1H)-carboxylate Following a procedure analogous to that for the synthesis of Compound D of Example 1, (S)-2-(tert-butoxycarbonyl)-7-((3R,5S)-1-(tert-butoxycarbonyl)-5-(((R)-1,2,3,4-tetrahydronaphthalen-1-yl)carbamoyl)pyrrolidin-3-yl)-1,2,3,4-tetrahydroisoquinoline-3-carboxylic acid (60 mg, 0.10 mmol) and (R)-chroman-4-amine[3], HCl (18 mg, 0.10 mmol) were converted to the title compound (70 mg, 97%). MS (ESI+) m/z 751.6 (M+H)+.

[3] Guijarro, D. et al., J. Org. Chem., 75:5265-5270 (2010).

H) (S)—N—((R)-Chroman-4-yl)-2-((S)-3,3-dimethyl-2-((S)-2-(methylamino)propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-1,2,3,4-tetrahydroisoquinoline-3-carboxamide Following procedures analogous to those described for the preparation of Compounds E, F and G of Example 20, (S)-tert-butyl 7-((3R,5S)-1-(tert-butoxycarbonyl)-5-(((R)-1,2,3,4-tetrahydronaphthalen-1-yl)carbamoyl)pyrrolidin-3-yl)-3-((R)-chroman-4-ylcarbamoyl)-3,4-dihydroisoquinoline-2(1H)-carboxylate (70 mg, 0.094 mmol) was converted to the title compound (29 mg, 31% over 5 steps). MS (ESI+) m/z 947.7 (M+H)+.

Examples 34 to 40

The following Examples were prepared according to the procedures described for the synthesis of Example 33.

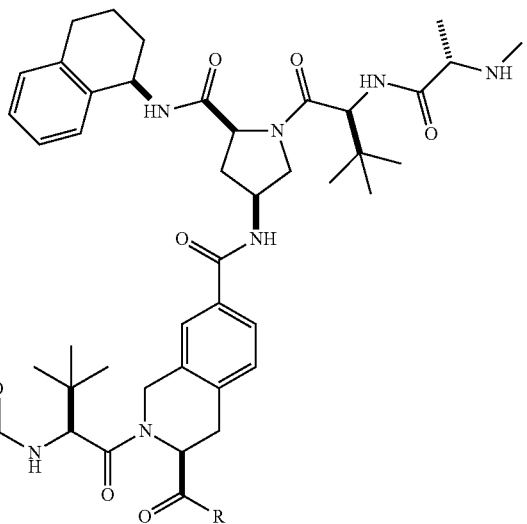

| Ex. No. | R | Name | LCMS (M + H) |
|---|---|---|---|
| 34 | | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3- yl)-N-((S)-1-hydroxy-3-phenylpropan-2-yl)-1,2,3,4-tetrahydroisoquinoline-3-carboxamide | 949.8 |
| 35 | | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3- yl)-N-((S)-1-(2-fluorophenyl)-2-hydroxyethyl)-1,2,3,4-tetrahydroisoquinoline-3-carboxamide | 953.7 |
| 36 | | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3- yl)-N-((R)-1-(2-fluorophenyl)-2-hydroxyethyl)-1,2,3,4-tetrahydroisoquinoline-3-carboxamide | 953.7 |
| 37 | | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N-((R)-6-methoxy-1,2,3,4-tetrahydronaphthalen-1-yl)-1,2,3,4-tetrahydroisoquinoline-3-carboxamide | 975.5 |

-continued

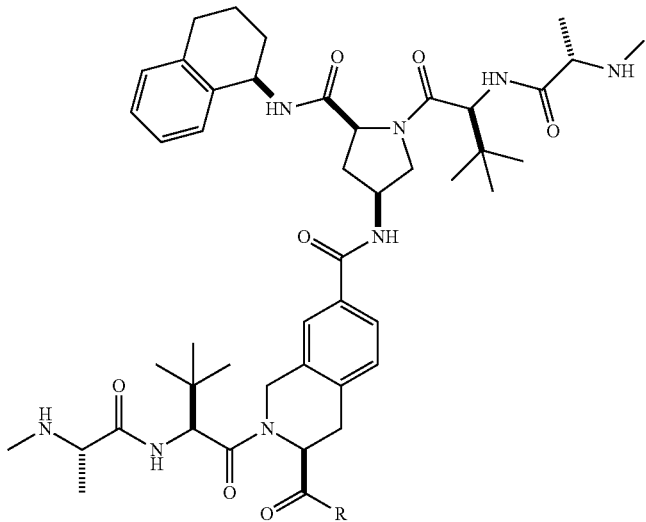

| Ex. No. | R | Name | LCMS (M + H) |
|---|---|---|---|
| 38 | ![R group with pyrazole-phenyl] | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N-(3-methyl-1-phenyl-1H-pyrazol-5-yl)-1,2,3,4-tetrahydroisoquinoline-3-carboxamide | 971.7 |
| 39 | ![R group with methoxy-benzyl] | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N-((S)-1-methoxy-3-phenylpropan-2-yl)-1,2,3,4-tetrahydroisoquinoline-3-carboxamide | 963.7 |
| 40 | ![R group with methyl ester benzyl] | (S)-Methyl 2-((S)-2-((S)-3,3-dimethyl-2-((S)-2-(methylamino)propanamido)butanoyl)-7-((3R,5S)-1-((S)-3,3-dimethyl-2-((S)-2-(methylamino)propanamido) butanoyl)-5-(((R)-1,2,3,4-tetrahydronaphthalen-1-yl)carbamoyl)pyrrolidin-3-yl)-1,2,3,4-tetrahydroisoquinoline-3-carboxamido)-3-phenylpropanoate | 977.7 |

Example 41

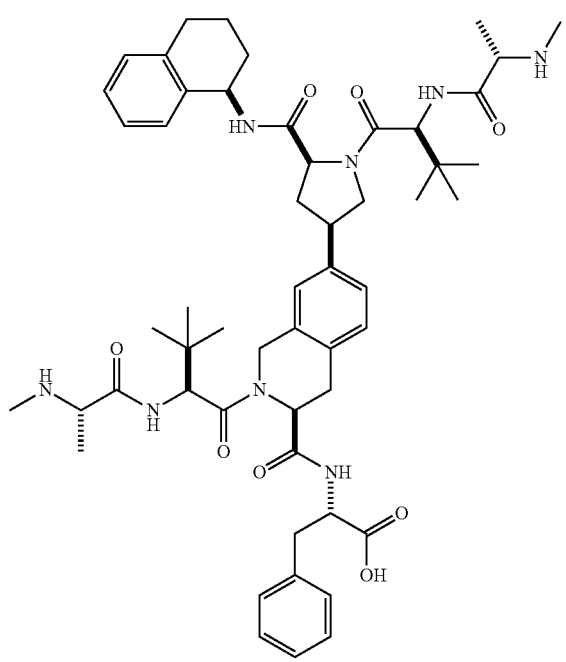

(S)-2-((S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-1,2,3,4-tetrahydroisoquinoline-3-carboxamido)-3-phenylpropanoic acid

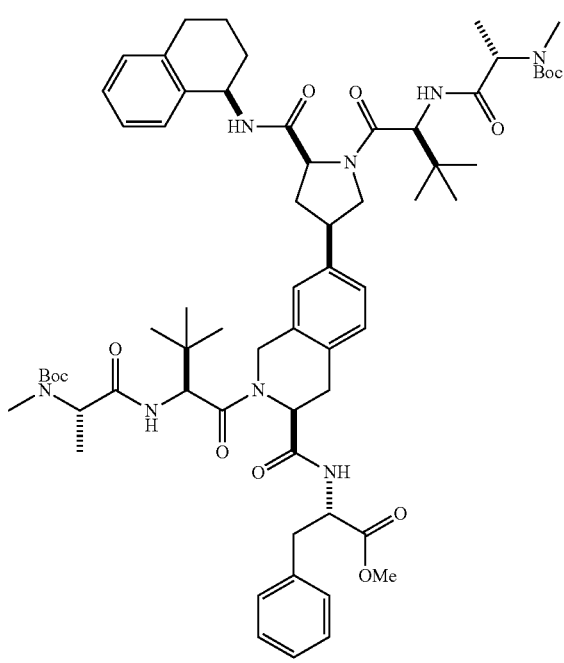

A) (S)-Methyl 2-((S)-2-((S)-2-((S)-2-((tert-butoxycarbonyl)(methyl)amino)propanamido)-3,3-dimethylbutanoyl)-7-((3R,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)-1,2,3,4-tetrahydroisoquinoline-3-carboxamido)-3-phenylpropanoate Following procedures analogous to those described for the preparation of Example 33, (S)-2-(tert-butoxycarbonyl)-7-((3R,5S)-1-(tert-butoxycarbonyl)-5-(((R)-1,2,3,4-tetrahydronaphthalen-1-yl)carbamoyl)pyrrolidin-3-yl)-1,2,3,4-tetrahydroisoquinoline-3-carboxylic acid (Compound F of Example 33, 240 mg, 0.39 mmol) and (S)-methyl 2-amino-3-phenylpropanoate, HCl (Aldrich, 109 mg, 0.50 mmol) were converted to the title compound (310 mg, 67% over 5 steps). MS (ESI$^+$) m/z 1177.9 (M+H)$^+$.

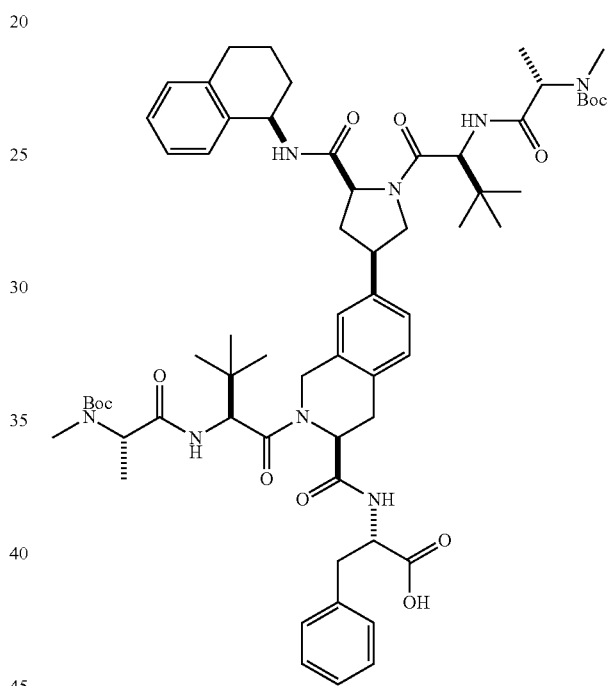

B) (S)-2-((S)-2-((S)-2-((S)-2-((tert-Butoxycarbonyl)(methyl)amino)propanamido)-3,3-dimethylbutanoyl)-7-((3R,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)-1,2,3,4-tetrahydroisoquinoline-3-carboxamido)-3-phenylpropanoic acid Following a procedure analogous to that for the synthesis of Compound K of Example 1, (S)-methyl 2-((S)-2-((S)-2-((S)-2-((tert-butoxycarbonyl)(methyl)amino)propanamido)-3,3-dimethylbutanoyl)-7-((3R,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)-1,2,3,4-tetrahydroisoquinoline-3-carboxamido)-3-phenylpropanoate (290 mg, 0.25 mmol) was converted to the title compound (172 mg, 60%). MS (ESI$^+$) m/z 1163.9 (M+H)$^+$.

139

C) (S)-2-((S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-1,2,3,4-tetrahydroisoquinoline-3-carboxamido)-3-phenylpropanoic acid Following a procedure analogous to that for the synthesis of Example 32, (S)-2-((S)-2-((S)-2-((tert-butoxycarbonyl)(methyl)amino)propanamido)-3,3-dimethylbutanoyl)-7-((3R,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-11-yl)carbamoyl)pyrrolidin-3-yl)-1,2,3,4-tetrahydroisoquinoline-3-carboxamido)-3-phenylpropanoic acid (20 mg, 0.017 mmol) was converted to the title compound (8 mg, 49%). MS (ESI$^+$) m/z 964.6 (M+H)$^+$.

Example 42

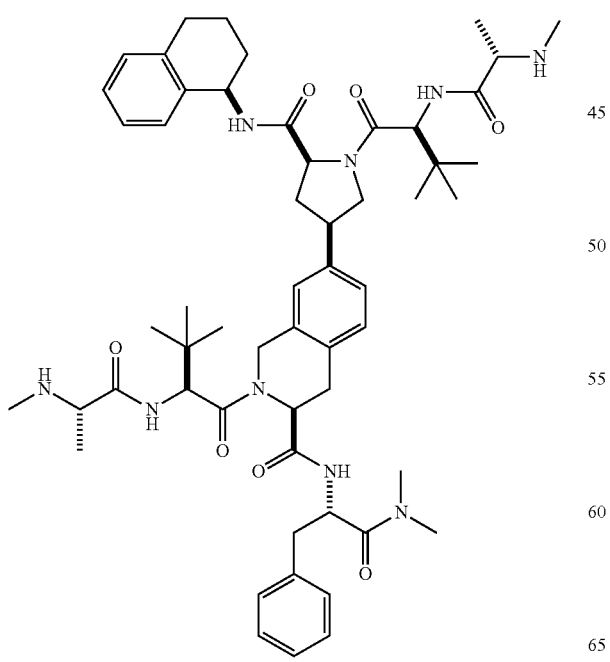

140

(S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N—((S)-1-(dimethylamino)-1-oxo-3-phenylpropan-2-yl)-1,2,3,4-tetrahydroisoquinoline-3-carboxamide

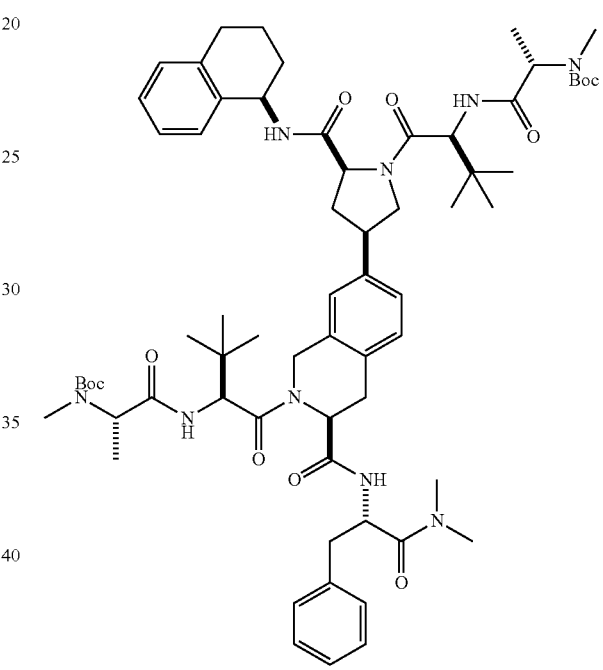

A) Boc-Precursor I

Following a procedure analogous to that for the synthesis of Compound D of Example 1, (S)-2-((S)-2-((S)-2-((tert-butoxycarbonyl)(methyl)amino)propanamido)-3,3-dimethylbutanoyl)-7-((3R,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)-1,2,3,4-tetrahydroisoquinoline-3-carboxamido)-3-phenylpropanoic acid (Compound B of Example 41, 25 mg, 0.021 mmol) and dimethylamine (1.5 mg, 0.032 mmol) were converted to the title compound (20 mg, 78%). MS (ESI⁺) m/z 1191.1 (M+H)⁺.

B) S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N—((S)-1-(dimethylamino)-1-oxo-3-phenylpropan-2-yl)-1,2,3,4-tetrahydroisoquinoline-3-carboxamide Following a procedure analogous to that for the synthesis of Example 32, Boc-Precursor I (20 mg, 0.017 mmol) was converted to the title compound (5 mg, 32%). MS (ESI⁺) m/z 990.6 (M+H)⁺.

Example 43

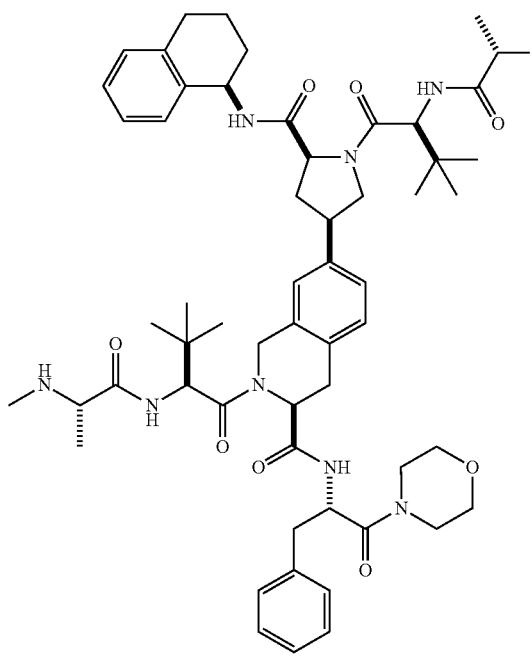

(S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N—((S)-1-morpholino-1-oxo-3-phenylpropan-2-yl)-1,2,3,4-tetrahydroisoquinoline-3-carboxamide Following procedures analogous to those described for the preparation of Example 42, (S)-2-((S)-2-((S)-2-((S)-2-((tert-butoxycarbonyl)(methyl)amino)propanamido)-3,3-dimethylbutanoyl)-7-((3R,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)-1,2,3,4-tetrahydroisoquinoline-3-carboxamido)-3-phenylpropanoic acid (Compound B of Example 41, 25 mg, 0.021 mmol) and morpholine (Aldrich, 3 mg, 0.032 mmol) were converted to the title compound (8 mg, 37% over 2 steps). MS (ESI⁺) m/z 1032.7 (M+H)⁺.

Example 44

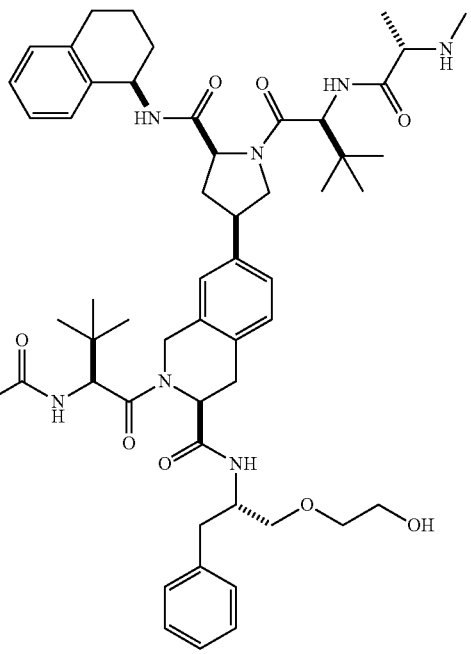

(S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N—((S)-1-(2-hydroxyethoxy)-3-phenylpropan-2-yl)-1,2,3,4-tetrahydroisoquinoline-3-carboxamide

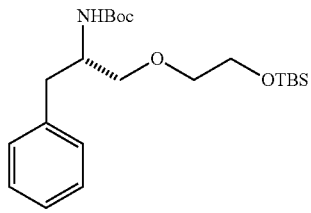 [SMILES: CC(C)(C)OC(=O)N[C@H](COCCO[Si](C)(C)C(C)(C)C)Cc1ccccc1]

A) (S)-tert-Butyl (1-(2-((tert-butyldimethylsilyl)oxy) ethoxy)-3-phenylpropan-2-yl)carbamate To a 0° C. solution of (S)-tert-butyl (1-hydroxy-3-phenylpropan-2-yl)carbamate (Alfa Aesar, 500 mg, 1.99 mmol) in DMF (13.0 mL) was added NaH (60% in mineral oil, 119 mg, 2.98 mmol). The resulting reaction mixture was stirred at 0° C. for 15 min and then (2-bromoethoxy)(tert-butyl)dimethylsilane (512 μL, 2.39 mmol) was added. The reaction mixture was stirred at 0° C. for 2 h and then at room temperature for 3 h. The mixture was poured into a separatory funnel containing EtOAc and sat. aq. NH₄Cl. The aqueous layer was extracted with EtOAc (3×), and the combined organics were washed with sat. NaCl, dried over Na₂SO₄, filtered and concentrated in vacuo. The crude oil was purified using flash chromatography (40 g column, gradient from 0% to 40% EtOAc/hexanes over 14 min) to give the title compound (124 mg, 15%) as a colorless oil. MS (ESI⁺) m/z 310.1 (M+H–Boc)⁺.

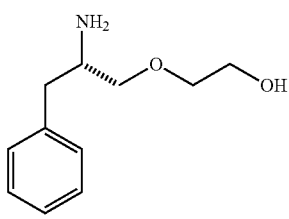 [SMILES: N[C@H](COCCO)Cc1ccccc1]

B) (S)-2-(2-Amino-3-phenylpropoxy)ethanol, HCl

To a solution of (S)-tert-butyl (1-(2-((tert-butyldimethylsilyl)oxy)ethoxy)-3-phenylpropan-2-yl)carbamate (32 mg, 0.077 mmol) in CH$_2$Cl$_2$ (1.0 mL) was added HCl (4N in dioxane, 0.58 mL, 2.31 mmol). The resulting reaction mixture was stirred at room temperature for 1.5 h and then concentrated in vacuo to give the title compound (18 mg, 100%) as an off-white solid. MS (ESI$^+$) m/z 196.1 (M+H)$^+$.

C) (S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N—((S)-1-(2-hydroxyethoxy)-3-phenylpropan-2-yl)-1,2,3,4-tetrahydroisoquinoline-3-carboxamide Following procedures analogous to those described for the preparation of Example 33, (S)-2-(tert-butoxycarbonyl)-7-((3R,5S)-1-(tert-butoxycarbonyl)-5-(((R)-1,2,3,4-tetrahydronaphthalen-1-yl)carbamoyl)pyrrolidin-3-yl)-1,2,3,4-tetrahydroisoquinoline-3-carboxylic acid (Compound F of Example 33, 100 mg, 0.16 mmol) and (S)-2-(2-amino-3-phenylpropoxy)ethanol, HCl (39 mg, 0.17 mmol) were converted to the title compound (27 mg, 17% over 6 steps). MS (ESI$^+$) m/z 994.0 (M+H)$^+$.

Example 45

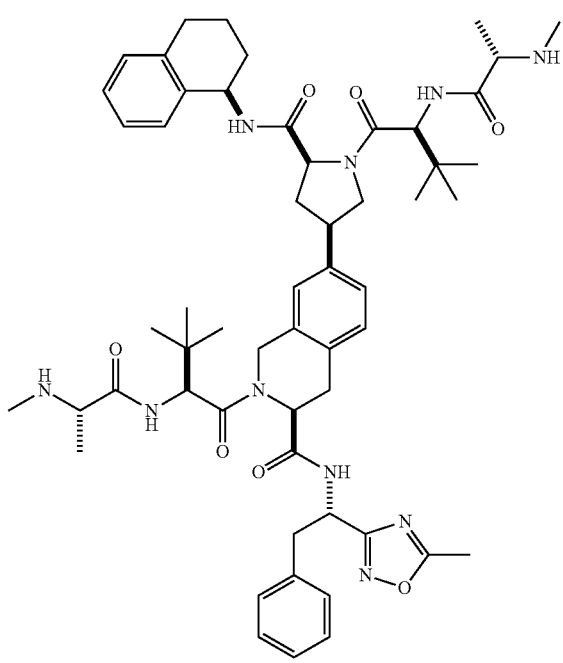

(S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N—((S)-1-(5-methyl-1,2,4-oxadiazol-3-yl)-2-phenylethyl)-1,2,3,4-tetrahydroisoquinoline-3-carboxamide

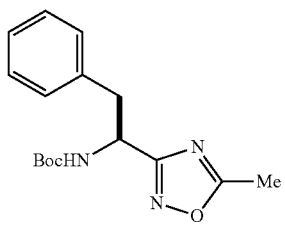

A) (S)-tert-Butyl (1-(5-methyl-1,2,4-oxadiazol-3-yl)-2-phenylethyl)carbamate To a 1 dram vial containing (S)-tert-butyl (1-cyano-2-phenylethyl)carbamate (Arch, 400 mg, 1.62 mmol) in EtOH (3.2 mL) was added hydroxylamine HCl (135 mg, 1.95 mmol). The reaction mixture was stirred at 50° C. overnight and then concentrated in vacuo to give a white solid.

To half of the crude white solid from above (~280 mg) in trimethylorthoacetate (5.0 mL) was added AcOH (0.34 mL, 5.95 mmol). The resulting reaction mixture was stirred at 65° C. for 2 h, then at 72° C. for 18 h and then at room temperature for 72 h. The mixture was concentrated in vacuo and purified directly using flash chromatography (gradient from 0% to 30% EtOAc/hexanes) to give the title compound (120 mg, 40% over 2 steps) as a pale yellow solid. $^1$H NMR (CDCl$_3$) δ 7.30-7.19 (m, 3H), 7.11 (d, J=7.0 Hz, 2H), 5.20 (br s, 1H), 5.04 (br s, 1H), 3.30-3.07 (m, 2H), 2.59 (s, 3H), 1.47-1.31 (m, 9H); MS (ESI$^+$) m/z 204.2 (M+H−Boc)$^+$.

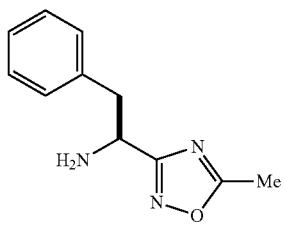

B) (S)-1-(5-Methyl-1,2,4-oxadiazol-3-yl)-2-phenylethanamine, TFA

A solution of TFA (20% in CH$_2$Cl$_2$, 3.0 mL, 7.91 mmol) was added to (S)-tert-butyl (1-(5-methyl-1,2,4-oxadiazol-3-yl)-2-phenylethyl)carbamate (120 mg, 0.40 mmol). The resulting reaction mixture was stirred at room temperature for 1 h, then concentrated in vacuo and azeotroped from PhMe (2×) to give the title compound (124 mg, 99%) as a tan solid. MS (ESI$^+$) m/z 204.0 (M+H)$^+$.

145

C) (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N—((S)-1-(5-methyl-1,2,4-oxadiazol-3-yl)-2-phenylethyl)-1,2,3,4-tetrahydroisoquinoline-3-carboxamide Following procedures analogous to those described for the preparation of Example 33, (S)-2-(tert-butoxycarbonyl)-7-((3R,5S)-1-(tert-butoxycarbonyl)-5-(((R)-1,2,3,4-tetrahydronaphthalen-1-yl)carbamoyl)pyrrolidin-3-yl)-1,2,3,4-tetrahydroisoquinoline-3-carboxylic acid (Compound F of Example 33, 60 mg, 0.10 mmol) and (S)-1-(5-methyl-1,2,4-oxadiazol-3-yl)-2-phenylethanamine, TFA (31 mg, 0.10 mmol) were converted to the title compound (34 mg, 33% over 6 steps). MS (ESI$^+$) m/z 1001.7 (M+H)$^+$.

Example 46

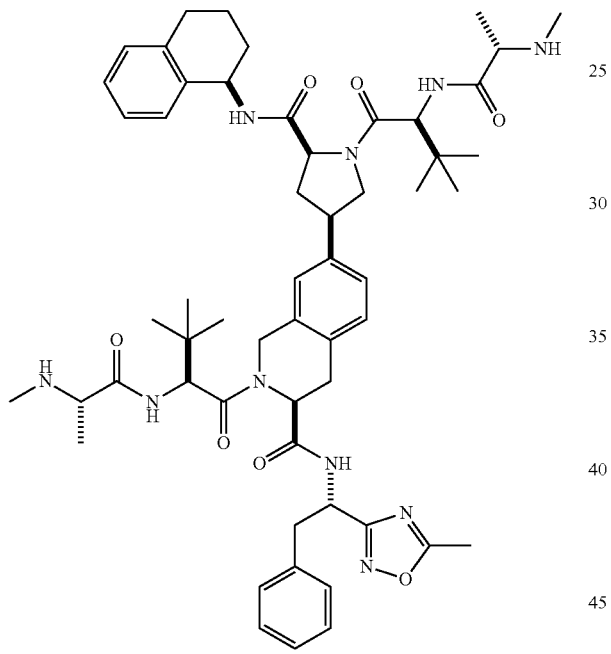

(S)-7-((3R,5S)-5-(((S)-1-Amino-1-oxo-3-phenylpropan-2-yl)carbamoyl)-1-((S)-3,3-dimethyl-2-((S)-2-(methylamino)propanamido)butanoyl)pyrrolidin-3-yl)-2-((S)-3,3-dimethyl-2-((S)-2-(methylamino)propanamido)butanoyl)-N—((R)-1,2,3,4-tetrahydronaphthalen-1-yl)-1,2,3,4-tetrahydroisoquinoline-3-carboxamide

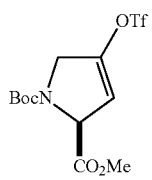 [SMILES: COC(=O)[C@@H]1C=C(OS(=O)(=O)C(F)(F)F)CN1C(=O)OC(C)(C)C]

146

A) (S)-1-tert-Butyl 2-methyl 4-(((trifluoromethyl)sulfonyl)oxy)-1H-pyrrole-1,2(2H,5H)-dicarboxylate Following a procedure analogous to that for the synthesis of Compound B of Example 22, (S)-1-tert-butyl 2-methyl 4-oxopyrrolidine-1,2-dicarboxylate (Aldrich, 700 mg, 2.88 mmol) was converted to the title compound (820 mg, 76%). MS (ESI$^+$) m/z 275.9 (M+H−Boc)$^+$.

B) (2S,4R)-Methyl 1-((S)-2-((S)-2-((tert-butoxycarbonyl)(methyl)amino)propanamido)-3,3-dimethylbutanoyl)-4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)pyrrolidine-2-carboxylate Following procedures analogous to those described for the preparation of Example 22, (S)-1-tert-butyl 2-methyl 4-(((trifluoromethyl)sulfonyl)oxy)-1H-pyrrole-1,2(2H,5H)-dicarboxylate (200 mg, 0.53 mmol) and (S)-tert-butyl 3-(((R)-1,2,3,4-tetrahydronaphthalen-1-yl)carbamoyl)-7-(4,4,5,5-tetramethyl-1,3,2-dioxaborolan-2-yl)-3,4-dihydroisoquinoline-2(1H)-carboxylate (Compound C of Example 22, 284 mg, 0.53 mmol) were converted to the title compound. MS (ESI$^+$) m/z 1030.8 (M+H)$^+$.

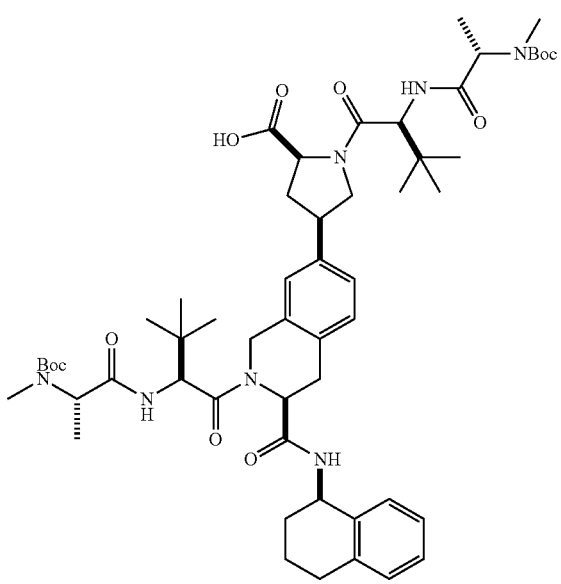

C) (2S,4R)-1-((S)-2-((S)-2-((tert-Butoxycarbonyl)(methyl)amino)propanamido)-3,3-dimethylbutanoyl)-4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)pyrrolidine-2-carboxylic acid Following a procedure analogous to that for the synthesis of Compound K of Example 1, (2S,4R)-methyl 1-((S)-2-((S)-2-((tert-butoxycarbonyl)(methyl)amino)propanamido)-3,3-dimethylbutanoyl)-4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)pyrrolidine-2-carboxylate (301 mg, 0.29 mmol) was converted to the title compound (282 mg, 95%). MS (ESI+) m/z 1016.7 (M+H)+.

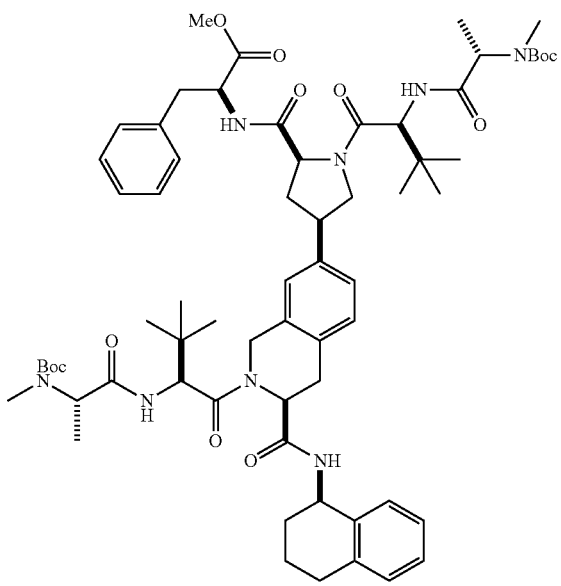

A) (S)-Methyl 2-((2S,4R)-1-((S)-2-((S)-2-((tert-butoxycarbonyl)(methyl)amino)propanamido)-3,3-dimethylbutanoyl)-4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)pyrrolidine-2-carboxamido)-3-phenylpropanoate Following a procedure analogous to that for the synthesis of Compound D of Example 1, ((2S,4R)-1-((S)-2-((S)-2-((tert-butoxycarbonyl)(methyl)amino)propanamido)-3,3-dimethylbutanoyl)-4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)pyrrolidine-2-carboxylic acid (282 mg, 0.28 mmol) and (S)-methyl 2-amino-3-phenylpropanoate, HCl (90 mg, 0.42 mmol) were converted to the title compound (310 mg, 95%). MS (ESI+) m/z 1177.8 (M+H)+.

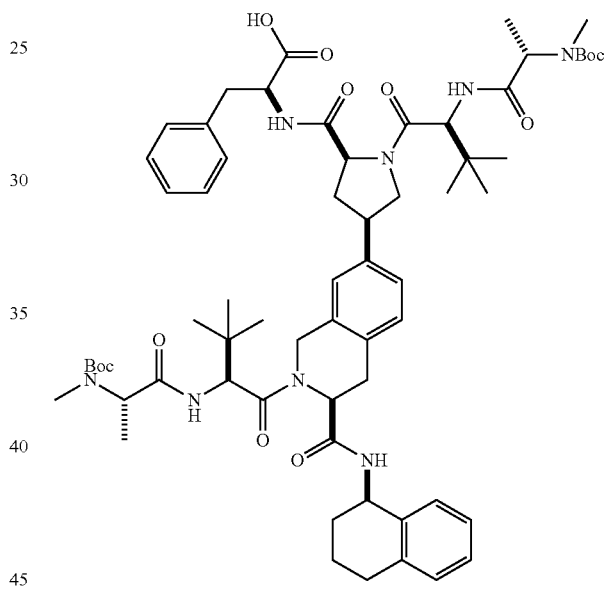

B) (S)-2-((2S,4R)-1-((S)-2-((S)-2-((tert-Butoxycarbonyl)(methyl)amino)propanamido)-3,3-dimethylbutanoyl)-4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)pyrrolidine-2-carboxamido)-3-phenylpropanoic acid Following a procedure analogous to that for the synthesis of Compound K of Example 1, (S)-methyl 2-((2S,4R)-1-((S)-2-((S)-2-((tert-butoxycarbonyl)(methyl)amino)propanamido)-3,3-dimethylbutanoyl)-4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)pyrrolidine-2-carboxamido)-3-phenylpropanoate (310 mg, 0.26 mmol) was converted to the title compound (291 mg, 95%). MS (ESI+) m/z 1016.7 (M+H)+.

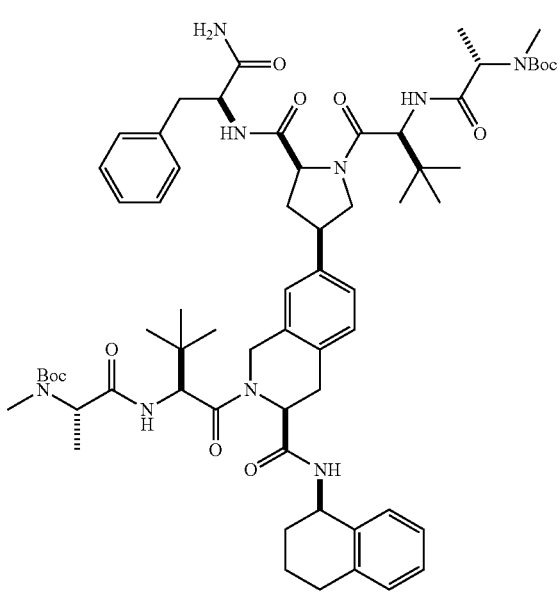

C) Boc-Precursor I

Following a procedure analogous to that for the synthesis of Compound D of Example 1, (S)-2-((2S,4R)-1-((S)-2-((S)-2-((tert-butoxycarbonyl)(methyl)amino)propanamido)-3,3-dimethylbutanoyl)-4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl) pyrrolidine-2-carboxamido)-3-phenylpropanoic acid (50 mg, 0.043 mmol) and ammonia (210 µL, 0.086 mmol, 0.4N in THF) were converted to the title compound (33 mg, 66%). MS (ESI+) m/z 1163.7 (M+H)+.

D) (S)-7-((3R,5S)-5-(((S)-1-Amino-1-oxo-3-phenyl-propan-2-yl)carbamoyl)-1-((S)-3,3-dimethyl-2-((S)-2-(methylamino)propanamido)butanoyl)pyrrolidin-3-yl)-2-((S)-3,3-dimethyl-2-((S)-2-(methylamino) propanamido)butanoyl)-N—((R)-1,2,3,4-tetrahydronaphthalen-1-yl)-1,2,3,4-tetrahydroisoquinoline-3-carboxamide To a solution of Boc-Precursor I (33 mg, 0.028 mmol) in CH2Cl2 (1.5 mL) was added TFA (0.5 mL). The resulting reaction mixture was stirred at room temperature for 1 h and then concentrated in vacuo. The crude oil was purified using preparative HPLC to give the title compound (15 mg, 55%) as a white solid after lyophilization. MS (ESI+) m/z 962.6 (M+H)+.

Examples 47 to 73

The following Examples were prepared according to the procedures described for the synthesis of Example 46.

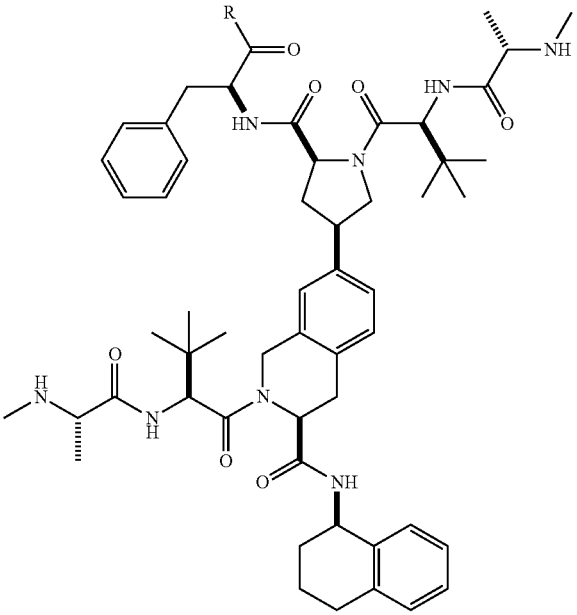

| Ex. No. | R | Name | LCMS (M + H) |
|---|---|---|---|
| 47 |  | (S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((S)-1-morpholino-1-oxo-3-phenylpropan-2-yl)carbamoyl) pyrrolidin-3-yl)-N-((R)-1,2,3,4-tetrahydronaphthalen-1-yl)-1,2,3,4-tetrahydroisoquinoline-3-carboxamide | 1032.7 |

-continued

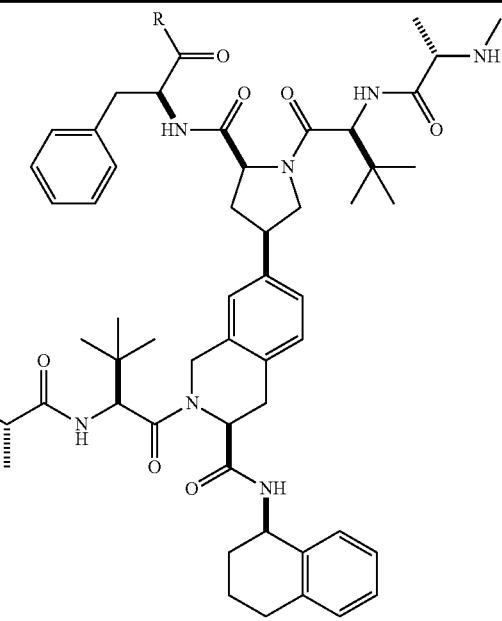

| Ex. No. | R | Name | LCMS (M + H) |
|---|---|---|---|
| 48 | phenyl-SO2-NH- | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((S)-1-oxo-3-phenyl-1-(phenylsulfonamido)propan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1102.6 |
| 49 | naphthalen-2-yl-SO2-NH- | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((S)-1-(naphthalene-2-sulfonamido)-1-oxo-3-phenylpropan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1152.7 |
| 50 | cyclopropyl-SO2-NH- | (S)-7-((3R,5S)-5-(((S)-1-(Cyclopropanesulfonamido)-1-oxo-3-phenylpropan-2-yl)carbamoyl)-1-((S)-3,3-dimethyl-2-((S)-2-(methylamino)propanamido)butanoyl) pyrrolidin-3-yl)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide | 1066.6 |
| 51 | ethyl-NH- | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((S)-1-(ethylamino)-1-oxo-3-phenylpropan-2-yl)carbamoyl) pyrrolidin-3-yl)-N-((R)-1,2,3,4-tetrahydronaphthalen-1-yl)-1,2,3,4-tetrahydroisoquinoline-3-carboxamide | 990.5 |
| 52 | 1,3,4-thiadiazol-2-yl-NH- | (S)-7-((3R,5S)-5-(((S)-1-((1,3,4-Thiadiazol-2-yl)amino)-1-oxo-3-phenylpropan-2-yl)carbamoyl)-1-((S)-3,3-dimethyl-2-((S)-2-(methylamino)propanamido)butanoyl) pyrrolidin-3-yl)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide | 1046.3 |

-continued

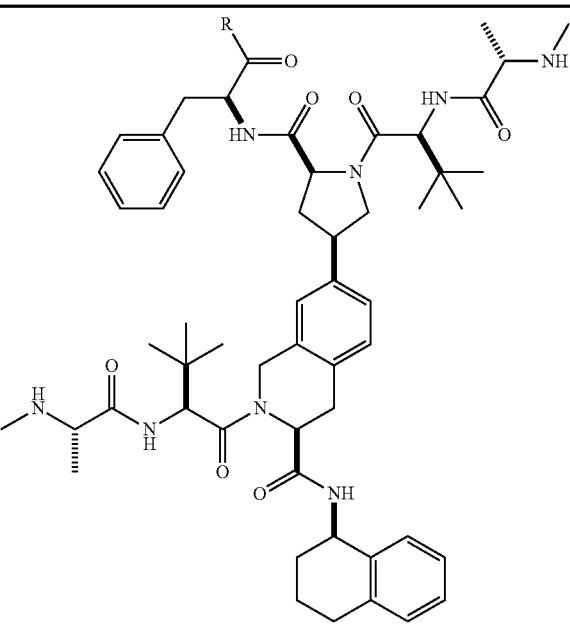

| Ex. No. | R | Name | LCMS (M + H) |
|---|---|---|---|
| 53 | isopentyl(methyl)amino group | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((S)-1-(isopentyl(methyl)amino)-1-oxo-3-phenylpropan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1046.5 |
| 54 | methyl(2-(pyridin-2-yl)ethyl)amino group | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((S)-1-(methyl(2-(pyridin-2-yl)ethyl)amino)-1-oxo-3-phenylpropan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1081.5 |
| 55 | (2-methoxyethyl)(methyl)amino group | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((S)-1-((2-methoxyethyl)(methyl)amino)-1-oxo-3-phenylpropan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1034.5 |
| 56 | isopropylamino group | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((S)-1-(isopropylamino)-1-oxo-3-phenylpropan-2-yl)carbamoyl) pyrrolidin-3-yl)-N-((R)-1,2,3,4-tetrahydronaphthalen-1-yl)-1,2,3,4-tetrahydroisoquinoline-3-carboxamide | 1004.5 |
| 57 | (4-(oxazol-5-yl)phenyl)amino group | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((S)-1-((4-(oxazol-5-yl)phenyl)amino)-1-oxo-3-phenylpropan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1105.5 |
| 58 | (3-(oxazol-5-yl)phenyl)amino group | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((S)-1-((3-(oxazol-5-yl)phenyl)amino)-1-oxo-3-phenylpropan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1105.5 |

-continued

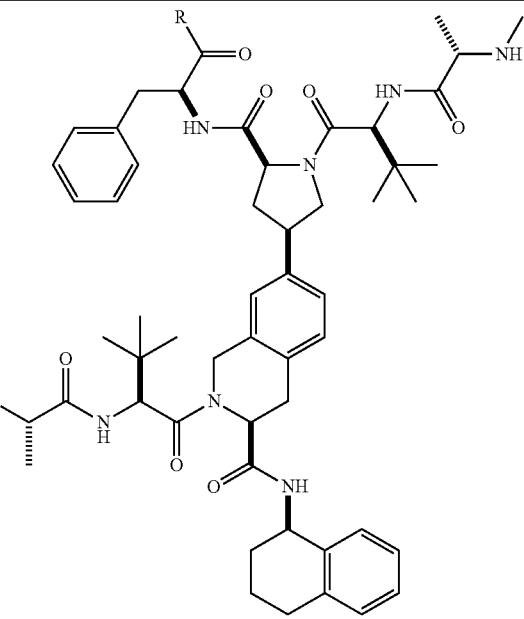

| Ex. No. | R | Name | LCMS (M + H) |
|---|---|---|---|
| 59 | NC-phenyl-NH- | (S)-7-((3R,5S)-5-(((S)-1-((3-Cyanophenyl)amino)-1-oxo-3-phenylpropan-2-yl)carbamoyl)-1-((S)-3,3-dimethyl-2-((S)-2-(methylamino)propanamido)butanoyl)pyrrolidin-3-yl)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide | 1063.4 |
| 60 | benzyl-piperidinyl | (S)-7-((3R,5S)-5-(((S)-1-(4-Benzylpiperidin-1-yl)-1-oxo-3-phenylpropan-2-yl)carbamoyl)-1-((S)-3,3-dimethyl-2-((S)-2-(methylamino)propanamido)butanoyl)pyrrolidin-3-yl)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide | 1120.6 |
| 61 | MeO-CH2CH2-NH- | (S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((S)-1-((2-methoxyethyl)amino)-1-oxo-3-phenylpropan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1020.5 |
| 62 | Et2N- | (S)-7-((3R,5S)-5-(((S)-1-(Diethylamino)-1-oxo-3-phenylpropan-2-yl)carbamoyl)-1-((S)-3,3-dimethyl-2-((S)-2-(methylamino)propanamido)butanoyl)pyrrolidin-3-yl)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide | 1018.5 |
| 63 | (cyclopropyl)2N- | (S)-7-((3R,5S)-5-(((S)-1-(Dicyclopropylamino)-1-oxo-3-phenylpropan-2-yl)carbamoyl)-1-((S)-3,3-dimethyl-2-((S)-2-(methylamino)propanamido)butanoyl)pyrrolidin-3-yl)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide | 1042.5 |
| 64 | cyclopropyl-NH- | (S)-7-((3R,5S)-5-(((S)-1-(Cyclopropylamino)-1-oxo-3-phenylpropan-2-yl)carbamoyl)-1-((S)-3,3-dimethyl-2-((S)-2-(methylamino)propanamido)butanoyl)pyrrolidin-3-yl)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide | 1002.5 |

-continued

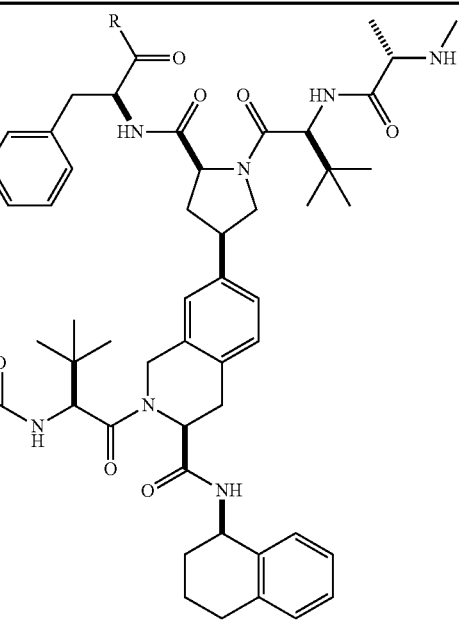

| Ex. No. | R | Name | LCMS (M + H) |
|---|---|---|---|
| 65 | (triazolyl-phenyl-NH-) | (S)-7-((3R,5S)-5-(((S)-1-((4-(1H-1,2,4-Triazol-1-yl)phenyl)amino)-1-oxo-3-phenylpropan-2-yl)carbamoyl)-1-((S)-3,3-dimethyl-2-((S)-2-(methylamino)propanamido)butanoyl)pyrrolidin-3-yl)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide | 1105.4 |
| 66 | (phenethyl-NH-) | (S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((S)-1-oxo-1-(phenethylamino)-3-phenylpropan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1066.5 |
| 67 | (thiazol-2-ylmethyl-NH-) | (S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((S)-1-oxo-3-phenyl-1-((thiazol-2-ylmethyl)amino)propan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1059.4 |
| 68 | (phenyl-NH-) | (S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((S)-1-oxo-3-phenyl-1-(phenylamino)propan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1038.5 |
| 69 | (isopentyl-NH-) | (S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((S)-1-(isopentylamino)-1-oxo-3-phenylpropan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1032.5 |
| 70 | MeO-(4-methoxybenzyl-NH-) | (S)-2-((S)-3,3-Dimethyl-2-((S)-2-(methylamino)propanamido)butanoyl)-7-((3S,5S)-1-((S)-3,3-dimethyl-2-((S)-2-(methylamino)propanamido)butanoyl)-5-(((S)-1-((4-methoxybenzyl)amino)-1-oxo-3-phenylpropan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1082.4 |

-continued

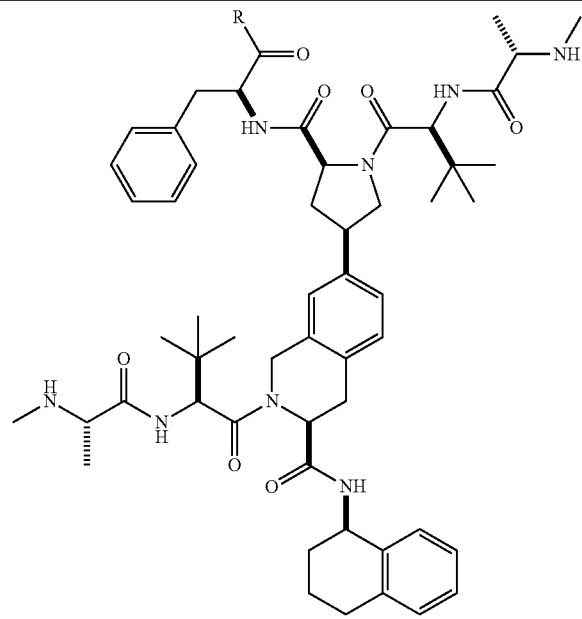

| Ex. No. | R | Name | LCMS (M + H) |
|---|---|---|---|
| 71 | 4-fluorophenyl-NH- | (S)-2-((S)-3,3-Dimethyl-2-((S)-2-(methylamino)propanamido)butanoyl)-7-((3S,5S)-1-((S)-3,3-dimethyl-2-((S)-2-(methylamino)propanamido)butanoyl)-5-(((S)-1-((4-fluorophenyl)amino)-1-oxo-3-phenylpropan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1056.6 |
| 72 | benzyl(methyl)amino | (S)-7-((3S,5S)-5-(((S)-1-(Benzyl(methyl)amino)-1-oxo-3-phenylpropan-2-yl)carbamoyl)-1-((S)-3,3-dimethyl-2-((S)-2-(methylamino)propanamido)butanoyl)pyrrolidin-3-yl)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide | 1066.6 |
| 73 | piperidin-1-yl | (S)-2-((S)-3,3-Dimethyl-2-((S)-2-(methylamino)propanamido)butanoyl)-7-((3S,5S)-1-((S)-3,3-dimethyl-2-((S)-2-(methylamino)propanamido)butanoyl)-5-(((S)-1-oxo-3-phenyl-1-(piperidin-1-yl)propan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 1030.7 |

Examples 74 to 77

The following Examples were prepared according to the procedures described for the synthesis of Example 46.

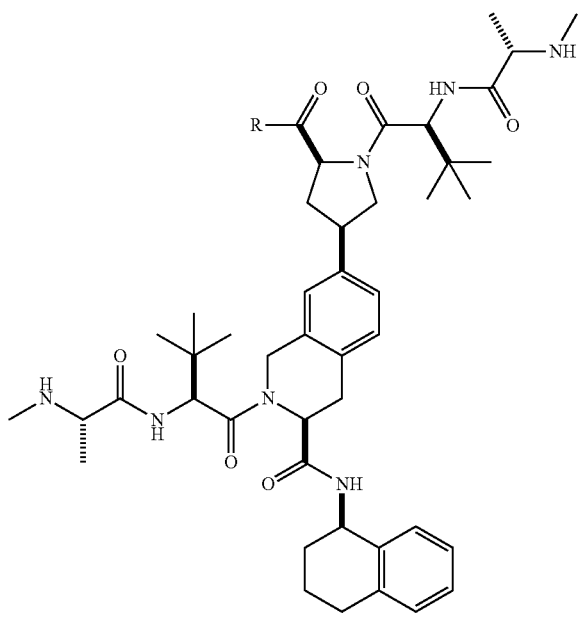

| Ex. No. | R | Name | LCMS (M + H) |
|---|---|---|---|
| 74 | HO— CH2—CH(HN—)—CH2—C6H5 | (S)-2-((S)-3,3-Dimethyl-2-((S)-2-(methylamino) propanamido)butanoyl)-7-((3S,5S)-1-((S)-3,3-dimethyl-2-((S)-2-(methylamino)propanamido)butanoyl)-5-(((S)-1-hydroxy-3-phenylpropan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 949.6 |
| 75 | MeO—CH2—CH(HN—)—CH2—C6H5 | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido )butanoyl)-5-(((S)-1-methoxy-3-phenylpropan-2-yl)carbamoyl)pyrrolidin-3-yl)-N-((R)-1,2,3,4-tetrahydronaphthalen-1-yl)-1,2,3,4-tetrahydroisoquinoline-3-carboxamide | 963.5 |
| 76 | MeO—C(=O)—CH(HN—)—CH2—C6H5 | (S)-Methyl 2-((2S,4R)-1-((S)-3,3-dimethyl-2-((S)-2-(methylamino)propanamido)butanoyl)-4-((S)-2-((S)-3,3-dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)pyrrolidine-2-carboxamido)-3-phenylpropanoate | 977.7 |
| 77 | HO—C(=O)—CH(HN—)—CH2—C6H5 | (S)-2-((2S,4R)-1-((S)-3,3-Dimethyl-2-((S)-2-(methylamino) propanamido)butanoyl)-4-((S)-2-((S)-3,3-dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)pyrrolidine-2-carboxamido)-3-phenylpropanoic acid | 963.7 |

Example 78

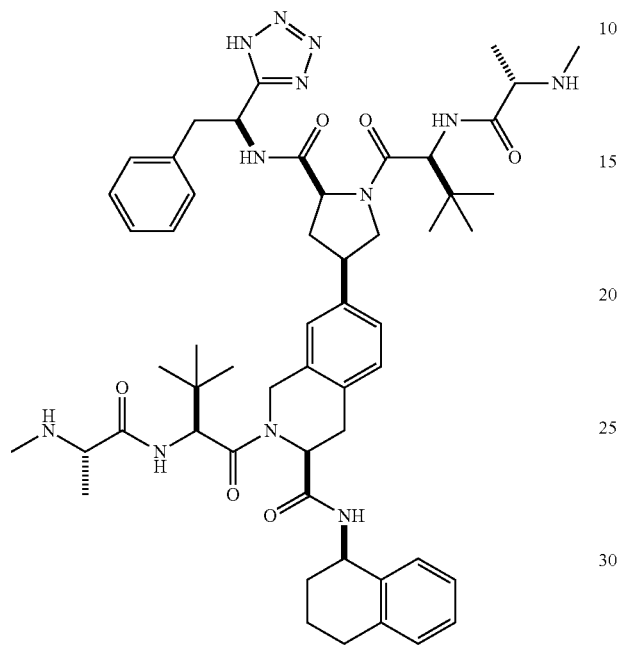

(S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((S)-2-phenyl-1-(1H-tetrazol-5-yl)ethyl)carbamoyl)pyrrolidin-3-yl)-N—((R)-1,2,3,4-tetrahydronaphthalen-1-yl)-1,2,3,4-tetrahydroisoquinoline-3-carboxamide

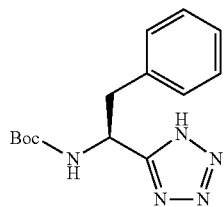 [SMILES: CC(C)(C)OC(=O)N[C@@H](Cc1ccccc1)c1nnn[nH]1]

A) (S)-tert-Butyl (2-phenyl-1-(1H-tetrazol-5-yl)ethyl)carbamate

To a solution of acetic acid (93 µL, 1.62 mmol) in PhMe (2.0 mL) was added Et₃N (226 µL, 1.624 mmol). (S)-tert-Butyl (1-cyano-2-phenylethyl)carbamate (100 mg, 0.41 mmol) was then added to the mixture followed by NaN₃ (106 mg, 1.62 mmol). The resulting reaction mixture was heated at 100° C. for 2 h and then filtered, rinsing with EtOAc. The filtrate was concentrated in vacuo and purified using preparative HPLC to give the title compound (100 mg, 85%) as a white solid after lyophilization. ¹H NMR (CDCl₃) δ 7.37-7.20 (m, 3H), 7.12 (d, J=6.6 Hz, 2H), 5.56 (br s, 1H), 5.30 (d, J=6.2 Hz, 1H), 3.35 (d, J=6.4 Hz, 2H), 1.51-1.17 (m, 9H); MS (ESI⁺) m/z 290.2 (M+H)⁺.

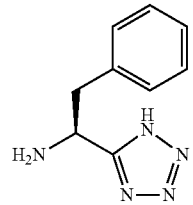 [SMILES: N[C@@H](Cc1ccccc1)c1nnn[nH]1]

B) (S)-2-Phenyl-1-(1H-tetrazol-5-yl)ethanamine, TFA

To a solution of (S)-tert-butyl (2-phenyl-1-(1H-tetrazol-5-yl)ethyl)carbamate (50 mg, 0.17 mmol) in CH₂Cl₂ (1.5 mL) was added TFA (0.5 mL). The resulting reaction mixture was stirred at room temperature for 1 h, then concentrated in vacuo and used without purification in the subsequent step. MS (ESI⁺) m/z 190.1 (M+H)⁺.

C) S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((S)-2-phenyl-1-(1H-tetrazol-5-yl)ethyl)carbamoyl)pyrrolidin-3-yl)-N—((R)-1,2,3,4-tetrahydronaphthalen-1-yl)-1,2,3,4-tetrahydroisoquinoline-3-carboxamide Following procedures analogous to those for the preparation of Compounds F and G of Example 46, (S)-2-((2S,4R)-1-((S)-2-((S)-2-((tert-butoxycarbonyl)(methyl)amino)propanamido)-3,3-dimethylbutanoyl)-4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)pyrrolidine-2-carboxamido)-3-phenylpropanoic acid (Compound D of Example 46, 30 mg, 0.030 mmol) and (S)-2-phenyl-1-(1H-tetrazol-5-yl)ethanamine, TFA (17 mg, 0.059 mmol) were converted to the title compound (10 mg, 33% over 2 steps). MS (ESI⁺) m/z 987.8 (M+H)⁺.

Example 79

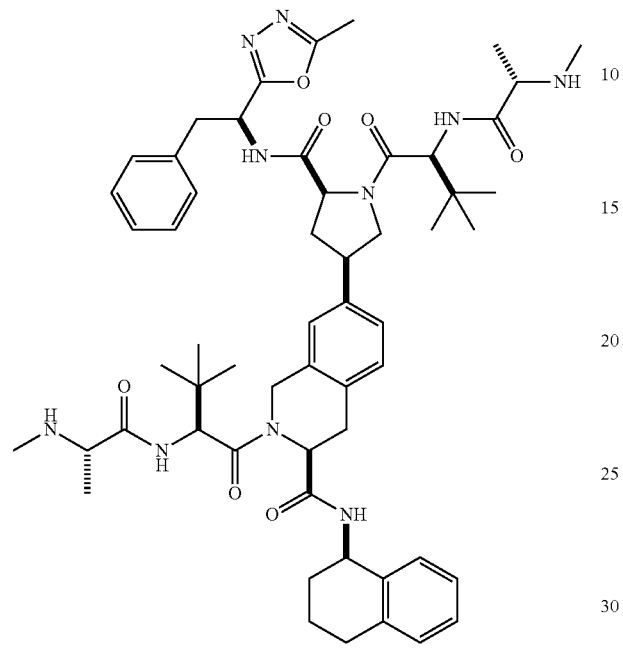

(S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((S)-1-(5-methyl-1,3,4-oxadiazol-2-yl)-2-phenylethyl)carbamoyl)pyrrolidin-3-yl)-N—((R)-1,2,3,4-tetrahydronaphthalen-1-yl)-1,2,3,4-tetrahydroisoquinoline-3-carboxamide

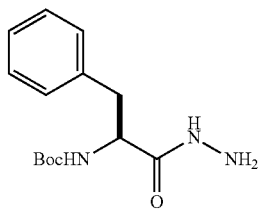 [SMILES: CC(C)(C)OC(=O)N[C@@H](Cc1ccccc1)C(=O)NN]

A) (S)-tert-Butyl (1-hydrazinyl-1-oxo-3-phenylpropan-2-yl)carbamate

To (S)-methyl 2-((tert-butoxycarbonyl)amino)-3-phenylpropanoate (Aldrich, 300 mg, 1.07 mmol) in MeOH (5.4 mL) was added hydrazine hydrate (170 µL, 3.44 mmol). The resulting solution was stirred at room temperature overnight and then concentrated in vacuo. The residue was triturated with hexanes (2×) and then from a minimal amount of 2:3 hexanes/MeOH (2×) to give the title compound (195 mg, 65%) as a white solid. ¹H NMR (CDCl₃) δ 7.41-7.25 (m, 3H), 7.20 (d, J=6.8 Hz, 2H), 4.39-4.21 (m, 1H), 3.07 (d, J=7.0 Hz, 2H), 1.42 (s, 9H); MS (ESI⁺) m/z 280.3 (M+H)⁺.

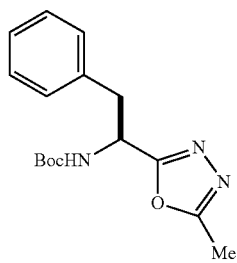 [SMILES: Cc1nnc([C@H](Cc2ccccc2)NC(=O)OC(C)(C)C)o1]

B) (S)-tert-Butyl (1-(5-methyl-1,3,4-oxadiazol-2-yl)-2-phenylethyl)carbamate

To (S)-tert-butyl (1-hydrazinyl-1-oxo-3-phenylpropan-2-yl)carbamate (120 mg, 0.43 mmol) in PhMe (4.3 mL) was added triethyl orthoacetate (396 µL, 2.15 mmol) and AcOH (443 µL, 7.73 mmol). The resulting solution was stirred at 80° C. for 2 h, then concentrated in vacuo and used in the subsequent step without purification. MS (ESI⁺) m/z 304.3 (M+H)⁺.

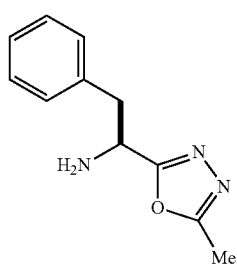 [SMILES: Cc1nnc([C@@H](N)Cc2ccccc2)o1]

C) (S)-1-(5-Methyl-1,3,4-oxadiazol-2-yl)-2-phenylethanamine

Following a procedure analogous to that for the synthesis of Compound B of Example 78, (S)-tert-butyl (1-(5-methyl-1,3,4-oxadiazol-2-yl)-2-phenylethyl)carbamate (130 mg, 0.43 mmol) was converted to the title compound (45 mg, 52% over 2 steps) after preparative HPLC. ¹H NMR (CDCl₃) δ 7.38-7.14 (m, 1H), 4.43 (dd, J=8.4, 5.5 Hz, 1H), 3.27 (dd, J=13.6, 5.3 Hz, 1H), 3.04 (dd, J=13.6, 8.4 Hz, 1H), 2.53 (s, 3H); MS (ESI⁺) m/z 204.2 (M+H)⁺.

D) (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((S)-1-(5-methyl-1,3,4-oxadiazol-2-yl)-2-phenylethyl)carbamoyl)pyrrolidin-3-yl)-N—((R)-1,2,3,4-tetrahydronaphthalen-1-yl)-1,2,3,4-tetrahydroisoquinoline-3-carboxamide Following procedures analogous to those for the preparation of Compounds F and G of Example 46, (S)-2-((2S,4R)-1-((S)-2-((S)-2-((tert-butoxycarbonyl)(methyl)amino)propanamido)-3,3-dimethylbutanoyl)-4-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl) pyrrolidine-2-carboxamido)-3-phenylpropanoic acid (Compound D of Example 46, 50 mg, 0.049 mmol) and (S)-1-(5-methyl-1,3,4-oxadiazol-2-yl)-2-phenylethanamine (10 mg, 0.049 mmol) were converted to the title compound (26 mg, 53% over 2 steps). MS (ESI+) m/z 1001.8 (M+H)+.

Example 80

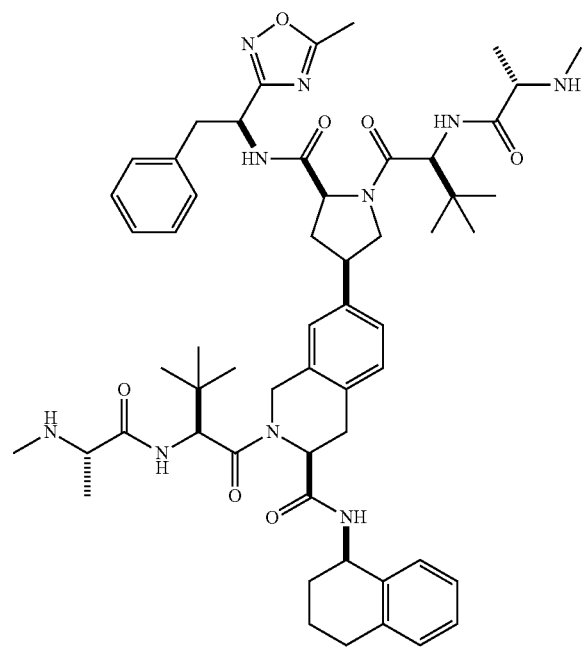

(S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((S)-1-(5-methyl-1,2,4-oxadiazol-3-yl)-2-phenylethyl)carbamoyl)pyrrolidin-3-yl)-N—((R)-1,2,3,4-tetrahydronaphthalen-1-yl)-1,2,3,4-tetrahydroisoquinoline-3-carboxamide Following procedures analogous to those for the preparation of Compounds F and G of Example 46, (S)-2-((2S,4R)-1-((S)-2-((S)-2-((tert-butoxycarbonyl)(methyl)amino)propanamido)-3,3-dimethylbutanoyl)-4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)pyrrolidine-2-carboxamido)-3-phenylpropanoic acid (Compound D of Example 46, 45 mg, 0.044 mmol) and (S)-1-(5-methyl-1,2,4-oxadiazol-3-yl)-2-phenylethanamine, TFA (Compound B of Example 45, 15 mg, 0.049 mmol) were converted to the title compound (23 mg, 49% over 2 steps). MS (ESI+) m/z 1002.5 (M+H)+.

Example 81

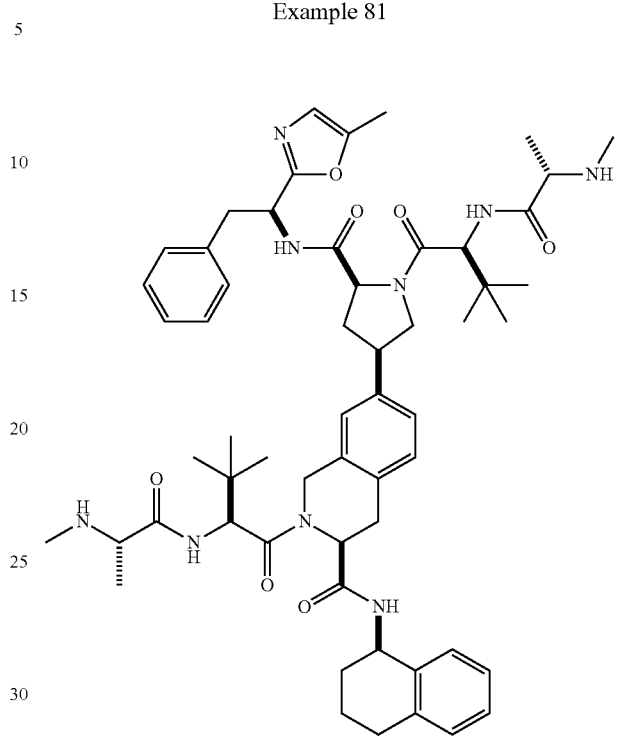

(S)-2-((S)-3,3-Dimethyl-2-((S)-2-(methylamino)propanamido)butanoyl)-7-((3R,5S)-1-((S)-3,3-dimethyl-2-((S)-2-(methylamino)propanamido)butanoyl)-5-(((S)-1-(5-methyloxazol-2-yl)-2-phenylethyl)carbamoyl)pyrrolidin-3-yl)-N—((R)-1,2,3,4-tetrahydronaphthalen-1-yl)-1,2,3,4-tetrahydroisoquinoline-3-carboxamide

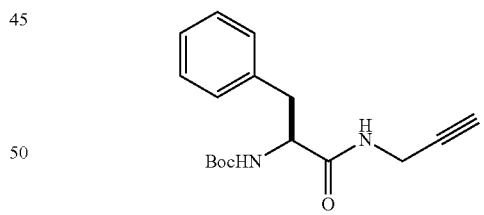

A) (S)-tert-Butyl (1-oxo-3-phenyl-1-(prop-2-yn-1-ylamino)propan-2-yl)carbamate

Following a procedure analogous to that for the synthesis of Compound D of Example 1, (S)-2-((tert-butoxycarbonyl)amino)-3-phenylpropanoic acid (Aldrich, 355 mg, 1.34 mmol) and prop-2-yn-1-amine (Combi-Blocks, 86 µL, 1.34 mmol) were converted to the title compound (401 mg, 99%). $^1$H NMR (CDCl$_3$) δ 7.39-7.16 (m, 5H), 6.01 (br s, 1H), 4.97 (br s, 1H), 4.33 (d, J=7.0 Hz, 1H), 4.07-3.84 (m, 2H), 3.08 (d, J=6.8 Hz, 2H), 2.20 (t, J=2.5 Hz, 1H), 1.47-1.33 (m, 9H); MS (ESI+) m/z 303.3 (M+H)+.

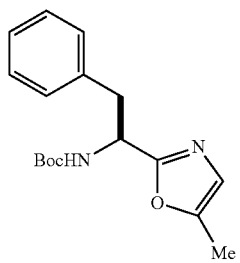

B) (S)-tert-Butyl (1-(5-methyloxazol-2-yl)-2-phenyl-ethyl)carbamate

To a solution of (S)-tert-butyl (1-oxo-3-phenyl-1-(prop-2-yn-1-ylamino)propan-2-yl)carbamate (95 mg, 0.31 mmol) in MeCN (1.6 mL) was added gold (III) chloride (9.5 mg, 0.031 mmol). The resulting reaction mixture was stirred at 50° C. overnight and then purified directly using flash chromatography (gradient from 0% to 100% EtOAc/hexanes) to give the title compound (69 mg, 73%) as a colorless oil. %). $^1$H NMR (CDCl$_3$) δ 7.37-7.17 (m, 3H), 7.05 (d, J=6.4 Hz, 2H), 6.63 (s, 1H), 5.12 (br s, 2H), 3.33-3.01 (m, 2H), 2.27 (d, J=1.1 Hz, 3H), 1.49-1.34 (m, 9H); MS (ESI$^+$) m/z 303.3 (M+H)$^+$.

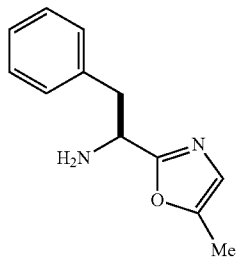

C) (S)-1-(5-Methyloxazol-2-yl)-2-phenylethanamine, TFA

Following a procedure analogous to that for the synthesis of Compound B of Example 78, (S)-tert-Butyl (1-(5-methyloxazol-2-yl)-2-phenylethyl)carbamate (69 mg, 0.23 mmol) was converted to the title compound and used without purification in the subsequent step. MS (ESI$^+$) m/z 203.1 (M+H)$^+$.

D) (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((S)-1-(5-methyloxazol-2-yl)-2-phenylethyl)carbamoyl)pyrrolidin-3-yl)-N—((R)-1,2,3,4-tetrahydronaphthalen-1-yl)-1,2,3,4-tetrahydroisoquinoline-3-carboxamide Following procedures analogous to those for the preparation of Compounds F and G of Example 46, (S)-2-((2S,4R)-1-((S)-2-((S)-2-((tert-butoxycarbonyl)(methyl)amino)propanamido)-3,3-dimethylbutanoyl)-4-((S)-2-((S)-2-((S)-2-((tert-butoxycarbonyl)(methyl)amino)propanamido)-3,3-dimethylbutanoyl)-3-(((R)-1,2,3,4-tetrahydronaphthalen-1-yl)carbamoyl)-1,2,3,4-tetrahydroisoquinolin-7-yl)pyrrolidine-2-carboxamido)-3-phenylpropanoic acid (Compound D of Example 46, 45 mg, 0.044 mmol) and (S)-1-(5-methyloxazol-2-yl)-2-phenylethanamine, TFA (15 mg, 0.049 mmol) were converted to the title compound (19 mg, 40% over 2 steps). MS (ESI$^+$) m/z 1001.1 (M+H)$^+$.

Example 82

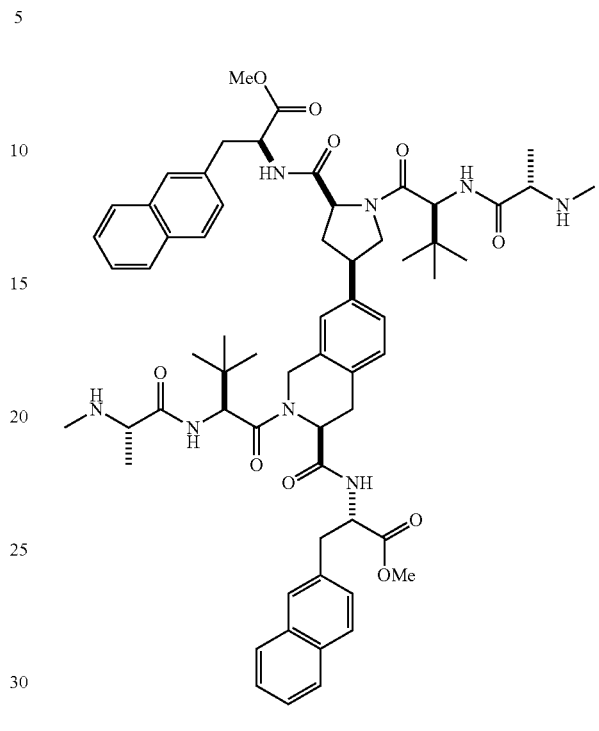

(S)-Methyl 2-((2S,4R)-1-((S)-3,3-dimethyl-2-((S)-2-(methylamino)propanamido)butanoyl)-4-((S)-2-((S)-3,3-dimethyl-2-((S)-2-(methylamino)propanamido) butanoyl)-3-(((S)-1-methoxy-3-(naphthalen-2-yl)-1-oxopropan-2-yl)carbamoyl)-1,2,3,4-tetrahydroisoquinolin-7-yl)pyrrolidine-2-carboxamido)-3-(naphthalen-2-yl)propanoate

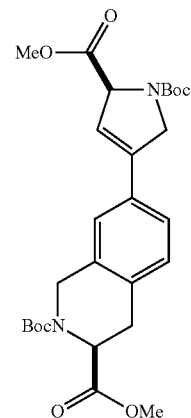

A) (S)-2-tert-Butyl 3-methyl 7-((S)-1-(tert-butoxycarbonyl)-5-(methoxycarbonyl)-2,5-dihydro-1H-pyrrol-3-yl)-3,4-dihydroisoquinoline-2,3(1H)-dicarboxylate Following a procedure analogous to that for the synthesis of Compound D of Example 22, (S)-1-tert-butyl 2-methyl 4-(((trifluoromethyl)sulfonyl)oxy)-1H-pyrrole-1,2(2H,5H)-dicarboxylate (585 mg, 1.56 mmol) and (S)-2-tert-butyl 3-methyl 7-(4,4,5,5-tetramethyl-1,3,2-dioxaborolan-2-yl)-3,4-dihydroisoquinoline-2,3(1H)-dicarboxylate (650 mg, 1.56 mmol) were converted to the title compound (563 mg, 70%). MS (ESI⁺) m/z 517.4 (M+H)⁺.

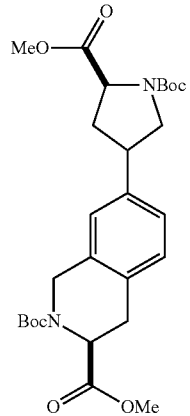

B) (S)-2-tert-Butyl 3-methyl 7-((3R,5S)-1-(tert-butoxycarbonyl)-5-(methoxycarbonyl)pyrrolidin-3-yl)-3,4-dihydroisoquinoline-2,3(1H)-dicarboxylate Following a procedure analogous to that for the synthesis of Compound C of Example 20, (S)-2-tert-butyl 3-methyl 7-((5)-1-(tert-butoxycarbonyl)-5-(methoxycarbonyl)-2,5-dihydro-1H-pyrrol-3-yl)-3,4-dihydroisoquinoline-2,3(1H)-dicarboxylate (563 mg, 1.09 mmol) was converted to the title compound (500 mg, 88%). MS (ESI) m/z 519.5 (M+H)⁺.

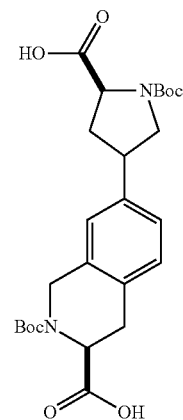

C) (S)-2-(tert-Butoxycarbonyl)-7-((3R,5S)-1-(tert-butoxycarbonyl)-5-carboxypyrrolidin-3-yl)-1,2,3,4-tetrahydroisoquinoline-3-carboxylic acid Following a procedure analogous to that for the synthesis of Compound K of Example 1, (3S)-2-tert-butyl 3-methyl 7-((5S)-1-(tert-butoxycarbonyl)-5-(methoxycarbonyl)pyrrolidin-3-yl)-3,4-dihydroisoquinoline-2,3(1H)-dicarboxylate (500 mg, 0.96 mmol) was converted to the title compound (450 mg, 95%). MS (ESI⁺) m/z 491.4 (M+H)⁺.

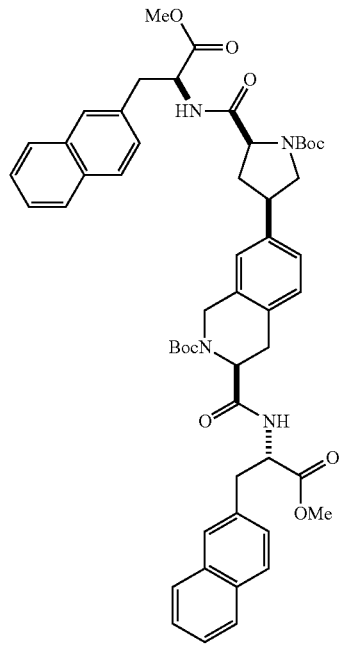

D) (S)-tert-Butyl 7-((3R,5S)-1-(tert-butoxycarbonyl)-5-(((S)-1-methoxy-3-(naphthalen-2-yl)-1-oxopropan-2-yl)carbamoyl)pyrrolidin-3-yl)-3-(((S)-1-methoxy-3-(naphthalen-2-yl)-1-oxopropan-2-yl)carbamoyl)-3,4-dihydroisoquinoline-2(1H)-carboxylate Following a procedure analogous to that for the synthesis of Compound F of Example 20, (S)-2-(tert-butoxycarbonyl)-7-((3R,5S)-1-(tert-butoxycarbonyl)-5-carboxypyrrolidin-3-yl)-1,2,3,4-tetrahydroisoquinoline-3-carboxylic acid (100 mg, 0.20 mmol) and (S)-methyl 2-amino-3-(naphthalen-2-yl)propanoate, HCl (135 mg, 0.51 mmol) were converted to the title compound (135 mg, 72%). MS (ESI⁺) m/z 913.7 (M+H)⁺.

E) (S)-Methyl 2-((2S,4R)-1-((S)-3,3-dimethyl-2-((S)-2-(methylamino)propanamido)butanoyl)-4-((S)-2-((S)-3,3-dimethyl-2-((S)-2-(methylamino)propanamido)butanoyl)-3-(((S)-1-methoxy-3-(naphthalen-2-yl)-1-oxopropan-2-yl)carbamoyl)-1,2,3,4-tetrahydroisoquinolin-7-yl)pyrrolidine-2-carboxamido)-3-(naphthalen-2-yl)propanoate Following procedures analogous to those described for the preparation of Compounds E, F and G of Example 20, (S)-tert-Butyl 7-((3R,5S)-1-(tert-butoxycarbonyl)-5-(((S)-1-methoxy-3-(naphthalen-2-yl)-1-oxopropan-2-yl)carbamoyl)pyrrolidin-3-yl)-3-(((S)-1-methoxy-3-(naphthalen-2-yl)-1-oxopropan-2-yl)carbamoyl)-3,4-dihydroisoquinoline-2(1H)-carboxylate (100 mg, 0.20 mmol) was converted to the title compound. MS (ESI⁺) m/z 1109.8 (M+H)⁺.

Examples 83 to 86

The following Examples were prepared according to the procedures described for the synthesis of Example 82.

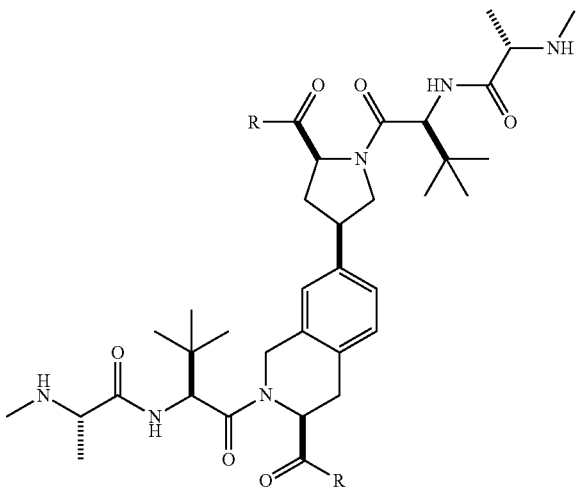

| Ex. No. | R | Name | LCMS (M + H) |
|---|---|---|---|
| 83 | HO, O, naphthalenylmethyl-CH(NH-)- | (S)-2-((S)-7-((3R,5S)-5-(((S)-1-Carboxy-2-(naphthalen-2-yl)ethyl)carbamoyl)-1-((S)-3,3-dimethyl-2-((S)-2-(methylamino)propanamido)butanoyl)pyrrolidin-3-yl)-2-((S)-3,3-dimethyl-2-((S)-2-(methylamino)propanamido)butanoyl)-1,2,3,4-tetrahydroisoquinoline-3-carboxamido)-3-(naphthalen-2-yl)propanoic acid | 1082.4 |
| 84 | MeO, benzyl-CH(NH-)- | (S)-2-((S)-3,3-Dimethyl-2-((S)-2-(methylamino) propanamido)butanoyl)-7-((3R,5S)-1-((S)-3,3-dimethyl-2-((S)-2-(methylamino)propanamido)butanoyl)-5-(((S)-1-methoxy-3-phenylpropan-2-yl)carbamoyl)pyrrolidin-3-yl)-N-((S)-1-methoxy-3-phenylpropan-2-yl)-1,2,3,4-tetrahydroisoquinoline-3-carboxamide | 981.7 |
| 85 | MeO, O, benzyl-CH(NH-)- | (S)-Methyl 2-((2S,4R)-1-((S)-3,3-dimethyl-2-((S)-2-(methylamino)propanamido)butanoyl)-4-((S)-2-((S)-3,3-dimethyl-2-((S)-2-(methylamino)propanamido) butanoyl)-3-(((S)-1-methoxy-1-oxo-3-phenylpropan-2-yl)carbamoyl)-1,2,3,4-tetrahydroisoquinolin-7-yl)pyrrolidine-2-carboxamido)-3-phenylpropanoate | 1009.7 |
| 86 | HO, O, benzyl-CH(NH-)- | (S)-2-((S)-7-((3R,5S)-5-(((S)-1-Carboxy-2-phenylethyl) carbamoyl)-1-((S)-3,3-dimethyl-2-((S)-2-(methylamino) propanamido)butanoyl)pyrrolidin-3-yl)-2-((S)-3,3-dimethyl-2-((S)-2-(methylamino)propanamido) butanoyl)-1,2,3,4-tetrahydroisoquinoline-3-carboxamido)-3-phenylpropanoic acid | 981.6 |

Example 87

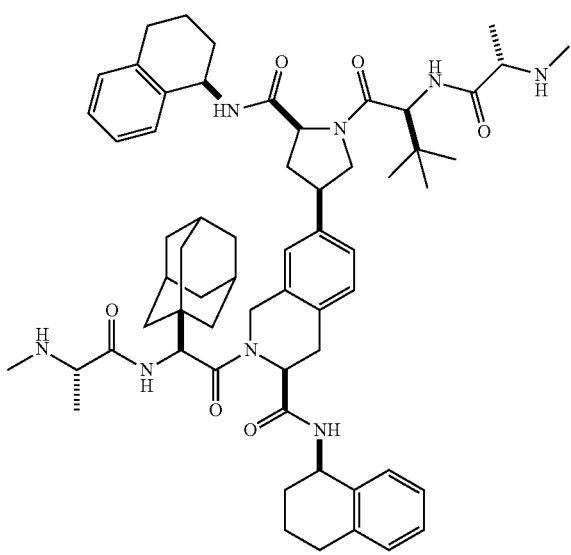

(S)-2-((S)-2-((3S,5S,7S)-Adamantan-1-yl)-2-((S)-2-(methylamino)propanamido)acetyl)-7-((3R,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N—((R)-1,2,3,4-tetrahydronaphthalen-1-yl)-1,2,3,4-tetrahydroisoquinoline-3-carboxamide, 2 TFA The title compound was prepared according to the procedures described for the synthesis of Example 24, substituting (S)-2-((3S,5S,7S)-adamantan-1-yl)-2-((tert-butoxycarbonyl)amino)acetic acid (Chem-Impex) for (S)-2-((((9H-fluoren-9-yl)methoxy)carbonyl)amino)-2-(tetrahydro-2H-pyran-4-yl)acetic acid. MS (ESI$^+$) m/z 1024.7 (M+H)$^+$.

Examples 88 and 89

The following Examples were prepared according to the procedures described for the synthesis of Example 1.

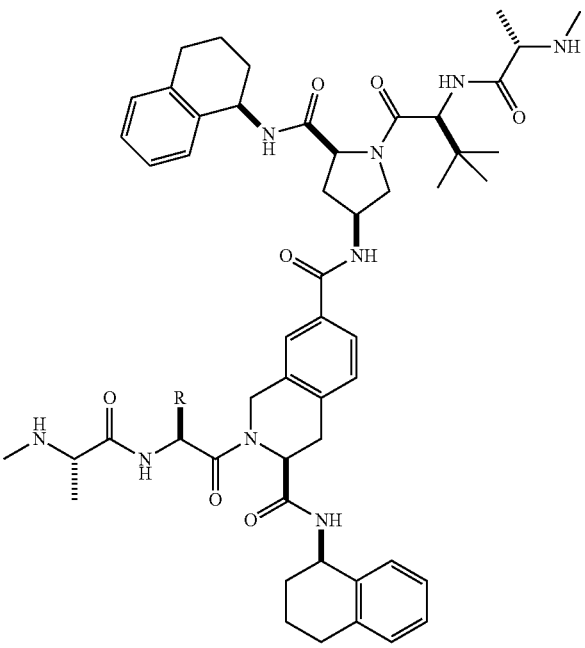

| Ex. No. | R | Name | LCMS (M + H) |
|---|---|---|---|
| 88 |  OH | (S)-N$^7$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-2-((S)-2-((1r,3R,5R,7S)-3-hydroxyadamantan-1-yl)-2-((S)-2-(methylamino)propanamido)acetyl)-N$^3$-((R)-1,2,3,4-tetrahydronaphthalen-1-yl)-1,2,3,4-tetrahydroisoquinoline-3,7-dicarboxamide | 1082.9 |

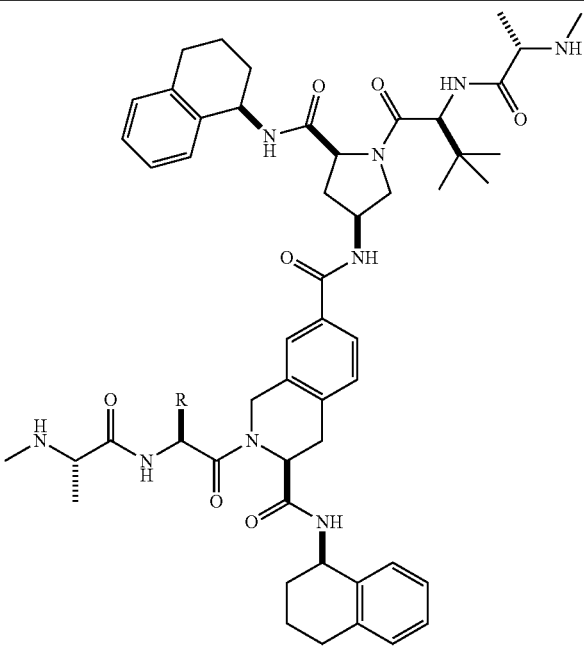

| Ex. No. | R | Name | LCMS (M + H) |
|---|---|---|---|
| 89 | (diphenylmethyl) | (S)-N⁷-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-2-((S)-2-((S)-2-(methylamino)propanamido)-3,3-diphenylpropanoyl)-N³-((R)-1,2,3,4-tetrahydronaphthalen-1-yl)-1,2,3,4-tetrahydroisoquinoline-3,7-dicarboxamide | 1098.8 |

EVALUATION OF BIOLOGICAL ACTIVITY

Exemplary compounds were tested for inhibition of XIAP BIR3 and XIAP BIR2-3 activity. Experimental procedures and results are provided below.

A. XIAP-BIR3/SMAC Homogeneous Time Resolved Fluorescence (HTRF) Assay

Assays were performed in black, flat-bottom, 384-well plates. The final assay volume was 50 L prepared from additions of His-BIR3 (241-356, XIAP), fluorescein labeled SMAC peptide, and test compounds in assay buffer consisting of 20 mM Sodium Phosphate, 1 mM EDTA, 50 mM NaCl, 50 g/ml BSA, and 0.05% PLURONIC® F68. The reaction was incubated at room temperature for 60 minutes, following which 10 µl of mouse anti-6×His-terbium labeled Fab (Medarex, Cis-bio) was added to the reaction (40 µl) for an additional 30 minute incubation. The HTRF signal, ratio of fluorescence intensities at emission wavelengths for fluorescein acceptor (520 nm) and terbium donor (615 nm), the 520/615 ratio, generated by the reaction was then measured on the Envision Plate Reader. Inhibition data were calculated from the 520/615 ratio generated by the no protein control reactions for 100% inhibition and vehicle-only reactions for 0% inhibition. The final concentration of reagents in the assay was 1 nM N-His-BIR3 (241-356, XIAP), 5 nM fluorescein labeled SMAC peptide, 0.25 nM anti-His-Tb-Fab, and 0.1% DMSO. Dose response curves were generated to determine the concentration required for inhibiting 50% of the HTRF signal ($IC_{50}$). Compounds were dissolved at 3 mM in dimethylsulfoxide (DMSO) and evaluated at eleven serially diluted concentrations. $IC_{50}$ and $K_i$ values were derived by non-linear regression analysis.

B. XIAP-BIR2-3 dimeric SMAC Peptide Homogeneous Time Resolved Fluorescence (HTRF) Assay Assays were performed in black, flat-bottom, 384-well plates. The final assay volume was 50 L prepared from additions of His-BIR2-3 (125-356, C202A/C213G, XIAP), fluorescein labeled dimeric SMAC peptide, and test compounds in assay buffer consisting of 20 mM Sodium Phosphate, 1 mM EDTA, 50 mM NaCl, 50 g/ml BSA, and 0.05% PLURONIC® F68. The reaction was incubated at room temperature for 60 minutes, following which 10 µl of mouse anti-6×His-Tb IgG (Medarex, Cis-bio) was added to the reaction (401) for an additional 30 minute incubation. The HTRF signal, ratio of fluorescence intensities at emission wavelengths for fluorescein acceptor (520 nm) and terbium donor (615 nm), the 520/615 ratio, generated by the reaction was then measured on the Envision Plate Reader. Inhibition data were calculated from the 520/615 ratio generated by the no protein control reactions for 100% inhibition and vehicle-only reactions for 0% inhibition. The final concentration of reagents in the assay was 0.5 nM N-His-BIR2-3 (125-356, C202A/C213G, XIAP), 20 nM fluorescein labeled dimeric SMAC peptide, 0.25 nM anti-His-Tb-Fab, and 0.1% DMSO. Dose response curves were generated to determine the concentration required for inhibiting 50% of the HTRF signal ($IC_{50}$). Compounds were dissolved at 3 mM in dimethylsulfoxide (DMSO) and evaluated at eleven serially diluted concentrations. $IC_{50}$ and $K_i$ values were derived by non-linear regression analysis.

Results

Results of the BIR2 and BIR2-3 assays are shown in the Table below.

| | "NT" means that the compound was not tested in the assay. | |
|---|---|---|
| Example No. | XIAP BIR3 IC$_{50}$ (μM) | XIAP BIR2-3 IC$_{50}$ (μM) |
| 1 | 0.011 | 0.003 |
| 2 | 0.009 | 0.006 |
| 3 | 0.006 | 0.003 |
| 4 | 0.010 | 0.011 |
| 5 | 0.014 | 0.013 |
| 6 | 0.014 | 0.002 |
| 7 | 0.006 | 0.006 |
| 8 | 0.011 | 0.002 |
| 9 | 0.033 | 0.003 |
| 10 | 0.063 | 0.004 |
| 11 | 0.025 | 0.010 |
| 12 | 0.019 | 0.015 |
| 13 | 0.006 | 0.002 |
| 14 | 0.029 | 0.015 |
| 15 | 0.016 | 0.005 |
| 16 | 0.019 | 0.010 |
| 17 | 0.002 | 0.002 |
| 18 | 0.009 | 0.004 |
| 19 | 0.007 | 0.002 |
| 20 | 0.013 | 0.003 |
| 21 | 0.030 | 0.003 |
| 22 | 0.002 | 0.001 |
| 23 | 0.004 | 0.003 |
| 24 | 0.003 | 0.001 |
| 25 | 0.004 | 0.003 |
| 26 | 0.011 | 0.196 |
| 27 | 0.005 | 0.001 |
| 28 | 0.0051 | 0.0022 |
| 29 | 0.0117 | 0.0008 |
| 30 | 0.0039 | 0.0057 |
| 31 | 0.0138 | 0.0012 |
| 32 | 0.0087 | 0.0019 |
| 33 | 0.0018 | 0.0017 |
| 34 | 0.0048 | 0.0070 |
| 35 | 0.0025 | 0.0013 |
| 36 | 0.0033 | 0.0017 |
| 37 | 0.0029 | 0.0018 |
| 38 | 0.0032 | 0.0018 |
| 39 | 0.0072 | 0.0056 |
| 40 | 0.0015 | 0.0009 |
| 41 | 0.0046 | 0.0015 |
| 42 | 0.0016 | 0.0012 |
| 43 | 0.0020 | 0.0013 |
| 44 | 0.0103 | 0.0174 |
| 45 | 0.0092 | 0.0042 |
| 46 | 0.0102 | 0.0016 |
| 47 | 0.0175 | 0.0024 |
| 48 | 0.0008 | 0.0007 |
| 49 | 0.0004 | 0.0005 |
| 50 | 0.0009 | 0.0012 |
| 51 | 0.0194 | 0.0096 |
| 52 | 0.0034 | 0.0012 |
| 53 | 0.0539 | 0.0869 |
| 54 | 0.0068 | 0.0029 |
| 55 | 0.0377 | 0.0085 |
| 56 | 0.0088 | 0.0020 |
| 57 | 0.0099 | 0.0026 |
| 58 | 0.0076 | 0.0023 |
| 59 | 0.0067 | 0.0022 |
| 60 | NT | NT |
| 61 | 0.0221 | 0.0034 |
| 62 | 0.0092 | 0.0019 |
| 63 | 0.0167 | 0.0030 |
| 64 | 0.0256 | 0.0038 |
| 65 | 0.0054 | 0.0016 |
| 66 | 0.0133 | 0.0031 |
| 67 | 0.0093 | 0.0021 |
| 68 | 0.0049 | 0.0013 |
| 69 | 0.0086 | 0.0015 |
| 70 | 0.0089 | 0.0022 |
| 71 | 0.0056 | 0.0015 |
| 72 | 0.0165 | 0.0033 |
| 73 | NT | NT |
| 74 | 0.0136 | 0.0026 |
| 75 | 0.0145 | 0.0030 |
| 76 | 0.0189 | 0.0025 |
| 77 | 0.0017 | 0.0008 |
| 78 | 0.0089 | 0.0028 |
| 79 | 0.0167 | 0.0034 |
| 80 | 0.0073 | 0.0026 |
| 81 | 0.0135 | 0.0026 |
| 82 | 0.1108 | 0.0682 |
| 83 | 0.0192 | 0.0262 |
| 84 | 0.0314 | 0.0081 |
| 85 | 0.0148 | 0.0062 |
| 86 | 0.0050 | 0.0027 |
| 87 | 0.0073 | 0.0059 |
| 88 | 0.0090 | 0.0026 |
| 89 | 0.0378 | 0.3596 |

What is claimed is:

1. A compound of Formula (I)

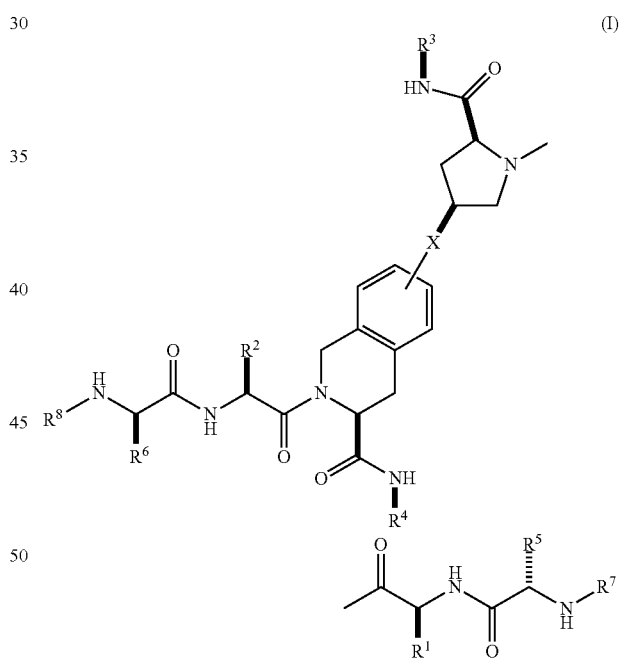

wherein
X is a direct bond, —NH—, —O—, —NHCO— or —CONH—;
$R^1$ is optionally substituted alkyl, optionally substituted cycloalkyl or optionally substituted aryl;
$R^2$ is optionally substituted alkyl, optionally substituted cycloalkyl, optionally substituted thioalkyl, optionally substituted cycloalkylalkyl, optionally substituted heterocyclyl, optionally substituted arylalkyl or optionally substituted aryl;
$R^3$ and $R^4$ are independently optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;

R⁵ and R⁶ are independently hydrogen, optionally substituted alkyl or optionally substituted cycloalkyl;

R⁷ and R⁸ are independently hydrogen or optionally substituted alkyl;

or a pharmaceutically acceptable salt, tautomer or stereoisomer thereof.

2. A compound of Formula (Ia)

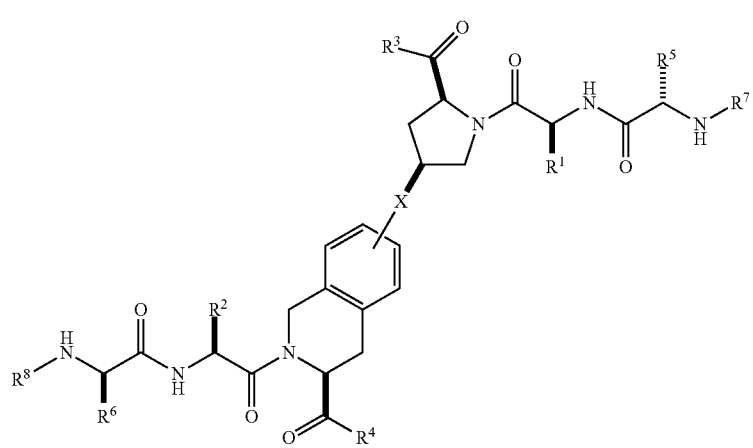

(1a)

wherein:

X is a direct bond, —NH—, —O—, —NHCO— or —CONH—;

R¹ is optionally substituted alkyl, optionally substituted cycloalkyl or optionally substituted aryl;

R² is optionally substituted alkyl, optionally substituted cycloalkyl, optionally substituted thioalkyl, optionally substituted cycloalkylalkyl, optionally substituted heterocyclyl, optionally substituted arylalkyl or optionally substituted aryl;

R³ and R⁴ are independently

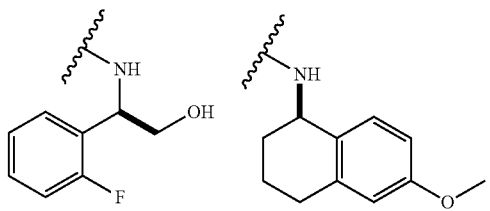

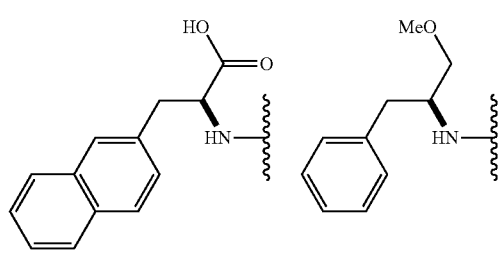

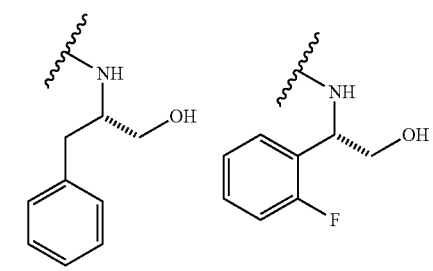

-continued

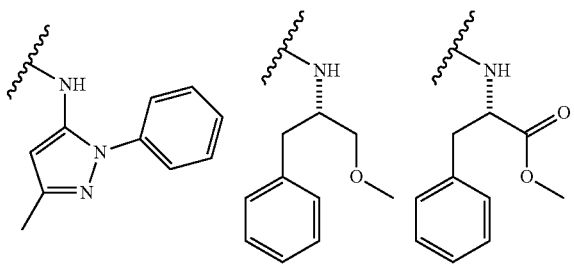

-continued

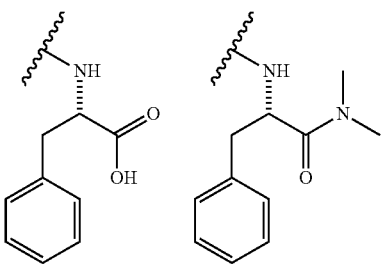

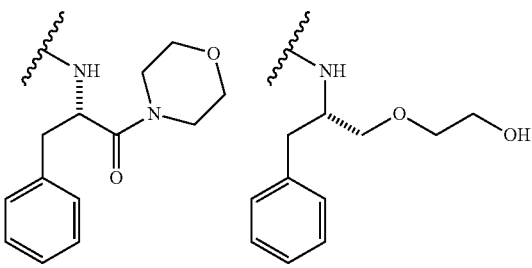

183
-continued
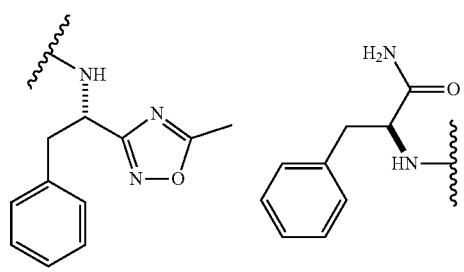
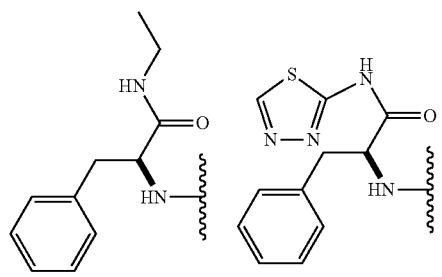
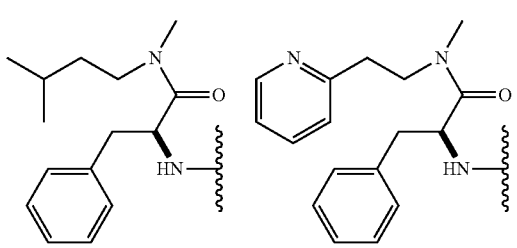
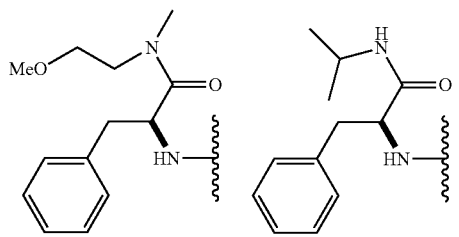
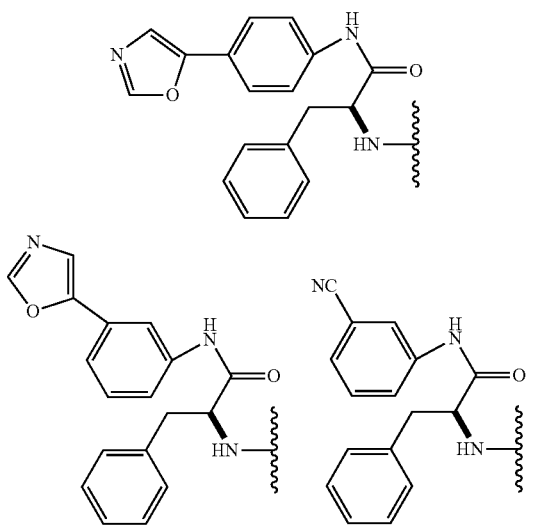
184
-continued
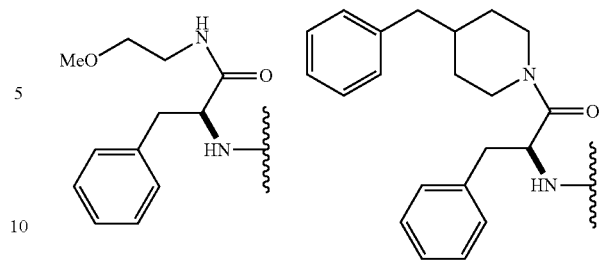
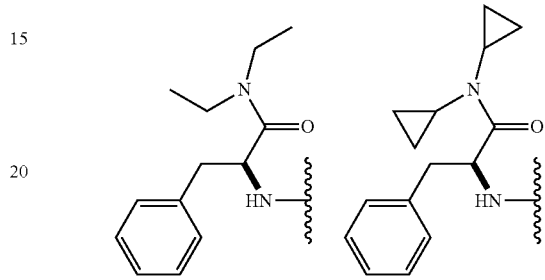
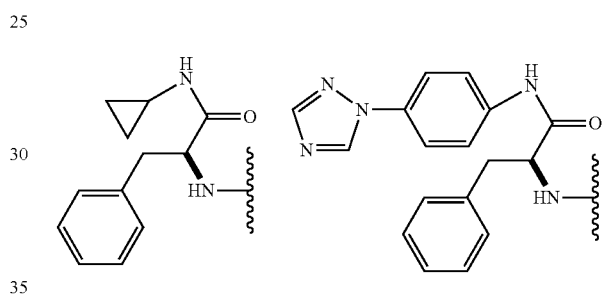
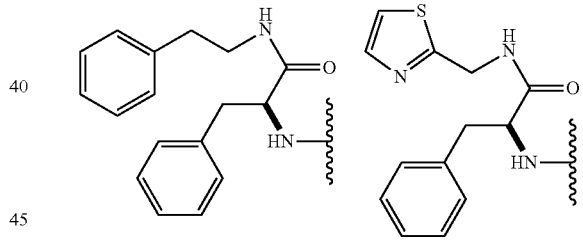
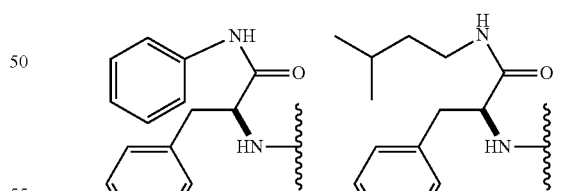
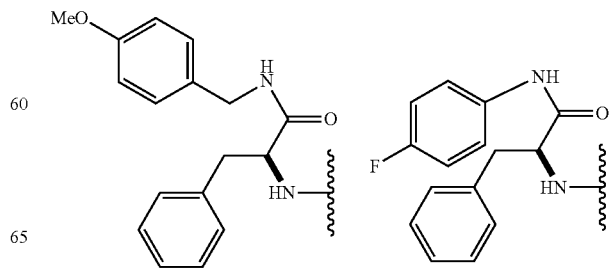

-continued

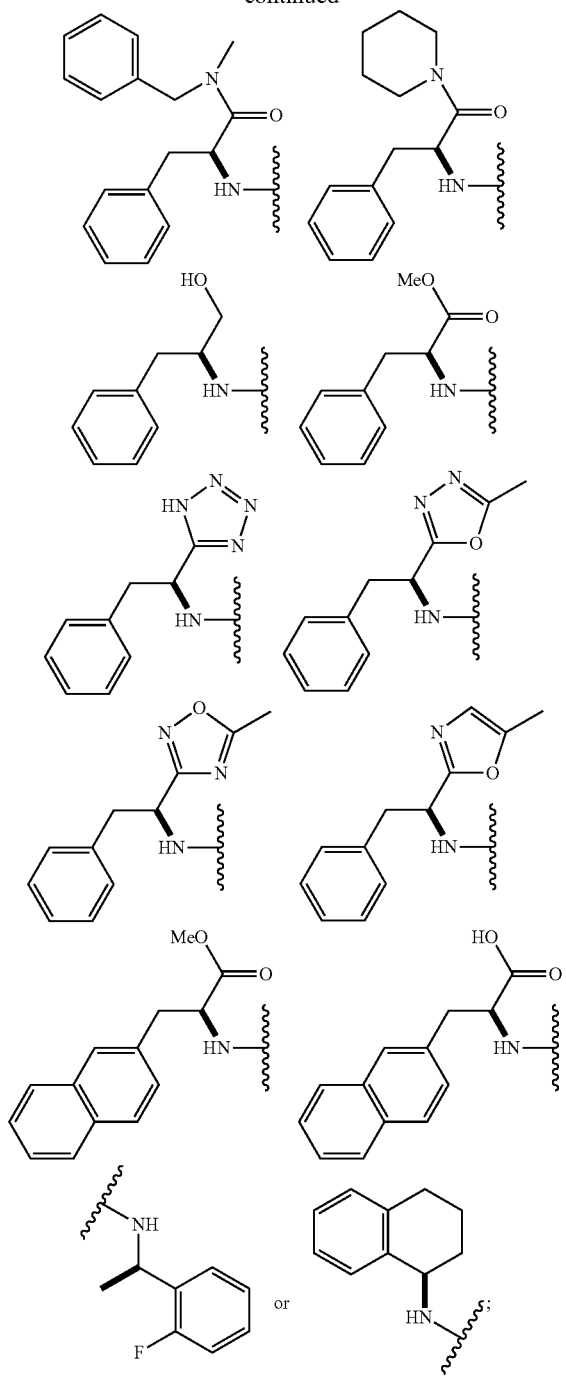

R[5] and R[6] are independently hydrogen, optionally substituted alkyl or optionally substituted cycloalkyl;
R[7] and R[8] are independently hydrogen or optionally substituted alkyl;
or a pharmaceutically acceptable salt, tautomer or stereoisomer thereof.

3. The compound according to claim 1 wherein
X is a direct bond, —NHCO— or —CONH—;
R[1] is optionally substituted alkyl;
R[2] is optionally substituted alkyl, optionally substituted cycloalkyl, optionally substituted thioalkyl, optionally substituted cycloalkylalkyl, optionally substituted heterocyclyl or optionally substituted arylalkyl;
R[3] and R[4] are independently optionally substituted alkyl, optionally substituted aryl, or optionally substituted arylalkyl;
R[5] and R[6] are independently hydrogen, optionally substituted alkyl or optionally substituted cycloalkyl;
R[7] and R[8] are independently methyl or ethyl;
or a pharmaceutically acceptable salt, tautomer or stereoisomer thereof.

4. The compound according to claim 3
wherein
R[1] is alkyl;
R[2] is alkyl, cycloalkyl, cycloalkylalkyl, heterocyclyl or phenylalkyl, wherein the phenyl group is substituted with one or more alkyl or halogen groups;
R[3] and R[4] are independently optionally substituted alkyl, optionally substituted aryl, or optionally substituted arylalkyl;
or a pharmaceutically acceptable salt, tautomer or stereoisomer thereof.

5. The compound according to claim 4 wherein:
R[1] is t-butyl;
R[2] is alkyl, cycloalkyl, cycloalkylalkyl, tetrahydropyran or phenylalkyl, wherein the phenyl group is substituted with one or more fluoro groups;
R[3] is 1,2,3,4-tetrahydronaphthalenyl;
R[4] is 1,2,3,4-tetrahydronaphthalenyl or optionally substituted arylalkyl; wherein said aryl group of the arylalkyl is substituted with alkyl or halogen;
or a pharmaceutically acceptable salt, tautomer or stereoisomer thereof.

6. A compound of Formula (II)

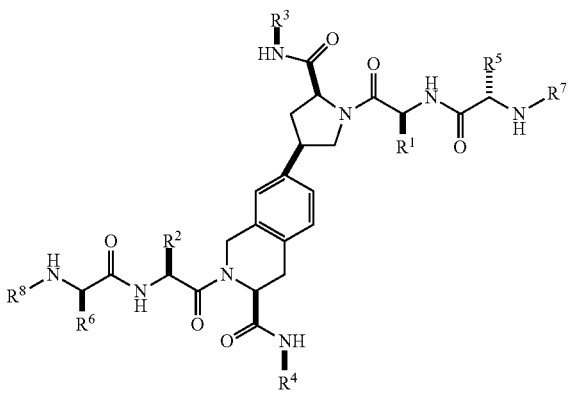

(II)

wherein
R[1] is optionally substituted alkyl;
R[2] is optionally substituted alkyl, optionally substituted cycloalkyl, optionally substituted thioalkyl, optionally substituted cycloalkylalkyl, optionally substituted heterocyclyl or optionally substituted arylalkyl;
R[3] and R[4] are independently optionally substituted alkyl, optionally substituted aryl, or optionally substituted arylalkyl;
R[5] and R[6] are independently hydrogen, optionally substituted alkyl or optionally substituted cycloalkyl;
R[7] and R[8] are independently methyl or ethyl;
or a pharmaceutically acceptable salt, tautomer or stereoisomer thereof.

7. A compound according to claim 6 wherein

R¹ is optionally substituted alkyl;

R² is optionally substituted alkyl, optionally substituted cycloalkyl, optionally substituted cycloalkylalkyl, optionally substituted heterocyclyl or optionally substituted arylalkyl;

R³ and R⁴ are independently optionally substituted alkyl, optionally substituted aryl, or optionally substituted arylalkyl;

R⁵ and R⁶ are independently hydrogen, optionally substituted alkyl or optionally substituted cycloalkyl;

R⁷ and R⁸ are independently methyl or ethyl;

or a pharmaceutically acceptable salt, tautomer or stereoisomer thereof.

8. A compound of Formula (IIa)

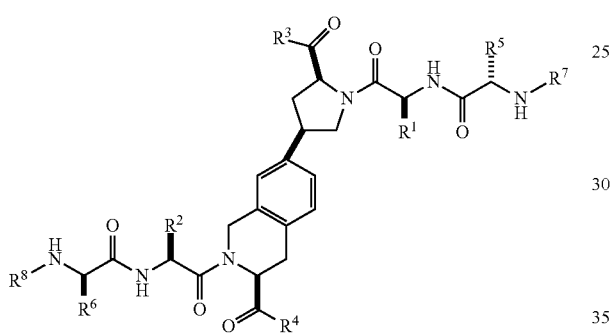

(IIa)

wherein

R¹ is optionally substituted alkyl;

R² is optionally substituted alkyl, optionally substituted cycloalkyl, optionally substituted thioalkyl, optionally substituted cycloalkylalkyl, optionally substituted heterocyclyl or optionally substituted arylalkyl;

R³ and R⁴ are independently

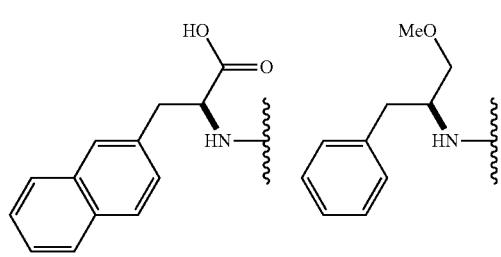

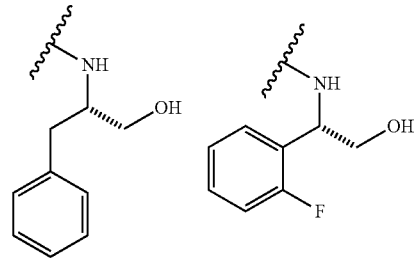

-continued

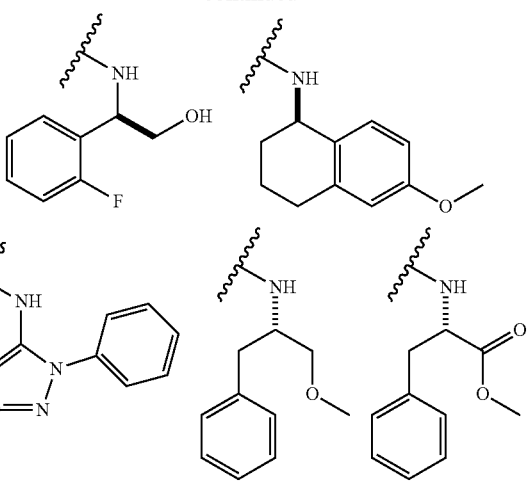

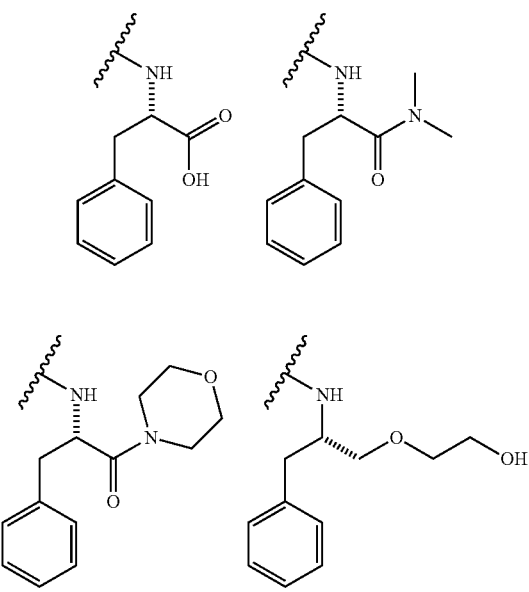

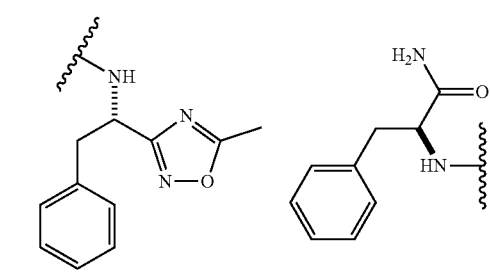

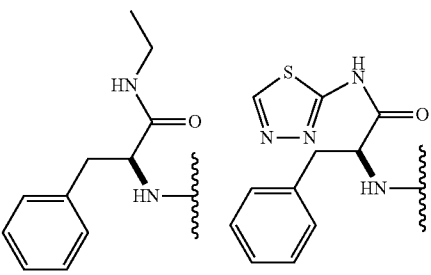

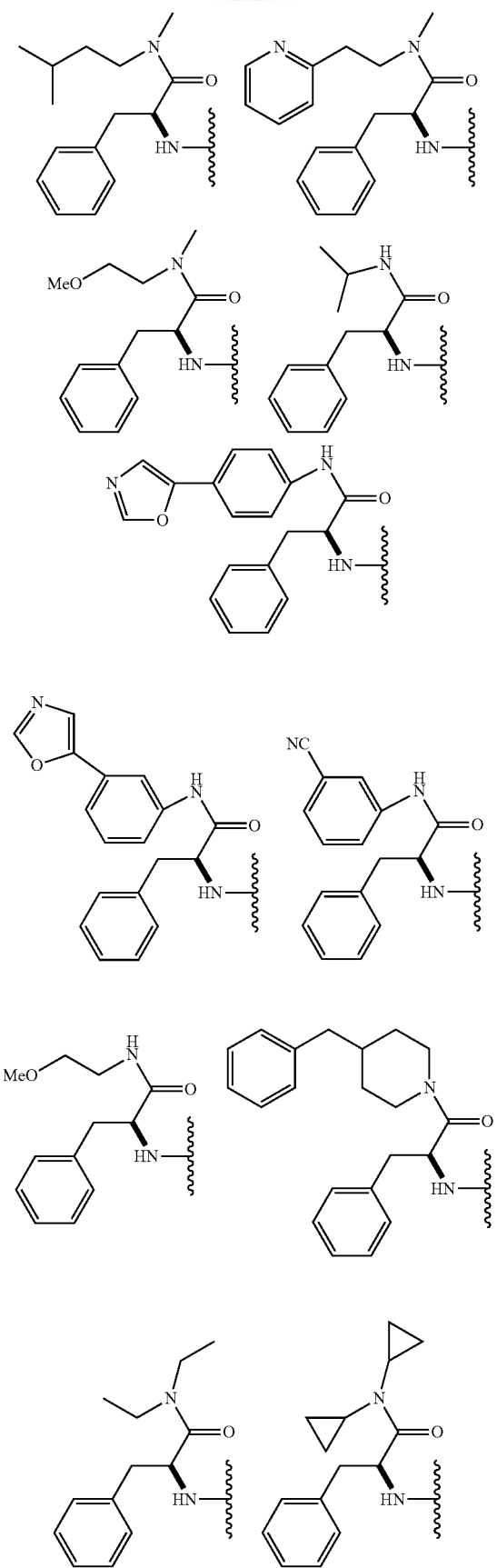
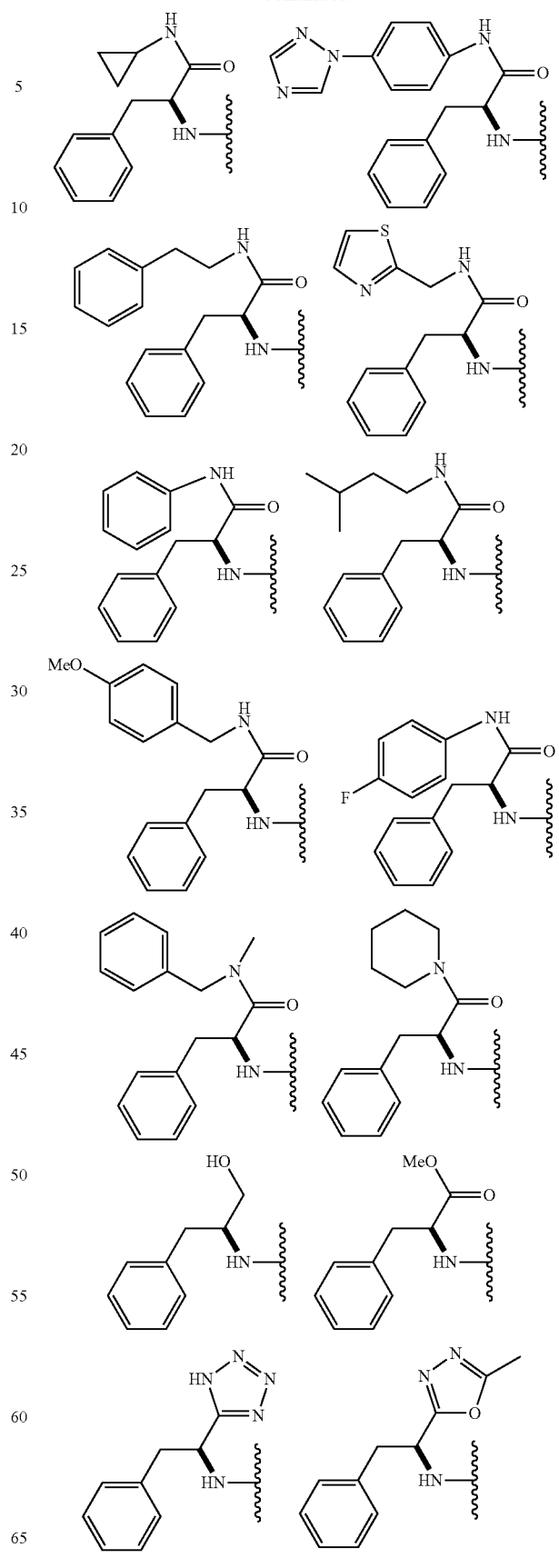

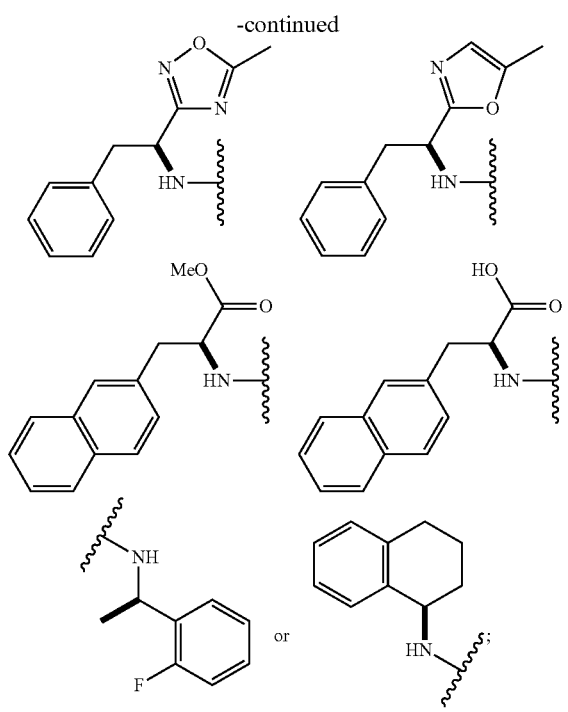

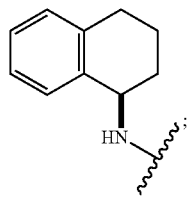 [SMILES: *N[C@@H]1CCCc2ccccc21 ; ";"]

$R^5$ and $R^6$ are independently hydrogen, optionally substituted alkyl or optionally substituted cycloalkyl;
$R^7$ and $R^8$ are independently methyl or ethyl;
or a pharmaceutically acceptable salt, tautomer or stereoisomer thereof.

9. The compound according to claim 8 wherein
$R^1$ and $R^2$ are independently optionally substituted alkyl;
$R^3$ and $R^4$ are independently $R^5$ and $R^6$ are independently methyl or ethyl;
$R^7$ and $R^8$ are independently methyl or ethyl;
or a pharmaceutically acceptable salt, tautomer or stereoisomer thereof.

10. A compound of Formula (III)

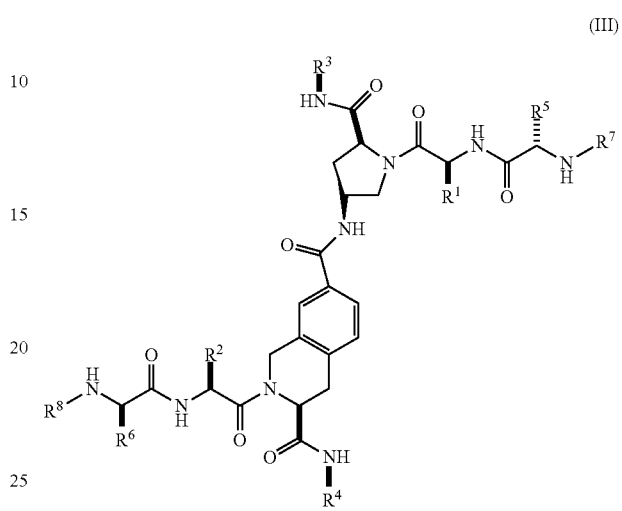

(III)

wherein
$R^1$ is optionally substituted alkyl;
$R^2$ is optionally substituted alkyl, optionally substituted cycloalkyl, optionally substituted thioalkyl, optionally substituted cycloalkylalkyl, optionally substituted heterocyclyl or optionally substituted arylalkyl;
$R^3$ and $R^4$ are independently optionally substituted alkyl, optionally substituted aryl, or optionally substituted arylalkyl;
$R^5$ and $R^6$ are independently hydrogen, optionally substituted alkyl or optionally substituted cycloalkyl;
$R^7$ and $R^8$ are independently optionally substituted alkyl;
or a pharmaceutically acceptable salt, tautomer or stereoisomer thereof.

11. A pharmaceutical composition comprising a compound of claim 1 and a pharmaceutically acceptable carrier.

12. A pharmaceutical composition comprising a compound of claim 5 and a pharmaceutically acceptable carrier.

13. A pharmaceutical composition comprising a compound of claim 8 and a pharmaceutically acceptable carrier.

* * * * *